United States Patent
Fares et al.

(10) Patent No.: US 10,030,060 B2
(45) Date of Patent: *Jul. 24, 2018

(54) LONG-ACTING POLYPEPTIDES AND METHODS OF PRODUCING SAME

(71) Applicant: OPKO Biologics Ltd., New Ziona (IL)

(72) Inventors: Fuad Fares, Hourfish Village (IL); Udi Eyal Fima, Beer-Sheva (IL)

(73) Assignee: OPKO Biologics Ltd., Kiryat Gat (IL)

( * ) Notice: Subject to any disclaimer, the term of this patent is extended or adjusted under 35 U.S.C. 154(b) by 8 days.

This patent is subject to a terminal disclaimer.

(21) Appl. No.: 14/566,370

(22) Filed: Dec. 10, 2014

(65) Prior Publication Data

US 2015/0203558 A1    Jul. 23, 2015

Related U.S. Application Data

(60) Division of application No. 13/867,728, filed on Apr. 22, 2013, now Pat. No. 8,999,670, which is a division of application No. 13/191,478, filed on Jul. 27, 2011, now Pat. No. 8,426,166, which is a division of application No. 12/476,916, filed on Jun. 2, 2009, now Pat. No. 8,048,849, which is a continuation-in-part of application No. 12/401,746, filed on Mar. 11, 2009, now Pat. No. 8,097,435, which is a continuation of application No. 11/700,910, filed on Feb. 1, 2007, now Pat. No. 7,553,940.

(60) Provisional application No. 60/764,761, filed on Feb. 3, 2006.

(51) Int. Cl.
| C07K 14/555 | (2006.01) |
| C07K 1/00 | (2006.01) |
| C07K 14/505 | (2006.01) |
| C07K 14/59 | (2006.01) |
| C07K 14/61 | (2006.01) |
| A61K 47/64 | (2017.01) |
| A61K 38/19 | (2006.01) |

(52) U.S. Cl.
CPC ............ *C07K 14/555* (2013.01); *A61K 47/64* (2017.08); *C07K 14/505* (2013.01); *C07K 14/59* (2013.01); *C07K 14/61* (2013.01); *A61K 38/19* (2013.01); *C07K 2319/00* (2013.01); *C07K 2319/31* (2013.01); *C07K 2319/35* (2013.01); *C07K 2319/91* (2013.01)

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | MacConnel |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,880,634 A | 11/1989 | Speiser |
| 4,911,691 A | 3/1990 | Aniuk et al. |
| 5,011,771 A | 4/1991 | Bellet et al. |
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |

(Continued)

FOREIGN PATENT DOCUMENTS

| CN | 1528787 A | 9/2004 |
| CN | 1528894 A | 3/2006 |

(Continued)

OTHER PUBLICATIONS

Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).

Amirizahdeh et al. "Expression of biologically active recombinant B-domain-deleted human VIII in mammalian cells" Journal of Science, Islamic Republic of Iran. Abstract. 16(2):103-112, (2005).

Anson et al. "The gene structure of human anti-haemophilic factor IX", The EMBO Journal (1984) 3(5):1053-1060.

Askoy et al., "A study of the intracellular and secreted forms of the MUC2 mucin from the PC/AA intestinal cell line." Glycobiology 9.7: 739-746 (1999).

Banerji et al. "A lymphocyte-specific cellular enhancer is located downstream of the joining region in immunoglobulin heavy chain genes" Cell 33:729-740 (1983).

(Continued)

*Primary Examiner* — Elizabeth C. Kemmerer
*Assistant Examiner* — Regina M DeBerry
(74) *Attorney, Agent, or Firm* — Mark S. Cohen; Pearl Cohen; Zedek Latzer Baratz LLP

(57) ABSTRACT

A polypeptide and polynucleotides encoding same comprising one carboxy-terminal peptide (CTP) of chorionic gonadotrophin attached to an amino terminus of a cytokine and two carboxy-terminal peptides (CTP) of chorionic gonadotrophin attached to a carboxy terminus of a cytokine are disclosed. Pharmaceutical compositions comprising the polypeptide and polynucleotides of the invention and methods of using same are also disclosed.

16 Claims, 28 Drawing Sheets

(56) References Cited

U.S. PATENT DOCUMENTS

| | | | |
|---|---|---|---|
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,919,455 A | 7/1999 | Greenwald et al. |
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,563,612 B2 | 7/2009 | Saxena et al. |
| 7,585,837 B2 | 9/2009 | Shechter et al. |
| 7,649,084 B2 | 1/2010 | Lehmann et al. |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 2001/0007757 A1 | 7/2001 | Boime et al. |
| 2002/0127652 A1 | 9/2002 | Schambye et al. |
| 2002/0160944 A1 | 10/2002 | Boime et al. |
| 2003/0113871 A1 | 6/2003 | Lee et al. |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1* | 8/2008 | Minev .................. C07K 14/705 424/192.1 |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152182 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0048878 A1 | 3/2012 | Burger et al. |
| 2012/0114651 A1 | 5/2012 | De Wildt et al. |
| 2012/0208759 A1 | 8/2012 | Fima et al. |
| 2013/0184207 A1 | 7/2013 | Fares et al. |
| 2013/0243747 A1 | 9/2013 | Fima et al. |
| 2014/0113860 A1 | 4/2014 | Fima et al. |
| 2014/0170728 A1 | 6/2014 | DeFrees et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0072924 A1 | 3/2015 | Fima et al. |
| 2015/0158926 A1 | 6/2015 | Fares et al. |

FOREIGN PATENT DOCUMENTS

| | | |
|---|---|---|
| EP | 0264166 | 4/1988 |
| EP | 0374257 A1 | 6/1990 |
| JP | 2002226365 A | 8/2002 |
| JP | 2002255857 A | 9/2002 |
| JP | 2004269516 A | 9/2004 |
| KR | 20030037598 A | 5/2003 |
| KR | 20050021502 A | 5/2003 |
| WO | WO 1993/006844 | 4/1993 |
| WO | WO 1994/024148 A1 | 10/1994 |
| WO | WO 2000/023472 A2 | 4/2000 |
| WO | WO 2002/036169 A2 | 5/2002 |
| WO | WO 2002/048194 A1 | 6/2002 |
| WO | WO 2002/085311 A2 | 10/2002 |
| WO | WO 2003/038100 A1 | 5/2003 |
| WO | WO 2003/046013 A1 | 6/2003 |
| WO | WO 2004/006756 | 1/2004 |
| WO | WO 2005/080544 | 9/2005 |
| WO | WO 2006/051288 A2 | 5/2006 |
| WO | WO 2006/134340 | 12/2006 |
| WO | WO 2007/094985 | 8/2007 |
| WO | WO 2007/149406 A2 | 12/2007 |
| WO | WO 2010/007622 | 1/2010 |
| WO | WO 2011/004361 | 1/2011 |
| WO | WO 2011/087672 | 7/2011 |
| WO | WO 2012/011752 | 5/2012 |
| WO | WO 2012/167251 | 12/2012 |
| WO | WO 2013/157002 | 10/2013 |

(56) References Cited

FOREIGN PATENT DOCUMENTS

| WO | WO 2013/183052 | 12/2013 |
|---|---|---|
| WO | WO 2014/080401 | 5/2014 |

OTHER PUBLICATIONS

Barker et al. "An immunomagnetic-base method for the purification of ovarian cancer cells from patient-derived ascites"(Gynecologic Oncology 82, 57-63, 2001).

Beeley, Glycoprotein and proteoglycan techniques. Elsevier: 69-72 (1985).

Bengtsson et al. "Treatment of adults with growth hormone (GH) deficiency with recombinant human GH" J Clin Endocrinol Metab. Feb. 1993;76(2):309-17.

Berntorp et al. "The pharmacokinetics of clotting factor therapy"; Haemophilia (2003) 9:353-359.

Biller et al. "Effects of once-weekly sustained-release growth hormone: a double-blind, placebo-controlled study in adult growth hormone deficiency", J Clin Endocrinol Metab. Jun. 2011;96(6):1718-26.

Bitter et al. "Expression and secretion vectors for yeast" (1987) Methods in Enzymol. 153:516-544.

Bjorkman et al. Pharmacokinetics of Coagulation Factors Clinical Relevance for Patients with Haemophilia. Clin Pharmacokinet vol. 40 (11): 815-832 (2001).

Bohl et al. "Improvement of erythropoiesis in b-thalassemic mice by continuous erythropoietin delivery from muscle" Blood 95:2793-2798 (2000).

Boissel et al. "Erythropoietin structure-function relationships" The Journal of Biological Chemistry 268(21):15983-15993 (1993).

Booth et al. "The use of a 'universal' yeast expression vector to produce an antigenic protein of Mycobacterium leprae" Immunol. Lett. 19:65-70 (1988).

Bouloux, P. M. G., et al. "First human exposure to FSH-CTP in hypogonadotrophic hypogonadal males." Human Reproduction 16.8 (2001): 1592-1597.

Brisson et al. "Expression of a bacterial gene in plants by using a viral vector" Nature, 310:511-514 (1984).

Broglie et al. "Light-Regulated Expression of a Pea Ribulose-1 ,5-Bisphosphat Carboxylase Small Subunit Gene in Transformed Plant Cells" Science 224:838-843 (1984).

Brunetti-Pierri et al. "Bioengineered factor IX molecules with increased catalytic activity improve the therapeutic index of gene therapy vectors for hemophilia B." Human Gene Therapy 20.5: 479-485 (2009).

Buchwald et al. "Long-term, continuous intravenous heparin administration by an implantable infusion pump in ambulatory patients with recurrent venous thrombosis" Surgery 88:507-516 (1980).

Butler et al., "The beta-subunit of human chorionic gonadotrophin exists as a homodimer." Journal of Molecular Endocrinology 22.2: 185-192 (1999).

Byrne et al. "Multiplex gene regulation: A two-tiered approach to transgene regulation in transgenic mice" Proc. Natl. Acad. Sci USA 86:5473-5477 (1989).

Calame et al. "Transcriptional Controlling Elements in the Immunoglobulin and T Cell Receptor Loci" Adv. Immunol 43:235-275 (1988).

Cawley et al. "Developing long-acting growth hormone formulations", Clinical Endocrinology (2013) 79, 305-309.

Chan et al. "Plasma Insulin-Like Growth Factor-I and Prostate Cancer Risk: A Prospective Study", Science vol. 279:563-566, Jan. 1998.

Chen et al. "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).

Chen et al., "Glycoengineering Approach to Half-Life Extension of Recombinant Biotherapeutics." Bioconjugate Chemistry 23.8: 1524-1533 (2012).

Chen et al., "Modulating antibody pharmacokinetics using hydrophilic polymers." Expert Opinion on Drug Delivery 8.9: 1221-1236 (2011).

Chihara et al. "Clinical aspect of growth hormone deficiency in adults", Nihon Naika Gakkai Zasshi. Sep. 10, 2000;89(9):2010-8; with English Abstract.

Claxton et al., "A systematic review of the associations between dose regimens and medication compliance." Clinical Therapeutics 23.8: 1296-1310 (2001).

Coleman et al., "Dosing frequency and medication adherence in chronic disease." Journal of managed care pharmacy: JMCP 18.7: 527-539 (2012).

Coruzzi et al. "Tissue-specific and light-regulated expression of a pea nuclear gene encoding the small subunit of ribulose-1,5-bisphosphate carboxylase" The EMBO Journal 3:1671-1680 (1984).

Cutfield et al., "Non-compliance with growth hormone treatment in children is common and impairs linear growth." PLoS One 6.1: e16223 (2011), pp. 1-3.

Dalton et al. "Over-expression of secreted proteins from mammalian cell lines", Protein Sci. May 2014;23(5):517-25.

Database Geneseq [Online] Apr. 7, 2005, "Human interferon beta (without signal peptide)." XP002664024 retrieved from EBI accession No. GSP: ADW02285, Database accession No. ADW02285.

Database Geneseq [Online] 18 Mar. 24, 2005; "Epogen signal peptide", XP002685292, retrieved from EBI accession No. GSP:ADS64918, Database accession No. ADW649.

Davis CG et al. "Deletion of clustered O-linked carbohydrates does not impair function of low density lipoprotein receptor in transfected fibroblasts" J Biol Chem. 261(6):2828-38, Feb. 25, 1986.

Diederichs et al., "Liposome in kosmetika und arzneimitteln." Pharmazeutische Industrie 56.3: 267-275 (1994).

Diness, et al. Lund-Hansen, and U. Hedner. "Effect of recombinant human FVIIA on warfarin-induced bleeding in rats." Thrombosis research 59.6 (1990): 921-929.

Dong et al. "The prolonged half-lives of new erythropoietin derivatives via peptide addition" Biochemical Research Communications, 339(1):380-385 (Jan. 6, 2006).

Drake et al. "Optimizing GH therapy in adults and children" Endocr Rev. Aug. 2001;22(4):425-50. Review.

Edlund et al. "Cell-Specific Expression of the Rat Insulin Gene: Evidence for Role of Two Distinct 5' Flanking Elements" Science 230:912-916 (1985).

Eschbach et al. "Correction of the Anemia of End-Stage Rental Disease with Recombinant Human Erythropoietin", The New England Journal of Medicine Jan. 8, 1987, vol. 316 No. 2, pp. 73-78.

European Search Report Application No. EP 10796803 dated Feb. 28, 2013.

European Search Report for Application No. 12150722.2 dated Jun. 4, 2012.

European Search Report for Application No. 07749922 dated Oct. 8, 2009.

European Search Report for Application No. 14196333.0 dated Mar. 2, 2015.

European Search Report for Application No. 14197286.9 dated Mar. 2, 2015.

European Search Report for European Patent Application No. 10796803.4 dated Feb. 28, 2013.

European Search Report for European Patent Application No. 12179805 dated Nov. 9, 2012.

European Search Report for European Patent Application No. 12179821 dated Nov. 12, 2012.

European Search Report for European Patent Application No. 13856398.6 dated Jul. 5, 2016.

Fares "The role of O-linked and N-linked oligosaccharides on the structure—function of glycoprotein hormones: Development of agonists and antagonists", Biochimica et Biophysica Acta (BBA)—General Subjects 1760.4: 560-567 (2006).

(56) References Cited

OTHER PUBLICATIONS

Fares et al. "Design of a long-acting follitropin agonist by fusing the C-terminal sequence of the chorionic gonadotropin beta subunit to the follitropin beta subunit" Proc Natl Acad Sci U S A., 89(10): 4304-4308, May 15, 1992.
Fares et al. "Designing a long-acting human growth hormone (hGH) by fusing the carboxy-terminal peptide of human chorionic gonadotropin B-subunit to the coding sequence of hGH" Endocrinology 151(9):4410-4417 (2010).
Fares et al. "Growth hormone (GH) retardation of muscle damage due to immobilization in old rats. Possible intervention with a new long-acting recombinant GH" Ann N Y Acad Sci. 786:430-43 (Jun. 15, 1996).
Fares et al. "Designing a Long Acting Erythropoietin by Fusing Three Carboxyl-Terminal Peptides of Human Chorionic Gondotropin [beta] Subunit to the N-Terminal and C-Terminal Coding Sequence", International Journal of Cell Biology, vol. 9, No. 11, Jan. 1, 2011, pp. 2021-2027.
Fares et al., "Development of a long-acting erythropoietin by fusing the carboxyl-terminal peptide of human chorionic gonadotropin ß-subunit to the coding sequence of human erythropoietin." Endocrinology 148.10: 5081-5087 (2007).
Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.
Fingl et al., "General Principles." The Pharmacological Basis of Therapeutics (ed. Goodman, LS & Gilman, A,): 1-46 (1975).
Fogarty, Patrick F. "Biological rationale for new drugs in the bleeding disorders pipeline." ASH Education Program Book 2011.1 (2011): 397-404.
Freshney "Culture of animal cells: A manual of basic technique" (Culture of Animal Cells, A Manual of Basic Technique, Alan R. Liss, Inc., 1983, New York, pp. 1-4).
Fuentes-Prior et al. "Structural basis for the anticoagulant activity of the thrombin-thrombomodulin complex" Nature. Mar. 30, 2000; 404 (6777):518-25.
Furuhashi et al. "Fusing the carboxy-terminal peptide of the chorionic gonadotropin (CG)-subunit to the common alpha-submit:: Retention of O-linked glycosylation and enhanced in vivo bioactivity of chimeric human CG" Molecular Endocrinology 9(1):54-63 (1995).
Furuhashi et al. "Processing of O-linked glycosylation in the chimera consisting of alpha-subunit and carboxyl-terminal peptide of the human chorionic gonadotropin beta-subunit is affected by dimer formation with follicle-stimulating hormone beta-subunit" Endocrine Journal 51(1):53-59 (2004).
Gao et al., "Erythropoietin gene therapy leads to autoimmune anemia in macaques" Blood 103(9):3300-3302 (2004).
Garcia-Campayo et al. "Unmasking a new recognition signal for< i> O</i>-linked glycosylation in the chorionic gonadotropin ß subunit" Molecular and Cellular Endocrinology 194.1: 63-70 (2002).
Gardella et al. "Expression of Human Parathyroid Hormone-( I-84) in *Escherichia coli* as a Factor X-cleavable Fusion Protein" J. Biol. Chem. 265:15854-15859 (1990).
Gellerfors et al. "Characterisation of a secreted form of recombinant derived human growth hormone, expressed in *Escherichia coli* cells", J Pharm Biomed Anal 7(2):173-83 (1989).
Ghosh et al., "Activity and regulation of factor Vlla analogs with increased potency at the endothelial cell surface." Journal of Thrombosis and Haemostasis 5.2: 336-346 (2007).
Gilboa et al., "Transfer and Expression of Cloned Genes Using Retroviral Vectors", Biotechniques, vol. 4:504-512, (1986).
Goodson, in "Medical applications of controlled release." vol. 2: 115-138 (1984).
Guitton et al., "Influence of in vitro non-enzymatic glycosylation on the physicochemical parameters of type I collagen." Collagen and Related Research 4.4: 253-264 (1984).
Gurley et al. "Upstream Sequences Required for Efficient Expression of a Soybean Heat Shock Gene" Mol.Cell.Biol 6:559-565 (1986).
Hacke et al. "Intravenous thrombolysis with recombinant tissue plasminogen activator for acute hemispheric stroke. The European Cooperative Acute Stroke Study (ECASS)" JAMA. 1995;274(13)1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Heffernan et al., "Effects of oral administration of a synthetic fragment of human growth hormone on lipid metabolism." American Journal of Physiology—Endocrinology and Metabolism 279.3: E501-E507 (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International Search Report and Written Opinion for PCT Application No. PCT/IL09/00700 dated Feb. 4, 2010.
International Search Report and Written Opinion for PCT Application No. PCT/IL10/00532 dated Apr. 11, 2011.
International Search Report and Written Opinion for PCT Application No. PCT/IL13/50107 dated Jul. 10, 2013.
International Search Report and Written Opinion for PCT Application No. PCT/US07/02767 dated Feb. 15, 2008.
International Search Report and Written Opinion for PCT Application No. PCT/US07/03014 dated Sep. 22, 2008.
International Search Report for Application No. PCTIL2014050910 dated Jan. 25, 2015.
International Search Report for PCT Application No. PCT/IL 12/50288 dated Jan. 28, 2013.
Isgaard et al. "Effects of local administration of GH and IGF-1 on longitudinal bone growth in rats" Am J Physiol. Apr. 1986;250(4 Pt 1):E367-72.
Joshi et al. "Recombinant thyrotropin containing a beta-subunit chimera with the human chorionic gonadotropin-beta carboxyterminus is biologically active, with a prolonged plasma half-life: role of carbohydrate in bioactivity in metabolic clearance" Endocrinology. Sep. 1995;136(9):3839-48.
Kanda et al. "Genetic Fusion of an a-subunit Gene to the Follicle-Stimulating Hormone and Chorionic Gonadotropin-b Subunit Genes: Production of a Bifunctional Protein", Molecular Endocrinolog, vol. 13, No. 11, p. 1873-1881, Nov. 1999.
Kelly et al. "Outcomes of patients with Burkitt lymphoma older than age 40 treated with intensive chemotherapeutic regimens." Clin Lymphoma Myeloma. Aug. 2009;9(4):307-10.
Kessler et al. "Structure and location of the O-glycosidic carbohydrate units of human chorionic gonadotropin" J Biol Chem. 25;254(16):7909-14 , Aug. 1979.
Kessler et al., "Structures of N-Glycosidic Carbohydrate Units of Human Chorionic Gonadotropin" J Biol Chem. Aug. 25, 1979;254(16):7901-8.
Kicman et al., "Human chorionic gonadotrophin and sport." British Journal of Sports Medicine 25.2 : 73-80 (1991).
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Kotler et al., "Effects of growth hormone on abnormal visceral adipose tissue accumulation and dyslipidemia in HIV-infected patients." JAIDS Journal of Acquired Immune Deficiency Syndromes 35.3: 239-252 (2004).
Langer Robert "New Methods of Drug Delivery" Science 249:1527-1533 (1990).

(56) References Cited

OTHER PUBLICATIONS

Larsen et al., "Accumulation of magnetic iron oxide nanoparticles coated with variably sized polyethylene glycol in murine tumors." Nanoscale 4.7: 2352-2361 (2012).
Le et al., "Improved Vancomycin Dosing in Children Using Area Under the Curve Exposure." Pediatr Infect Dis J vol. 32, pp. e155-e163 (2013).
Lentz et al., "Posttranslational modification of the carboxy-terminal region of the. beta. subunit of human chorionic gonadotropin." Biochemistry 23.22: 5330-5337 (1984).
Li et al. "Bioassay of hGH .I. Weight gain of hypophysectomized rats". Abstract, Yaowu Fenxi Zazhi 15(2), 3-7 (1995).
Lippin et al. "Human erythropoietin gene therapy for patients with chronic renal failure" Blood 106(7):2280-2286 (2005).
Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.
Lopez-Berenstein, Liposomes in the Therapy of Infectious Disease and Cancer, Lopez-Berestein and Fidler (eds.), Liss, New York, pp. 317-327 (1989).
Lopez-Berestein et al. "Treatment of systemic fungal infections with liposomal amphotericin B." Arch Intern Med. Nov. 1989;149(11):2533-6.
Maheshwari et al., "Manipulation of Electrostatic and Saccharide Linker Interactions in the Design of Efficient Glycopolypeptide-Based Cholera Toxin Inhibitors." Micromolecular bioscience 10.1: 68-81 (2010).
Maston et al., "Chorionic gonadotropin beta subunit [Homo sapiens]" NCBI Accession No. AAL69705.1 (Apr. 3, 2002).
Matsumoto et al. The measurement of low levels of factor VIII or factor IX in hemophilia A and hemophilia B plasma by clot waveform analysis and thrombin generation assay. Journal of Thrombosis and Haemostasis vol. 4:377-384 (2006).
Matsuo et al. "Thrombolysis by human tissue plasminogen activator and urokinase in rabbits with experimental pulmonary embolus" Nature. Jun. 18, 1981;291(5816):590-1.
Maun et al., "Disulfide locked variants of factor VIIa with a restricted ß-strand conformation have enhanced enzymatic activity." Protein Science 14.5: 1171-1180 (2005).
Mcalister et al. "NMR analysis of the N-terminal SRCR domain of human CD5: engineering of a glycoprotein for superior characteristics in NMR experiments." Protein Engineering 11.10: 847-853 (1998).
Meulien et al., "Increased biological activity of a recombinant factor IX variant carrying alanine at position+ 1." Protein Engineering 3.7: 629-633 (1990).
Milton et al. The Delineation of a Decapeptide Gonadotropin-releasing Sequence in the Carboxyl-terminal Extension of the Human Gonadotropin releasing Hormone Precursor. The Journal of Biological Chemistry, vol. 261/36:16990-16997 (Dec. 1986).
Morgan et al. "The amino acid sequence of human chorionic gonadotropin. The alpha subunit and beta subunit", J Biol Chem. Jul. 10, 1975;250(13):5247-58.
Muleo et al. Small doses of recombinant factor VIIa in acquired deficiencies of vitamin K dependent factors. Blood Coagulation & Fibrinolysis Abstract, 10(8), 521-522 (1999).
Murray et al. "Dose titration and patient selection increases the efficacy of GH replacement in severely GH deficient adults", Clinical Endocrinology (1999) 50, pp. 749-757.
Mutter et al. "A New Base-Labile Anchoring Group for Polymer-Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Nezu et al. "Treatment of idiopathic pituitary dwarfism with human growth hormone", ournal of Nara Medical Association 1989, vol. 40, No. 1, p. 16-22; with English Abstract.

Ngo et al. "Computational Complexity, Protein Structure Protein Prediction and the Levinthal Paradox" in Birkhauser The Protein Folding Problem And Tertiary Structure Prediction, pp. 433-440 and 492-495 (1994).
Office Action for Japanese Application No. 2014-523441 dated May 24, 2016.
Ogle et al. "Renal effects of growth hormone. I. Renal function and kidney growth", Pediatr. Nephrol. vol. 6:394-398, 1992.
Oosterhof et al. Regulation of whole body energy homeostasis with growth hormone replacement therapy and endurance exercise Physiol Genomics. Jun. 28, 2011;43(12):739-48. doi: 10.1152/physiolgenomics.00034.2010. Epub Mar. 29, 2011.
Pedrosa et al., "Selective neoglycosylation increases the structural stability of vicilin, the 7S storage globulin from pea seeds." Archives of Biochemistry and Biophysics 382.2: 203-210 (2000).
Persson et al. "Recombinant coagulation factor VIIa—from molecular to clinical aspects of a versatile haemostatic agent", Thrombosis Research (2010) 125:483-489.
Persson et al., "Rational design of coagulation factor VIIa variants with substantially increased intrinsic activity." Proceedings of the National Academy of Sciences 98.24:13583-13588 (2001).
Philips A. "The challenge of gene therapy and DNA delivery" J Pharm. Pharmacology 53:1169-1174 (2001).
Pierce et al. "Glycoprotein hormones: structure and function." Annual review of biochemistry 50.1: 465-495 (1981).
Pinkert et al. "An albumin enhancer located 10 kb upstream functions along with its promoter to direct liver-specific expression in transgenic mice" Genes Dev. 1:268-277 (1987).
Polizzotti et al. "Effects of saccharide spacing and chain extension on toxin inhibition by glycopolypeptides of well-defined architecture", Macromolecules 40.20:7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Rebois et al., "Hydrodynamic properties of the gonadotropin receptor from a murine Leydig tumor cell line are altered by desensitization." Biochemistry 26.20: 6422-6428 (1987).
Reichel "SARCOSYL-PAGE: A new electrophoretic method for the separation and immunological detection of PEGylated proteins." Protein Electrophoresis. Humana Press 65-79 (2012).
Reiter et al. "A multicenter study of the efficacy and safety of sustained release GH in the treatment of naive pediatric patients with GH deficiency" J Clin Endocrinol Metab. 86(10):4700-6 (Oct. 2001).
Ronzi et al. Optimisation of a freeze-drying process of high purity Factor VIII and Factor IX concentrates. Chemical Engineering and Processing. vol. 42:751-757 (2003).
Rudman et al. "Effects of human growth hormone in men over 60 years old" N Engl J Med. Jul. 5, 1990;323(1):1-6.
Russell et al. "Local injections of human or rat growth hormone or of purified human somatomedin-C stimulate unilateral tibial epiphyseal growth in hypophysectomized rats" Endocrinology. Jun. 1985;116(6):2563-7.
Saudek et al. "A preliminary trial of the programmable implantable medication system for insulin delivery " N Engl J Med. 321 :574 (1989), pp. 574-579.
Schein, Catherine H. "The shape of the messenger: Using protein structure information to design novel cytokine-based therapeutics" Abstract; Current Pharmaceutical Design 8(24):2113-2129 (2002).
Scheuttrumpf et al., "Factor IX variants improve gene therapy efficacy for hemophilia B." Blood 105.6: 2316-2323 (2005).
Schulte "Half-life extension through albumin fusion technologies", Thrombosis Research (2009) 124 Suppl. 2;S6-S8.
Sefton, "Implantable pumps." Critical Reviews in Biomedical Engineering 14.3: 201-240 (1986).
Sheffield et al. "Effects of genetic fusion of factor IX to albumin on in vivo clearance in mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab.15 Suppl 2:715-22. (May 2002).

(56) References Cited

OTHER PUBLICATIONS

Smeland et al. "Treatment of Burkitt's/Burkitt-like lymphoma in adolescents and adults: a 20-year experience from the Norwegian Radium Hospital with the use of three successive regimens." Ann Oncol. Jul. 2004;15(7):1072-8.
Speiser et al. "Optimization of spray-dried and -congealed lipid micropellets and characterization of their surface morphology." Pharm. Res. 8:47-54 (1991).
Srour et al. "Regulation of human factor IX expression using doxycycline-inducible gene expression system" Thromb Haemost 90:398-405 (2003).
Studier F.W. et al "Use of T7 RNA Polymerase to Direct Expression of Cloned Genes" Methods in Enzymol. 185:60-89 (1990).
Su et al. "Curcumin Inhibits Human Lung Cell Carcinoma Cancer Tumour Growth in a Murine Xenograft Model" (Phytother. Res. 24:189-191, 2010).
Sugahara et al. "Characterization of the O-glycosylation sites in the chorionic gonadotropin ß subunit in vivo using site-directed mutagenesis and gene transfer." Journal of Biological Chemistry 271.34: 20797-20804 (1996).
Supplementary European Search Report for Application No. 12819794.4 dated Feb. 24, 2015.
Supplementary European Search Report for EP patent application No. 09797630.2, dated Dec. 5, 2011.
Takamatsu et al. "Expression of bacterial chloramphenicol acetyltransferase gene in tobacco plants mediated by TMV-RNA" EMBO J 6:307-311 (1987).
Treat, J, Greenspan, AR, and Rahman, A. Liposome Encapsulated Doxorubicin—Preliminary Results of Phase I and Phase II Trials. in: G Lopez-Berestein, IJ Fidler (Eds.) Liposomes in the Therapy of Infectious Diseases and Cancer. Alan R. Liss, New York; 1989: 353-365.
Uenalp et al. "Factor VII deficiency associated with valproate treatment" Pediatrics International 50(3):403-405 Abstract (2008).
Venn et al. "Biosynthesis and metabolism in vivo of intervertebral-disc proteoglycans in the mouse." Biochem. J 215: 217-225 (1983).
Weiss et al. "Noncompliance in Neurologic Patients" Current Treatment Options in Neurology 7:419-425 (2005).
Weissbach and Weissbach, "Methods for Plant Molecular Biology." Selected Methods in Enzymology (USA) Section VIII: 421-463 (1988).
Wells, J.A, "Additivity of Mutational Effects in Proteins" Biochemistry 29:8509-8517 (1990).
White et al. "Mammalian Recombinant Coagulation Proteins: Structure and Function", Transfus Sci. (1998) 19(2):177-189.
Wildt et al., "The humanization of N-glycosylation pathways in yeast." Nature Reviews Microbiology 3.2: 119-128 (2005).
Wilken et al. "A novel four-amino acid determinant defines conformational freedom within chorionic gonadotropin ß-subunits." Biochemistry 46.14: 4417-4424 (2007).
Winoto et al. "A novel, inducible and T cell-specific enhancer located at the 3' end of the T cell receptor alpha locus" EMBO J. 8:729-733 (1989).
Wynne et al. "Subcutaneous oxyntomodulin reduces body weight in overweight and obese subjects a double-blind, randomized, controlled trial." Diabetes 54.8 (2005):2390-2395.
Yefenof & Mcconnell "Interferon amplifies complement activation by Burkitt's lymphoma cells" Nature. Feb. 21-27, 1985;313(6004):68, pp. 684-685.
Yin et al. "Recombinant human growth hormone replacement therapy in HIV-associated wasting and visceral adiposity". Exper. Rev. Anti-Infect. Ther. 3(5):727-736 (2005).
Zheng et al., "The impact of glycosylation on monoclonal antibody conformation and stability." MAbs. vol. 3. No. 6. Landes Bioscience (Nov.-Dec. 2011), pp. 568-576.
Zhong et al. "The N-terminal epidermal growth factor-like domain in factor IX and factor X represents an important recognition motif for binding to tissue factor" J. Biol. Chem. (2002) 277(5):3622-31.
Carles-Bonnet et al. "H-Lys-Arg-Asn-Lys-Asn-Asn-OH is the minimal active structure of oxyntomodulin." Peptides 17.3 (1996): 557-561.
Edmunds et al. "Plasma erythropoietin levels and acquired cystic disease of the kidney in patients receiving regular haemodialysis treatment" Br J Haematol. Jun. 1991;78(2):275-7.
European Search Report for European Patent No. 16187710.5 dated Oct. 14, 2016.
Jarrousse et al. "Oxyntomodulin (glucagon-37) and its C-terminal octapeptide inhibit gastric acid secretion", FEBS Lett. Aug. 19, 1985; 188(1): 81-4.
Krantz et al. "Specific binding of erythropoietin to spleen cells infected with the anemia strain of Friend virus" Proc Natl Acad Sci U S A. Dec. 1984;81(23):7574-8.
Littlewood, T.J. "Erythropoietin for the treatment of anemia associated with hematological malignancy" Hematol Oncol. Mar. 2001;19(1):19-30.
Musto "The role of recombinant erythropoietin for the treatment of anemia in multiple myeloma" Leuk Lymphoma. Apr. 1998;29(3-4):283-91.
Stuart et al. "Polycythemia vera" Am Fam Physician. May 1, 2004;69(9):2139-44.
Tharakan et al. "Emerging therapies in the treatment of 'diabesity': beyond GLP-1" Trends Pharmacol Sci. Jan. 2011;32(1):8-15.
Verhoef et al. "Recombinant human erythropoietin for the treatment of anemia in the myelodysplastic syndromes: a clinical and erythrokinetic assessment" Ann Hematol. Jan. 1992;64(1):16-21.
European Search Report for European Application No. 17161199.9 dated Aug. 7, 2017.
International Search Report for Application No. PCT/IL2017/050645 dated Sep. 21, 2017.
International Search Report for Application No. PCT/IL2017/050784 dated Sep. 22, 2017.

\* cited by examiner

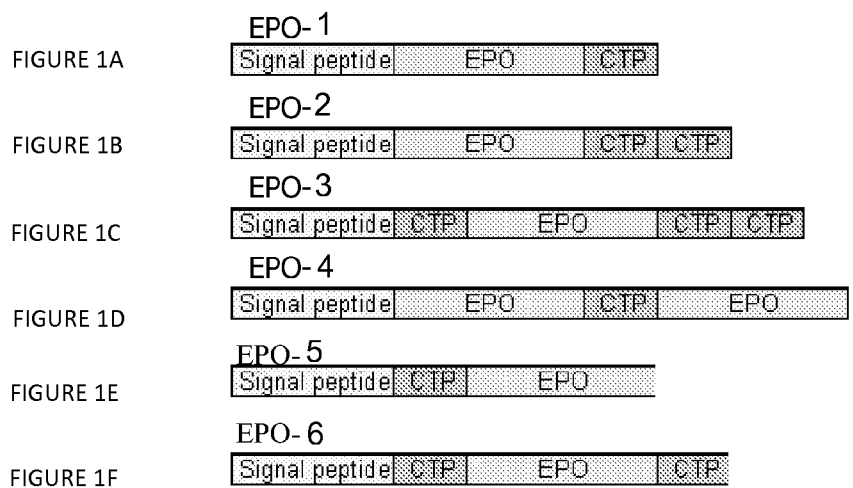
FIGURE 1A
FIGURE 1B
FIGURE 1C
FIGURE 1D
FIGURE 1E
FIGURE 1F
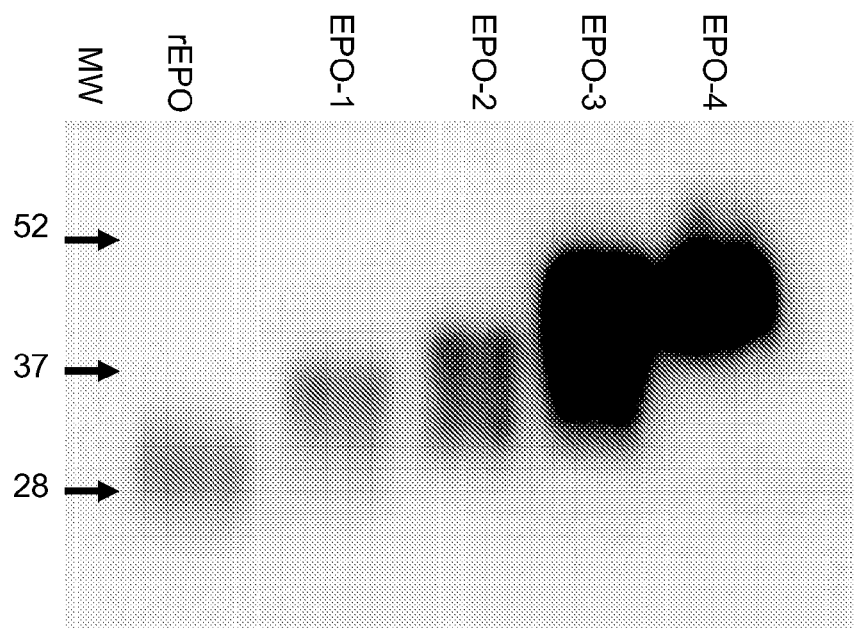
FIGURE 2

Human Interferon-β 1a-MOD-9010

A) hIFNβ 1a

AA sequence (Accession No. NP_002167.1)

```
M  T  N  K  C  L  L  Q  I  A  L  L  L  C  F  S  T  T  A  L  S  M  S  Y
N  L  L  G  F  L  Q  R  S  S  N  F  Q  C  Q  K  L  L  W  Q  L  N  G  R
L  E  Y  C  L  K  D  R  M  N  F  D  I  P  E  E  I  K  Q  L  Q  Q  F  Q
K  E  D  A  A  L  T  I  Y  E  M  L  Q  N  I  F  A  I  F  R  Q  D  S  S
S  T  G  W  N  E  T  I  V  E  N  L  L  A  N  V  Y  H  Q  I  N  H  L  K
T  V  L  E  E  K  L  E  K  E  D  F  T  R  G  K  L  M  S  S  L  H  L  K
R  Y  Y  G  R  I  L  H  Y  L  K  A  K  E  Y  S  H  C  A  W  T  I  V  R
V  E  I  L  R  N  F  Y  F  I  N  R  L  T  G  Y  L  R  N
```

Total: 186 aa

Nucleotides Sequence (Accession No. NM_002176)

B)
```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa acgtgctgg aagagaagct ggaaaaggag gacttcacca ggggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccggct acctgaggaa ctgatgagtc cgggccgc
```

FIGURE 14

Human Interferon-β 1a-MOD-9011

IFNβ 1A-CTP DNA and protein sequence

AA sequence (Accession No. NP_002167.1)

C)
```
M  T  N  K  C  L  L  Q  I  A  L  L  C  F  S  T  T  A  L  S  M  S  Y
N  L  L  G  F  L  Q  R  S  S  N  F  Q  C  Q  K  L  L  W  Q  L  N  G  R
L  E  Y  C  L  K  D  R  M  N  F  D  I  P  E  E  I  K  Q  L  Q  Q  F  Q
K  E  D  A  A  L  T  I  Y  E  M  L  Q  N  I  F  A  I  F  R  Q  D  S  S
S  T  G  W  N  E  T  I  V  E  N  L  L  A  N  V  Y  H  Q  I  N  H  L  K
T  V  L  E  E  K  L  E  K  E  D  F  T  R  G  K  L  M  S  S  L  H  L  K
R  Y  Y  G  R  I  L  H  Y  L  K  A  K  E  Y  S  H  C  A  W  T  I  V  R
V  E  I  L  R  N  F  Y  F  I  N  R  L  T  G  Y  L  R  N  S  S  S  S  K
A  P  P  P  S  L  P  S  P  S  R  L  P  G  P  S  D  T  P  I  L  P  Q
```

Nucleotides Sequence (Accession No. NM_002176)

D)
```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa accgtgctgg aagagaagct ggaaaaggag gacttcacca gggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccggct acctgaggaa cagctccagc agcaaggccc ctccaccttc
601 cctgcccagt ccaagccgac tccctgggcc ctccgataca ccaattctgc cacagtgatg
661 a
```

FIGURE 14

Human Interferon-β 1a-MOD-9012

IFNβ 1A-CTP-CTP DNA and protein sequence

E) AA sequence (Accession No. NP_002167.1)

```
M T N K C L L Q I A L L L C F S T T A L S M S
Y N L L G F L Q R S S N F Q C Q K L L W Q L N
G R L E Y C L K D R M N F D I P E E I K Q L Q
Q F Q K E D A A L T I Y E M L Q N I F A I F R
Q D S S S T G W N E T I V E N L L A N V Y H Q
I N H L K T V L E E K L E K E D F T R G K L M
S S L H L K R Y Y G R I L H Y L K A K E Y S H
C A W T I V R V E I L R N F Y F I N R L T G Y
L R N S S S S K A P P P S L P S P S R L P G P
S D T P I L P Q S S S K A P P P S L P S P S
R L P G P S D T P I L P Q
```

Nucleotides Sequence (Accession No. NM_002176)

F)
```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa accgtgctgg aagagaagct ggaaaaggag gacttcacca ggggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccgct acctgaggaa cagctccagc agcaaggccc ctccaccttc
601 cctgccagt ccaagccgac tccctgggcc ctccgacaca ccaatcctgc cacagagcag
661 ctcctctaag gccctcctc catcctgcc atccctcc cggctgcctg gccctctga
721 caccctatc ctgcctcagt gatgaaggtc tggatccgcg gccgc
```

FIGURE 14

Human Interferon-β 1a-MOD-9013

CTP-IFNβ 1A-CTP-CTP DNA and protein sequence

G) AA sequence (Accession No. NP_002167.1)

M T N K C L L Q I A L L L C F S T T A L S S S
S S K A P P P S L P S P S R L P G P S D T P I
L P Q M S Y N L L G F L Q R S S N F Q C Q K L
L W Q L N G R L E Y C L K D R M N F D I P E E
I K Q L Q Q F Q K E D A A L T I Y E M L Q N I
F A I F R Q D S S S T G W N E T I V E N L L A
N V Y H Q I N H L K T V L E E K L E K E D F T
R G K L M S S L H L K R Y Y G R I L H Y L K A
K E Y S H C A W T I V R V E I L R N F Y F I N
R L T G Y L R N S S S S K A P P P S L P S P S
R L P G P S D T P I L P Q S S S S K A P P P S
L P S P S R L P G P S D T P I L P Q

Nucleotides Sequence (Accession No. NM_002176)

H)
```
  1 tctagaggac atgaccaaca agtgcctgct gcagatcgcc ctgctgctgt gcttcagcac
 61 caccgccctg agcagcagca gctccaaggc cccaccccc agcctgccca gcccagcag
121 actgccaggc cccagcgaca cccccatcct gcccagatg agctacaacc tgctgggctt
181 cctgcagagg tccagcaact tccagtgcca gaagctgctg tggcagctga cggcaggct
241 ggaatactgc ctgaaggaca ggatgaactt cgacatccca gaggaaatca agcagctgca
301 gcagttccag aaggaggacg ccgccctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaacgtg ctggaagaga gctggaaaa
481 ggaggacttc accagggca agctgatgag cagcctgcac ctgaagaggt actacggcag
541 aatcctgcac tacctgaagg ccaaggagta cagccactgc gcctggacca tcgtgagggt
601 ggagatcctg aggaacttct acttcatcaa caggctgacc ggctacctga ggaacagctc
661 cagcagcaag gcccctccac cttccctgcc cagtccaagc cgactccctg ggccctcga
721 cacaccaatc ctgccacaga gcagctcctc taaggcccct cctccatccc tgccatccc
781 ctccggctg cctggccct ctgacacccc tatcctgcct cagtgatgaa ggtctggatc
841 cgcggccgc
```

FIGURE 14

Human Interferon-β 1a-MOD-9014

CTP-IFNB-CTP-IFNB DNA and protein sequence

I) AA sequence (Accession No. NP_000790.2)

M T N K C L L Q I A L L L C F S T T A L S S S
S S K A P P P S L P S P S R L P G P S D T P I
L P Q M S Y N L L G F L Q R S S N F Q C Q K L
L W Q L N G R L E Y C L K D R M N F D I P E E
I K Q L Q Q F Q K E D A A L T I Y E M L Q N I
F A I F R Q D S S S T G W N E T I V E N L L A
N V Y H Q I N H L K T V L E E K L E K E D F T
R G K L M S S L H L K R Y Y G R I L H Y L K A
K E Y S H C A W T I V R V E I L R N F Y F I N
R L T G Y L R N S S S S K A P P P S L P S P S
R L P G P S D T P I L P Q M S Y N L L G F L Q
R S S N F Q C Q K L L W Q L N G R L E Y C L K
D R M N F D I P E E I K Q L Q Q F Q K E D A A
L T I Y E M L Q N I F A I F R Q D S S S T G W
N E T I V E N L L A N V Y H Q I N H L K T V L
E E K L E K E D F T R G K L M S S L H L K R Y
Y G R I L H Y L K A K E Y S H C A W T I V R V
E I L R N F Y F I N R L T G Y L R N

Nucleotides Sequence (Accession No. NM_002176)

J)

```
   1 tctagaggac atgaccaaca agtgcctgct gcagatcgcc ctgctgctgt gcttcagcac
  61 caccgccctg agcagcagca gctccaaggc cccaccccccc agcctgccca gccccagcag
 121 gctgccaggc cccagcgaca cccccatcct gccccagatg agctacaacc tgctgggctt
 181 cctgcagagg tccagcaact tccagtgcca gaaactgctg tggcagctga acggcaggct
 241 ggaatactgc ctgaaggacc ggatgaactt cgacatcccc gaagagatca agcagctgca
 301 gcagttccag aaagaggacg ccgccctgac catctacgag atgctgcaga acatcttcgc
 361 catcttcagg caggacagca gcagcaccgg ctggaacgag accatcgtgg agaacctgct
 421 ggccaacgtg taccaccaga tcaaccacct gaaaaccgtg ctggaagaga agctggaaaa
 481 agaggacttc accaggggca agctgatgag cagcctgcac ctgaagaggt actacggcag
 541 aatcctgcac tacctgaagg ccaaagagta cagccactgc gcctggacca tcgtgagggt
 601 ggagatcctg cggaacttct acttcatcaa caggctgacc ggctacctga ggaacagctc
 661 cagcagcaag gcccctccac cctccctgcc ctccccaagc agactgcccg gaccctccga
 721 cacaccaatt ctgccacaga tgtcctacaa tctgctcgga tttctgcagc gctcctccaa
 781 ctttcagtgt cagaagctcc tctggcagct caatggccgc ctggaatatt gtctgaaaga
 841 cagaatgaat tttgacatcc cagaggaaat taaacagctc cagcagtttc agaaagaaga
 901 tgctgctctc acaatctatg aaatgctcca gaatatcttt gcaatctttc gccaggacag
 961 ctcctccacc gggtggaatg agacaattgt cgagaatctg ctcgccaatg tctatcatca
1021gatcaatcac ctcaagacag tcctcgaaga aaaactcgaa aaagaagatt tcacacgcgg
1081caaactgatg tcctccctgc atctgaagcg ctactatggg cgcatcctgc attatctgaa
1041agctaaagaa tactcccact gtgcttggac aattgtgcgc gtcgagatcc tgagaaactt
1101ttatttcatt aaccgcctga caggatacct gcgcaactga tgaaggtctg gatgcggccg
1161c
```

FIGURE 14

Human Interferon-β 1a-MOD-9015

CTP-IFNβ 1A DNA and protein sequence

K) AA sequence (Accession No. NP_002167.1)

```
M  T  N  K  C  L  L  Q  I  A  L  L  L  C  F  S  T  T  A  L  S  S  S
S  S  K  A  P  P  P  S  L  P  S  P  S  R  L  P  G  P  S  D  T  P  I
L  P  Q  M  S  Y  N  L  L  G  F  L  Q  R  S  S  N  F  Q  C  Q  K  L
L  W  Q  L  N  G  R  L  E  Y  C  L  K  D  R  M  N  F  D  I  P  E  E
I  K  Q  L  Q  Q  F  Q  K  E  D  A  A  L  T  I  Y  E  M  L  Q  N  I
F  A  I  F  R  Q  D  S  S  S  T  G  W  N  E  T  I  V  E  N  L  L  A
N  V  Y  H  Q  I  N  H  L  K  T  V  L  E  E  K  L  E  K  E  D  F  T
R  G  K  L  M  S  S  L  H  L  K  R  Y  Y  G  R  I  L  H  Y  L  K  A
K  E  Y  S  H  C  A  W  T  I  V  R  V  E  I  L  R  N  F  Y  F  I  N
R  L  T  G  Y  L  R  N  *
```

L) Nucleotides Sequence (Accession No. NM_002176)

```
  1 tctagaggac atgaccaaca agtgcctgct gcagatcgcc ctgctgctgt gcttcagcac
 61 caccgccctg agcagcagca gctccaaggc cccaccccc agcctgccca gccccagcag
121 gctgccaggc cccagcgaca cccccatcct gccccagatg agctacaacc tgctgggctt
181 cctgcagagg tccagcaact tccagtgcca gaaactgctg tggcagctga acggcaggct
241 ggaatactgc ctgaaggacc ggatgaactt cgacatcccc gaagagatca agcagctgca
301 gcagttccag aaagaggacg ccgcctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaaccgtg ctggaagaga gctggaaaa
481 agaggacttc accaggggca agctgatgag cagcctgcac ctgaagaggt actacgcag
541 aatcctgcac tacctgaagg ccaaagagta cagccactgc gcctggacca tcgtgagggt
601 ggagatcctg cggaacttct acttcatcaa caggctgacc ggctacctga ggaactgatg
661 agtccgcggc cgc
```

FIGURE 14

Human Interferon-β 1a-MOD-9016

M) CTP-IFNβ 1A-CTP DNA and protein sequence
AA sequence (Accession No. NP_002167.1)

```
M  T  N  K  C  L  L  Q  I  A  L  L  L  C  F  S  T  T  A  L  S  S  S
S  S  K  A  P  P  P  S  L  P  S  P  S  R  L  P  G  P  S  D  T  P  I
L  P  Q  M  S  Y  N  L  L  G  F  L  Q  R  S  S  N  F  Q  C  Q  K  L
L  W  Q  L  N  G  R  L  E  Y  C  L  K  D  R  M  N  F  D  I  P  E  E
I  K  Q  L  Q  Q  F  Q  K  E  D  A  A  L  T  I  Y  E  M  L  Q  N  I
F  A  I  F  R  Q  D  S  S  S  T  G  W  N  E  T  I  V  E  N  L  L  A
N  V  Y  H  Q  I  N  H  L  K  T  V  L  E  E  K  L  E  K  E  D  F  T
R  G  K  L  M  S  S  L  H  L  K  R  Y  Y  G  R  I  L  H  Y  L  K  A
K  E  Y  S  H  C  A  W  T  I  V  R  V  E  I  L  R  N  F  Y  F  I  N
R  L  T  G  Y  L  R  N  S  S  S  K  A  P  P  P  S  L  P  S  P  S
R  L  P  G  P  S  D  T  P  I  L  P  Q  *
```

N) Nucleotides Sequence (Accession No. NM_002176)

```
  1 tctagaggac atgaccaaca agtgcctgct gcagatcgcc ctgctgctgt gcttcagcac
 61 caccgccctg agcagcagca gctccaaggc cccaccccc agcctgccca gcccagcag
121 actgccaggc cccagcgaca cccccatcct gccccagatg agctacaacc tgctgggctt
181 cctgcagagg tccagcaact tccagtgcca gaagctgctg tggcagctga cggcaggct
241 ggaatactgc ctgaaggaca ggatgaactt cgacatccca gaggaaatca gcagctgca
301 gcagttccag aaggaggacg ccgccctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaacggtg ctggaagaga agctggaaaa
481 ggaggacttc accagggcaa agctgatgag cagcctgcac ctgaagaggt actacggcag
541 aatcctgcac tacctgaagg ccaaggagta cagccactgc gcctggacca tcgtgagggt
601 ggagatcctg aggaacttct acttcatcaa caggctgacc ggctacctga ggaacagctc
661 cagcagcaag gcccctccac cttccctgcc cagtccaagc cgactccctg ggccctccga
721 tacaccaatt ctgccacagt gatgaaggtc tggatgcggc cgc
```

FIGURE 14

| Peak ID[a] | GU[b] | Structure[c] | name | Percent from total glycans[e] | | | |
|---|---|---|---|---|---|---|---|
| | | | | Und[d] | NAN1 | ABS | ABS BTG |
| 1[f] | 0.92 | ◆—2AB +bgd | GalNAc | 0.4 | 0.4 | 0.6 | 53.0 |
| 2[f] | 1.02 | ◇—2AB +bgd | galactose | 1.9 | 9.7 | 23.8 | 26.5 |
| * | 1.72 | | | 4.3 | 4.6 | 2.3 | |
| 3 | 1.79 | ◇◆—2AB | Galβ1-3GalNAc | 2.3 | 67.7 | 69.4 | 17.1[h] |
| 4[g] | 2.25 | ★◇—2AB | NeuNAcα2-3Gal | 19.8 | 13.0[h] | | |
| * | 2.57 | | | 1.5 | 1.9 | 1.1 | 1.1 |
| 5 | 2.90 | ★◇◆—2AB | NeuNAcα2-3Galβ1-3GalNAc | 70.6 | | | |
| * | 3.58 | | | 0.6 | 0.7 | 0.6 | |
| 6 | 3.22 | ★◇◆—2AB | Galβ1-3[NeuNAcα2-6]GalNAc | 0.9 | 2.3 | | |
| 7 | 4.42 | ★◇◆—2AB★ | NeuNAcα2-3Galβ1-3[NeuNAcα2-6]GalNAc | 1.8 | | | |

FIG. 23

SEQUENCE LISTING

<160> NUMBER OF SEQ ID NOS: 68

<210> SEQ ID NO 1
<211> LENGTH: 221
<212> TYPE: PRT
<213> ORGANISM: Homo sapiens

<400> SEQUENCE: 1

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Ser Lys Ala Pro Pro Pro Ser Leu Pro Ser Pro Ser
        195                 200                 205

Arg Leu Pro Gly Pro Ser Asp Thr Pro Ile Leu Pro Gln
    210                 215                 220

<210> SEQ ID NO 2
<211> LENGTH: 249
<212> TYPE: PRT
<213> ORGANISM: Homo sapiens

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser

```
            100             105             110
Gln Pro Trp Glu Pro Leu Gln Leu His Val Asp Lys Ala Val Ser Gly
            115             120             125

Leu Arg Ser Leu Thr Thr Leu Leu Arg Ala Leu Gly Ala Gln Lys Glu
    130             135             140

Ala Ile Ser Pro Pro Asp Ala Ala Ser Ala Ala Pro Leu Arg Thr Ile
145             150             155             160

Thr Ala Asp Thr Phe Arg Lys Leu Phe Arg Val Tyr Ser Asn Phe Leu
                165             170             175

Arg Gly Lys Leu Lys Leu Tyr Thr Gly Glu Ala Cys Arg Thr Gly Asp
            180             185             190

Arg Ser Ser Ser Lys Ala Pro Pro Ser Leu Pro Ser Pro Ser
    195             200             205

Arg Leu Pro Gly Pro Ser Asp Thr Pro Ile Leu Pro Gln Ser Ser Ser
    210             215             220

Ser Lys Ala Pro Pro Ser Leu Pro Ser Pro Ser Arg Leu Pro Gly
225             230             235             240

Pro Ser Asp Thr Pro Ile Leu Pro Gln
                245

<210> SEQ ID NO 3
<211> LENGTH: 277
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
1               5               10              15

Leu Ser Leu Pro Leu Gly Leu Pro Val Leu Gly Ser Ser Ser Ser Lys
            20              25              30

Ala Pro Pro Pro Ser Leu Pro Ser Pro Ser Arg Leu Pro Gly Pro Ser
            35              40              45

Asp Thr Pro Ile Leu Pro Gln Ala Pro Pro Arg Leu Ile Cys Asp Ser
    50              55              60

Arg Val Leu Glu Arg Tyr Leu Leu Glu Ala Lys Glu Ala Glu Asn Ile
65              70              75              80

Thr Thr Gly Cys Ala Glu His Cys Ser Leu Asn Glu Asn Ile Thr Val
                85              90              95

Pro Asp Thr Lys Val Asn Phe Tyr Ala Trp Lys Arg Met Glu Val Gly
            100             105             110

Gln Gln Ala Val Glu Val Trp Gln Gly Leu Ala Leu Leu Ser Glu Ala
            115             120             125

Val Leu Arg Gly Gln Ala Leu Leu Val Asn Ser Ser Gln Pro Trp Glu
    130             135             140

Pro Leu Gln Leu His Val Asp Lys Ala Val Ser Gly Leu Arg Ser Leu
145             150             155             160

Thr Thr Leu Leu Arg Ala Leu Gly Ala Gln Lys Glu Ala Ile Ser Pro
                165             170             175

Pro Asp Ala Ala Ser Ala Ala Pro Leu Arg Thr Ile Thr Ala Asp Thr
            180             185             190

Phe Arg Lys Leu Phe Arg Val Tyr Ser Asn Phe Leu Arg Gly Lys Leu
    195             200             205

Lys Leu Tyr Thr Gly Glu Ala Cys Arg Thr Gly Asp Arg Ser Ser Ser
    210             215             220
```

Ser Lys Ala Pro Pro Pro Ser Leu Pro Ser Pro Ser Arg Leu Pro Gly
225                 230                 235                 240

Pro Ser Asp Thr Pro Ile Leu Pro Gln Ser Ser Ser Lys Ala Pro
            245                 250                 255

Pro Pro Ser Leu Pro Ser Pro Ser Arg Leu Pro Gly Pro Ser Asp Thr
            260                 265                 270

Pro Ile Leu Pro Gln
        275

<210> SEQ ID NO 4
<211> LENGTH: 387
<212> TYPE: PRT
<213> ORGANISM: Homo sapiens

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ala Pro Pro
    210                 215                 220

Arg Leu Ile Cys Asp Ser Arg Val Leu Glu Arg Tyr Leu Leu Glu Ala
225                 230                 235                 240

Lys Glu Ala Glu Asn Ile Thr Thr Gly Cys Ala Glu His Cys Ser Leu
                245                 250                 255

Asn Glu Asn Ile Thr Val Pro Asp Thr Lys Val Asn Phe Tyr Ala Trp
            260                 265                 270

Lys Arg Met Glu Val Gly Gln Gln Ala Val Glu Val Trp Gln Gly Leu
        275                 280                 285

Ala Leu Leu Ser Glu Ala Val Leu Arg Gly Gln Ala Leu Leu Val Asn
    290                 295                 300

Ser Ser Gln Pro Trp Glu Pro Leu Gln Leu His Val Asp Lys Ala Val
305                 310                 315                 320

```
Ser Gly Leu Arg Ser Leu Thr Thr Leu Leu Arg Ala Leu Gly Ala Gln
            325                 330                 335

Lys Glu Ala Ile Ser Pro Pro Asp Ala Ala Ser Ala Ala Pro Leu Arg
            340                 345                 350

Thr Ile Thr Ala Asp Thr Phe Arg Lys Leu Phe Arg Val Tyr Ser Asn
            355                 360                 365

Phe Leu Arg Gly Lys Leu Lys Leu Tyr Thr Gly Glu Ala Cys Arg Thr
370                 375                 380

Gly Asp Arg
385

<210> SEQ ID NO 5
<211> LENGTH: 221
<212> TYPE: PRT
<213> ORGANISM: Homo sapiens

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
            20                  25                  30

Ala Pro Pro Pro Ser Leu Pro Ser Pro Ser Arg Leu Pro Gly Pro Ser
        35                  40                  45

Asp Thr Pro Ile Leu Pro Gln Ala Pro Arg Leu Ile Cys Asp Ser
    50                  55                  60

Arg Val Leu Glu Arg Tyr Leu Leu Glu Ala Lys Glu Ala Glu Asn Ile
65                  70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
    130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg
    210                 215                 220

<210> SEQ ID NO 6
<211> LENGTH: 249
<212> TYPE: PRT
<213> ORGANISM: Homo sapiens

<400> SEQUENCE: 6

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
            20                  25                  30
```

Ala Pro Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
 50                  55                  60

Arg Val Leu Glu Arg Tyr Leu Leu Glu Ala Lys Glu Ala Glu Asn Ile
 65                  70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
            115                 120                 125

Val Leu Arg Gly Gln Ala Leu Leu Val Asn Ser Ser Gln Pro Trp Glu
130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
            195                 200                 205

Lys Leu Tyr Thr Gly Glu Ala Cys Arg Thr Gly Asp Arg Ser Ser Ser
            210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
                245

<210> SEQ ID NO 7
<211> LENGTH: 25
<212> TYPE: DNA
<213> ORGANISM: Artificial Sequence
<220> FEATURE:
<223> OTHER INFORMATION: Forward primer for EPO-CTP constructs

<400> SEQUENCE: 7
aatctagagg tcatcatggg ggtgc                                          25

<210> SEQ ID NO 8
<211> LENGTH: 32
<212> TYPE: DNA
<213> ORGANISM: Artificial Sequence
<220> FEATURE:
<223> OTHER INFORMATION: Forward primer for NotI CTP containing
      polypeptide

<400> SEQUENCE: 8
attgcggccg cggatccaga agacctttat tg                                  32

<210> SEQ ID NO 9
<211> LENGTH: 25
<212> TYPE: DNA
<213> ORGANISM: Artificial Sequence
<220> FEATURE:
<223> OTHER INFORMATION: Reverse primer for SspI CTP containing
      polypeptide

<400> SEQUENCE: 9
taaatattgg ggtgtccgag ggccc                                         25

<210> SEQ ID NO 10
<211> LENGTH: 32
<212> TYPE: DNA
<213> ORGANISM: Artificial Sequence
<220> FEATURE:
<223> OTHER INFORMATION: Forward primer for SspI CTP containing
      polypeptide

<400> SEQUENCE: 10
ccaatattac cacaagcccc accacgcctc at                                 32

<210> SEQ ID NO 11
<211> LENGTH: 35
<212> TYPE: DNA
<213> ORGANISM: Artificial Sequence
<220> FEATURE:
<223> OTHER INFORMATION: Reverse primer for NotI CTP containing
      polypeptide

<400> SEQUENCE: 11
tgcggccgcg gatccttatc tgtcccctgt cctgc                              35

<210> SEQ ID NO 12
<211> LENGTH: 17
<212> TYPE: DNA
<213> ORGANISM: Artificial Sequence
<220> FEATURE:
<223> OTHER INFORMATION: Forward primer for EPO-CTP constructs

<400> SEQUENCE: 12
gccctgctgt cggaagc                                                  17

<210> SEQ ID NO 13
<211> LENGTH: 32
<212> TYPE: DNA
<213> ORGANISM: Artificial Sequence
<220> FEATURE:
<223> OTHER INFORMATION: Reverse primer for NotI CTP containing
      polypeptide

<400> SEQUENCE: 13
attgcggccg cggatccaga agacctttat tg                                 32

<210> SEQ ID NO 14
<211> LENGTH: 32
<212> TYPE: DNA
<213> ORGANISM: Artificial Sequence
<220> FEATURE:
<223> OTHER INFORMATION: Reverse primer for EPO-CTP constructs

<400> SEQUENCE: 14
ctttgaggaa gaggagccca ggactgggag gc                                 32

<210> SEQ ID NO 15
<211> LENGTH: 24
<212> TYPE: DNA
<213> ORGANISM: Artificial Sequence
<220> FEATURE:
<223> OTHER INFORMATION: Forward primer for EPO-CTP constructs

<400> SEQUENCE: 15
cctgggctcc tcttcctcaa aggc                                          24

<210> SEQ ID NO 16

```
<211> LENGTH: 17
<212> TYPE: DNA
<213> ORGANISM: Artificial Sequence
<220> FEATURE:
<223> OTHER INFORMATION: Reverse primer for EPO-CTP constructs

<400> SEQUENCE: 16
gcttccgaca gcagggc                                                  17

<210> SEQ ID NO 17
<211> LENGTH: 34
<212> TYPE: PRT
<213> ORGANISM: Artificial Sequence
<220> FEATURE:
<223> OTHER INFORMATION: CTP amino acid sequence

<400> SEQUENCE: 17

Asp Pro Arg Phe Gln Asp Ser Ser Ser Ser Lys Ala Pro Pro Pro Ser
 1               5                  10                  15

Leu Pro Ser Pro Ser Arg Leu Pro Gly Pro Ser Asp Thr Pro Ile Leu
            20                  25                  30

Pro Gln

<210> SEQ ID NO 18
<211> LENGTH: 28
<212> TYPE: PRT
<213> ORGANISM: Artificial Sequence
<220> FEATURE:
<223> OTHER INFORMATION: CTP amino acid sequence

<400> SEQUENCE: 18

Ser Ser Ser Ser Lys Ala Pro Pro Pro Ser Leu Pro Ser Pro Ser Arg
 1               5                  10                  15

Leu Pro Gly Pro Ser Asp Thr Pro Ile Leu Pro Gln
            20                  25

<210> SEQ ID NO 19
<211> LENGTH: 27
<212> TYPE: PRT
<213> ORGANISM: Homo sapiens

<400> SEQUENCE: 19

Met Gly Val His Glu Cys Pro Ala Trp Leu Trp Leu Leu Ser Leu
 1               5                  10                  15

Leu Ser Leu Pro Leu Gly Leu Pro Val Leu Gly
            20                  25

<210> SEQ ID NO 20
<211> LENGTH: 786
<212> TYPE: DNA
<213> ORGANISM: Homo sapiens

<400> SEQUENCE: 20
tctagaggtc atcatggggg tgcacgaatg tcctgcctgg ctgtggcttc tcctgtccct      60
tctgtcgctc cctctgggcc tcccagtcct gggctcctct tcctcaaagg cccctccccc     120
gagccttcca gtccatccc gactcccggg ccctcggac accccaatat taccacaagc      180
cccaccacgc ctcatctgtg acagccgagt cctggagagg tacctcttgg aggccaagga     240
ggccgagaat atcacgacgg gctgtgctga acactgcagc ttgaatgaga atatcactgt     300
cccagacacc aaagttaatt tctatgcctg gaagaggatg gaggtcgggc agcaggccgt     360
agaagtctgg cagggcctgg ccctgctgtc ggaagctgtc ctgcggggcc aggccctgtt     420
```

```
ggtcaactct tcccagccgt gggagcccct gcagctgcat gtggataaag ccgtcagtgg      480
ccttcgcagc ctcaccactc tgcttcgggc tctgggagcc cagaaggaag ccatctcccc      540
tccagatgcg gcctcagctg ctccactccg aacaatcact gctgacactt ccgcaaact       600 cttccgagtc tactccaatt tcctccgggg aaagctgaag ctgtacacag gggaggcctg      660
caggacaggg gacagatcct cttcctcaaa ggcccctccc ccgagccttc caagtccatc      720
ccgactcccg gggccctcgg acaccccgat cctcccacaa taaaggtctt ctggatccgc      780
ggccgc                                                                 786
```

<210> SEQ ID NO 21
<211> LENGTH: 873
<212> TYPE: DNA
<213> ORGANISM: Homo sapiens

<400> SEQUENCE: 21

```
tctagaggtc atcatggggg tgcacgaatg tcctgcctgg ctgtggcttc tcctgtccct       60
tctgtcgctc cctctgggcc tcccagtcct gggctcctct tcctcaaagg cccctccccc      120
gagccttcca gtccatccc gactcccggg gccctcggac accccaatat taccacaagc      180
cccaccacgc ctcatctgtg acagccgagt cctggagagg tacctcttgg aggccaagga      240
ggccgagaat atcacgacgg ctgtgctga cactgcagc ttgaatgaga atatcactgt       300
cccagacacc aaagttaatt tctatgcctg gaagaggatg gaggtcgggc agcaggccgt      360
agaagtctgg cagggcctgg ccctgctgtc ggaagctgtc ctgcggggcc aggccctgtt      420
ggtcaactct tcccagccgt gggagcccct gcagctgcat gtggataaag ccgtcagtgg      480
ccttcgcagc ctcaccactc tgcttcgggc tctgggagcc cagaaggaag ccatctcccc      540
tccagatgcg gcctcagctg ctccactccg aacaatcact gctgacactt ccgcaaact       600 cttccgagtc tactccaatt tcctccgggg aaagctgaag ctgtacacag gggaggcctg      660
caggacaggg gacagatcct cttcctcaaa ggcccctccc ccgagccttc caagtccatc      720
ccgactcccg gggccctcgg acacaccaat cctgccacag agcagctcct ctaaggcccc      780
tcctccatcc ctgccatccc cctcccggct gcctggcccc tctgacaccc ctatcctgcc      840
tcagtgatga aggtcttctg gatccgcggc cgc                                   873
```

<210> SEQ ID NO 22
<211> LENGTH: 221
<212> TYPE: PRT
<213> ORGANISM: Homo sapiens

<400> SEQUENCE: 22

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95
```

```
Leu Ser Glu Ala Val Leu Arg Ser Gln Ala Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                    165                 170                 175

Arg Gly Lys Leu Lys Leu Tyr Thr Gly Glu Ala Cys Arg Thr Gly Asp
                180                 185                 190

Arg Ser Ser Ser Lys Ala Pro Pro Ser Leu Pro Ser Pro Ser
            195                 200                 205

Arg Leu Pro Gly Pro Ser Asp Thr Pro Ile Leu Pro Gln
        210                 215                 220

<210> SEQ ID NO 23
<211> LENGTH: 217
<212> TYPE: PRT
<213> ORGANISM: Homo sapiens

<400> SEQUENCE: 23

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 24
<211> LENGTH: 166
<212> TYPE: PRT
<213> ORGANISM: Homo sapiens
```

<400> SEQUENCE: 24

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 25
<211> LENGTH: 30
<212> TYPE: PRT
<213> ORGANISM: Homo sapiens

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 26
<211> LENGTH: 21
<212> TYPE: PRT
<213> ORGANISM: Homo sapiens

<400> SEQUENCE: 26

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 27
<211> LENGTH: 19
<212> TYPE: DNA
<213> ORGANISM: Artificial Sequence
<220> FEATURE:
<223> OTHER INFORMATION: XbaI Forward primer for HGH-CTP constructs

<400> SEQUENCE: 27
ctctagagga catggccac                                              19

<210> SEQ ID NO 28
<211> LENGTH: 24

```
<212> TYPE: DNA
<213> ORGANISM: Artificial Sequence
<220> FEATURE:
<223> OTHER INFORMATION: Reverse primer for HGH-CTP constructs

<400> SEQUENCE: 28
acagggaggt ctgggggttc tgca                                          24

<210> SEQ ID NO 29
<211> LENGTH: 26
<212> TYPE: DNA
<213> ORGANISM: Artificial Sequence
<220> FEATURE:
<223> OTHER INFORMATION: Forward primer for HGH-CTP constructs

<400> SEQUENCE: 29
tgcagaaccc ccagacctcc ctgtgc                                        26

<210> SEQ ID NO 30
<211> LENGTH: 22
<212> TYPE: DNA
<213> ORGANISM: Artificial Sequence
<220> FEATURE:
<223> OTHER INFORMATION: Reverse primer for HGH-CTP constructs

<400> SEQUENCE: 30
ccaaactcat caatgtatct ta                                            22

<210> SEQ ID NO 31
<211> LENGTH: 19
<212> TYPE: DNA
<213> ORGANISM: Artificial Sequence
<220> FEATURE:
<223> OTHER INFORMATION: XbaI Forward primer for HGH-CTP constructs

<400> SEQUENCE: 31
ctctagagga catggccac                                                19

<210> SEQ ID NO 32
<211> LENGTH: 25
<212> TYPE: DNA
<213> ORGANISM: Artificial Sequence
<220> FEATURE:
<223> OTHER INFORMATION: Reverse primer for HGH-CTP constructs

<400> SEQUENCE: 32
cgaactcctg gtaggtgtca aaggc                                         25

<210> SEQ ID NO 33
<211> LENGTH: 25
<212> TYPE: DNA
<213> ORGANISM: Artificial Sequence
<220> FEATURE:
<223> OTHER INFORMATION: Forward primer for HGH-CTP constructs

<400> SEQUENCE: 33
gcctttgaca cctaccagga gttcg                                         25

<210> SEQ ID NO 34
<211> LENGTH: 33
<212> TYPE: DNA
<213> ORGANISM: Artificial Sequence
<220> FEATURE:
<223> OTHER INFORMATION: NotI Reverse primer for HGH-CTP constructs

<400> SEQUENCE: 34
```

```
acgcggccgc atccagacct tcatcactga ggc                           33
```

<210> SEQ ID NO 35
<211> LENGTH: 34
<212> TYPE: DNA
<213> ORGANISM: Artificial Sequence
<220> FEATURE:
<223> OTHER INFORMATION: Reverse primer for HGH-CTP constructs

<400> SEQUENCE: 35

```
gcggccgcgg actcatcaga agccgcagct gccc                          34
```

<210> SEQ ID NO 36
<211> LENGTH: 217
<212> TYPE: PRT
<213> ORGANISM: Homo sapiens

<400> SEQUENCE: 36

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 37
<211> LENGTH: 245
<212> TYPE: PRT
<213> ORGANISM: Homo sapiens

<400> SEQUENCE: 37

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
```

-continued

```
               35                  40                  45
Leu Ala Phe Asp Thr Tyr Gln Glu Phe Glu Glu Ala Tyr Ile Pro Lys
 50                  55                  60
Glu Gln Lys Tyr Ser Phe Leu Gln Asn Pro Gln Thr Ser Leu Cys Phe
 65                  70                  75                  80
Ser Glu Ser Ile Pro Thr Pro Ser Asn Arg Glu Glu Thr Gln Gln Lys
                 85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Ser Ser Ser Lys Ala Pro
210                 215                 220
Pro Pro Ser Leu Pro Ser Pro Ser Arg Leu Pro Gly Pro Ser Asp Thr
225                 230                 235                 240
Pro Ile Leu Pro Gln
                245
```

<210> SEQ ID NO 38
<211> LENGTH: 273
<212> TYPE: PRT
<213> ORGANISM: Homo sapiens

<400> SEQUENCE: 38

```
Met Ala Thr Gly Ser Arg Thr Ser Leu Leu Leu Ala Phe Gly Leu Leu
  1               5                  10                  15
Cys Leu Pro Trp Leu Gln Glu Gly Ser Ala Phe Pro Thr Ile Pro Leu
                 20                  25                  30
Ser Arg Leu Phe Asp Asn Ala Met Leu Arg Ala His Arg Leu His Gln
             35                  40                  45
Leu Ala Phe Asp Thr Tyr Gln Glu Phe Glu Glu Ala Tyr Ile Pro Lys
 50                  55                  60
Glu Gln Lys Tyr Ser Phe Leu Gln Asn Pro Gln Thr Ser Leu Cys Phe
 65                  70                  75                  80
Ser Glu Ser Ile Pro Thr Pro Ser Asn Arg Glu Glu Thr Gln Gln Lys
                 85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
130                 135                 140
Glu Gly Ile Gln Thr Leu Met Gly Arg Leu Glu Asp Gly Ser Pro Arg
145                 150                 155                 160
```

```
Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
    210                 215                 220

Pro Pro Ser Leu Pro Ser Pro Ser Arg Leu Pro Gly Pro Ser Asp Thr
225                 230                 235                 240

Pro Ile Leu Pro Gln Ser Ser Ser Lys Ala Pro Pro Ser Leu
            245                 250                 255

Pro Ser Pro Ser Arg Leu Pro Gly Pro Ser Asp Thr Pro Ile Leu Pro
            260                 265                 270

Gln

<210> SEQ ID NO 39
<211> LENGTH: 301
<212> TYPE: PRT
<213> ORGANISM: Homo sapiens

<400> SEQUENCE: 39

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255
```

Pro Ser Pro Ser Arg Leu Pro Gly Pro Ser Asp Thr Pro Ile Leu Pro
                260                 265                 270

Gln Ser Ser Ser Lys Ala Pro Pro Ser Leu Pro Ser Pro Ser
        275                 280                 285

Arg Leu Pro Gly Pro Ser Asp Thr Pro Ile Leu Pro Gln
    290                 295                 300

<210> SEQ ID NO 40
<211> LENGTH: 285
<212> TYPE: PRT
<213> ORGANISM: Homo sapiens

<400> SEQUENCE: 40

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Phe Pro Thr Ile Pro Leu Ser Arg Leu Phe
            35                  40                  45

Asp Asn Ala Met Leu Arg Ala His Arg Leu His Gln Leu Ala Phe Asp
    50                  55                  60

Thr Tyr Gln Glu Phe Glu Ala Tyr Ile Pro Lys Glu Gln Lys Tyr
65                  70                  75                  80

Ser Phe Leu Gln Asn Pro Gln Thr Ser Leu Cys Phe Ser Glu Ser Ile
                85                  90                  95

Pro Thr Pro Ser Asn Arg Glu Glu Thr Gln Gln Lys Ser Asn Leu Glu
            100                 105                 110

Leu Leu Arg Ile Ser Leu Leu Leu Ile Gln Ser Trp Leu Glu Pro Val
        115                 120                 125

Gln Phe Leu Arg Ser Val Phe Ala Asn Ser Leu Val Tyr Gly Ala Ser
    130                 135                 140

Asp Ser Asn Val Tyr Asp Leu Leu Lys Asp Leu Glu Glu Gly Ile Gln
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
            180                 185                 190

Ala Leu Leu Lys Asn Tyr Gly Leu Leu Tyr Cys Phe Arg Lys Asp Met
        195                 200                 205

Asp Lys Val Glu Thr Phe Leu Arg Ile Val Gln Cys Arg Ser Val Glu
    210                 215                 220

Gly Ser Cys Gly Phe Ser Ser Ser Lys Ala Pro Pro Pro Ser Leu
225                 230                 235                 240

Pro Ser Pro Ser Arg Leu Pro Gly Pro Ser Asp Thr Pro Ile Leu Pro
                245                 250                 255

Gln Ser Ser Ser Lys Ala Pro Pro Ser Leu Pro Ser Pro Ser
        260                 265                 270

Arg Leu Pro Gly Pro Ser Asp Thr Pro Ile Leu Pro Gln
    275                 280                 285

<210> SEQ ID NO 41
<211> LENGTH: 273
<212> TYPE: PRT
<213> ORGANISM: Homo sapiens

<400> SEQUENCE: 41

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
        20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
        130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
                180                 185                 190

Phe Lys Gln Thr Tyr Ser Lys Phe Asp Thr Asn Ser His Asn Asp Asp
            195                 200                 205

Ala Leu Leu Lys Asn Tyr Gly Leu Leu Tyr Cys Phe Arg Lys Asp Met
        210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255

Pro Ser Pro Ser Arg Leu Pro Gly Pro Ser Asp Thr Pro Ile Leu Pro
            260                 265                 270

Gln

<210> SEQ ID NO 42
<211> LENGTH: 245
<212> TYPE: PRT
<213> ORGANISM: Homo sapiens

<400> SEQUENCE: 42

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
        20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

```
Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
    130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe
            245

<210> SEQ ID NO 43
<211> LENGTH: 12
<212> TYPE: PRT
<213> ORGANISM: Artificial Sequence
<220> FEATURE:
<223> OTHER INFORMATION: CTP amino acid sequence

<400> SEQUENCE: 43

Ser Ser Ser Ser Lys Ala Pro Pro Pro Ser Leu Pro
1               5                   10

<210> SEQ ID NO 44
<211> LENGTH: 853
<212> TYPE: DNA
<213> ORGANISM: Homo sapiens

<400> SEQUENCE: 44
tctagaggac atggccaccg gcagcaggac cagcctgctg ctggccttcg gcctgctgtg      60
cctgccatgg ctgcaggagg cagcgccag ctcttcttct aaggctccac ccccatctct     120
gcccagcccc agcagactgc cgggcccag cgacacaccc attctgcccc agttccccac     180 catcccctg agcaggctgt tcgacaacgc catgctgagg gctcacaggc tgcaccagct     240
ggcctttgac acctaccag agttcgagga agcctacatc cccaaggagc agaagtacag     300
cttcctgcag aaccccaga cctccctgtg cttcagcgag agcatcccca ccccagcaa     360 cagagaggag acccagcaga gagcaacct ggagctgctg aggatctccc tgctgctgat     420
ccagagctgg ctggagcccg tgcagttcct gagaagcgtg ttcgccaaca gcctggtgta     480
cggcgccagc gacagcaacg tgtacgacct gctgaaggac ctggaggagg gcatccagac     540
cctgatgggc cggctggagg acggcagccc caggaccggc cagatcttca agcagaccta     600
cagcaagttc gacaccaaca gccacaacga cgacgccctg ctgaagaact acgggctgct     660
gtactgcttc agaaaggaca tggacaaggt ggagaccttc ctgaggatcg tgcagtgcag     720
aagcgtggag ggcagctgcg gcttcagctc agcagcaag gccccctccc cgagcctgcc     780
ctcccccaag caggctgcctg ggccctccga cacaccaatc ctgcctcagt gatgaaggtc     840
```
tggatgcggc cgc                                                      853

<210> SEQ ID NO 45
<211> LENGTH: 937
<212> TYPE: DNA
<213> ORGANISM: Homo sapiens

<400> SEQUENCE: 45
tctagaggac atggccaccg gcagcaggac cagcctgctg ctggccttcg gcctgctgtg     60
cctgccatgg ctgcaggagg gcagcgccag ctcttcttct aaggctccac ccccatctct    120
gcccagcccc agcagactgc cgggcccag cgacacaccc attctgcccc agttccccac    180
catccccctg agcaggctgt cgacaacgc catgctgagg gctcacaggc tgcaccagct    240
ggcctttgac acctaccagg agttcgagga agcctacatc cccaaggagc agaagtacag    300
cttcctgcag aacccccaga cctccctgtg cttcagcgag agcatcccca ccccagcaa    360
cagagaggag acccagcaga gagcaacct ggagctgctg aggatctccc tgctgctgat    420
ccagagctgg ctggagcccg tgcagttcct gagaagcgtg ttcgccaaca gctggtgta    480
cggcgccagc gacagcaacg tgtacgacct gctgaaggac ctggaggagg catccagac    540
cctgatgggc cggctggagg acggcagccc caggaccggc cagatcttca gcagaccta    600
cagcaagttc gacaccaaca gccacaacga cgacgccctg ctgaagaact acgggctgct    660
gtactgcttc agaaaggaca tggacaaggt ggagaccttc ctgaggatcg tgcagtgcag    720
aagcgtggag ggcagctgcg gcttcagctc cagcagcaag gcccctcccc cgagcctgcc    780
ctccccaagc aggctgcctg ggccctcga cacaccaatc ctgccacaga gcagctcctc    840
taaggcccct cctccatccc tgccatccc ctccggctg cctggcccct ctgacacccc    900
tatcctgcct cagtgatgaa ggtctggatg cggccgc                              937

<210> SEQ ID NO 46
<211> LENGTH: 889
<212> TYPE: DNA
<213> ORGANISM: Homo sapiens

<400> SEQUENCE: 46
tctagaggac atggccaccg gcagcaggac cagcctgctg ctggccttcg gcctgctgtg     60
cctgccatgg ctgcaggagg gcagcgccag ctcttcttct aaggctccac ccccgagcct    120
gcccttcccc accatccccc tgagcaggct gttcgacaac gccatgctga gggctcacag    180
gctgcaccag ctggcctttg acacctacca ggagttcgag gaagcctaca tccccaagga    240
gcagaagtac agcttcctgc agaaccccca gacctccctg tgcttcagcg agagcatccc    300
caccccagc aacagagagg agacccagca gaagagcaac ctggagctgc tgaggatctc    360
cctgctgctg atccagagct ggctggagcc cgtgcagttc ctgagaagcg tgttcgccaa    420
cagcctggtg tacggcgcca gcgacagcaa cgtgtacgac ctgctgaagg acctggagga    480
gggcatccag accctgatgg gccggctgga ggacggcagc cccaggaccg ccagatctt    540
caagcagacc tacagcaagt cgacaccaa cagccacaac gacgacgccc tgctgaagaa    600
ctacgggctg ctgtactgct tcagaaagga catggacaag gtggagacct tcctgaggat    660
cgtgcagtgc agaagcgtgg agggcagctg cggcttcagc tccagcagca aggcccctcc    720
cccgagcctg ccctccccaa gcaggctgcc tgggccctcc gacacaccaa tcctgccaca    780
gagcagctcc tctaaggccc ctcctccatc cctgccatcc cctcccggc tgcctggccc    840
ctctgacacc cctatcctgc ctcagtgatg aaggtctgga tgcggccgc                889

<210> SEQ ID NO 47
<211> LENGTH: 217
<212> TYPE: PRT
<213> ORGANISM: Homo sapiens

<400> SEQUENCE: 47

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 48
<211> LENGTH: 187
<212> TYPE: PRT
<213> ORGANISM: Homo sapiens

<400> SEQUENCE: 48

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

```
Tyr His Gln Ile Asn His Leu Lys Thr Val Leu Glu Glu Lys Leu Glu
            115                 120                 125

Lys Glu Asp Phe Thr Arg Gly Lys Leu Met Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185
```

<210> SEQ ID NO 49
<211> LENGTH: 840
<212> TYPE: DNA
<213> ORGANISM: Homo sapiens

<400> SEQUENCE: 49

```
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat tcctacaaag aagcagcaat   180
tttcagtgtc agaagctcct gtggcaattg aatgggaggc ttgaatactg cctcaaggac   240
aggatgaact tgacatccc tgaggagatt aagcagctgc agcagttcca gaaggaggac   300
gccgcattga ccatctatga gatgctccag aacatctttg ctattttcag acaagattca   360
tctagcactg ctggaatga gactattgtt gagaacctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta acagacttac aggttacctc cgaaactgaa gatctcctag cctgtgcctc   660
tgggactgga caattgcttc aagcattctt caaccagcag atgctgttta agtgactgat   720
ggctaatgta ctgcatatga aaggacacta gaagattttg aaatttttat taaattatga   780
gttattttta tttatttaaa ttttattttg gaaataaat tatttttggt gcaaaagtca   840
```

<210> SEQ ID NO 50
<211> LENGTH: 211
<212> TYPE: PRT
<213> ORGANISM: Homo sapiens

<400> SEQUENCE: 50

```
Thr Phe Leu Gln Pro Phe Glu Ala Phe Ala Leu Ala Gln Gln Val Val
1               5                   10                  15

Gly Asp Thr Val Arg Val Val Asn Met Thr Asn Lys Cys Leu Leu Gln
            20                  25                  30

Ile Ala Leu Leu Leu Cys Phe Ser Thr Thr Ala Leu Ser Met Ser Tyr
        35                  40                  45

Asn Leu Leu Gly Phe Leu Gln Arg Ser Ser Asn Phe Gln Cys Gln Lys
    50                  55                  60

Leu Leu Trp Gln Leu Asn Gly Arg Leu Glu Tyr Cys Leu Lys Asp Arg
65                  70                  75                  80

Met Asn Phe Asp Ile Pro Glu Glu Ile Lys Gln Leu Gln Gln Phe Gln
                85                  90                  95

Lys Glu Asp Ala Ala Leu Thr Ile Tyr Glu Met Leu Gln Asn Ile Phe
```

```
            100                 105                 110
Ala Ile Phe Arg Gln Asp Ser Ser Thr Gly Trp Asn Glu Thr Ile
        115                 120                 125

Val Glu Asn Leu Leu Ala Asn Val Tyr His Gln Ile Asn His Leu Lys
    130                 135                 140

Thr Val Leu Glu Glu Lys Leu Glu Lys Glu Asp Phe Thr Arg Gly Lys
145                 150                 155                 160

Leu Met Ser Ser Leu His Leu Lys Arg Tyr Tyr Gly Arg Ile Leu His
                165                 170                 175

Tyr Leu Lys Ala Lys Glu Tyr Ser His Cys Ala Trp Thr Ile Val Arg
            180                 185                 190

Val Glu Ile Leu Arg Asn Phe Tyr Phe Ile Asn Arg Leu Thr Gly Tyr
        195                 200                 205

Leu Arg Asn
    210

<210> SEQ ID NO 51
<211> LENGTH: 639
<212> TYPE: DNA
<213> ORGANISM: Homo sapiens

<400> SEQUENCE: 51
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat tcctacaaag aagcagcaat   180
tttcagtgtc agaagctcct gtggcaattg aatgggaggc ttgaatactg cctcaaggac   240
aggatgaact tgacatccc tgaggagatt aagcagctgc agcagttcca gaaggaggac   300
gccgcattga ccatctatga tgctccag aacatctttg ctattttcag acaagattca   360
tctagcactg ctggaatga actattgtt gagaacctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta cagacttac aggttacctc cgaaactga                          639

<210> SEQ ID NO 52
<211> LENGTH: 215
<212> TYPE: PRT
<213> ORGANISM: Homo sapiens

<400> SEQUENCE: 52

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95
```

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
            180                 185                 190

Ala Pro Pro Pro Ser Leu Pro Ser Pro Ser Arg Leu Pro Gly Pro Ser
        195                 200                 205

Asp Thr Pro Ile Leu Pro Gln
    210                 215

<210> SEQ ID NO 53
<211> LENGTH: 747
<212> TYPE: DNA
<213> ORGANISM: Homo sapiens

<400> SEQUENCE: 53
acattctaac tgcaaccttt cgaagccttt gctctggcac aacaggtagt aggcgacact      60
gttcgtgttg tcaacatgac caacaagtgt ctcctccaaa ttgctctcct gttgtgcttc     120
tccactacag ctctttccat gagctacaac ttgcttggat tcctacaaag aagcagcaat     180
tttcagtgtc agaagctcct gtggcaattg aatgggaggc ttgaatactg cctcaaggac     240
aggatgaact tgacatccc tgaggagatt aagcagctgc agcagttcca gaaggaggac      300
gccgcattga ccatctatga tgctccag aacatctttg ctattttcag acaagattca       360
tctagcactg gctggaatga gactattgtt gagaacctcc tggctaatgt ctatcatcag     420
ataaaccatc tgaagacagt cctggaagaa aaactggaga agaagatttt caccagggga    480
aaactcatga gcagtctgca cctgaaaaga tattatggga ggattctgca ttacctgaag    540
gccaaggagt acagtcactg tgcctggacc atagtcagag tggaaatcct aaggaacttt    600
tacttcatta acagacttac aggttacctc cgaaactcct cttcctcaaa ggccccctcc    660
ccgagccttc caagtccatc ccgactcccg gggccctcgg acacccgat cctcccacaa      720 taatgaagat ctcctagcct gtgcctc                                        747

<210> SEQ ID NO 54
<211> LENGTH: 243
<212> TYPE: PRT
<213> ORGANISM: Homo sapiens

<400> SEQUENCE: 54

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile

```
                65                  70                  75                  80
Tyr Glu Met Leu Gln Asn Ile Phe Ala Ile Phe Arg Gln Asp Ser Ser
                    85                  90                  95

Ser Thr Gly Trp Asn Glu Thr Ile Val Glu Asn Leu Leu Ala Asn Val
                100                 105                 110

Tyr His Gln Ile Asn His Leu Lys Thr Val Leu Glu Glu Lys Leu Glu
                115                 120                 125

Lys Glu Asp Phe Thr Arg Gly Lys Leu Met Ser Ser Leu His Leu Lys
                130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
                180                 185                 190

Ala Pro Pro Pro Ser Leu Pro Ser Pro Ser Arg Leu Pro Gly Pro Ser
                195                 200                 205

Asp Thr Pro Ile Leu Pro Gln Ser Ser Ser Lys Ala Pro Pro Pro
                210                 215                 220

Ser Leu Pro Ser Pro Ser Arg Leu Pro Gly Pro Ser Asp Thr Pro Ile
225                 230                 235                 240

Leu Pro Gln

<210> SEQ ID NO 55
<211> LENGTH: 831
<212> TYPE: DNA
<213> ORGANISM: Homo sapiens

<400> SEQUENCE: 55
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat tcctacaaag aagcagcaat   180
tttcagtgtc agaagctcct gtggcaattg aatgggaggc ttgaatactg cctcaaggac   240
aggatgaact ttgacatccc tgaggagatt aagcagctgc agcagttcca gaaggaggac   300
gccgcattga ccatctatga gatgctccag aacatctttg ctattttcag acaagattca   360
tctagcactg gctggaatga gactattgtt gagaacctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta cagacttac aggttacctc cgaaactcct cttcctcaaa ggcccctccc   660
ccgagccttc caagtccatc ccgactcccg gggccctcgg acaccccgat cctcccacaa   720
taatcctctt cctcaaaggc ccctcccccg agccttccaa gtccatcccg actcccgggg   780
ccctcggaca ccccgatcct cccacaatga agatctccta gcctgtgcct c            831

<210> SEQ ID NO 56
<211> LENGTH: 271
<212> TYPE: PRT
<213> ORGANISM: Homo sapiens

<400> SEQUENCE: 56

Met Thr Asn Lys Cys Leu Leu Gln Ile Ala Leu Leu Leu Cys Phe Ser
```

```
  1               5                    10                   15
Thr Thr Ala Leu Ser Ser Ser Ser Lys Ala Pro Pro Ser Leu
          20                  25                  30
Pro Ser Pro Ser Arg Leu Pro Gly Pro Ser Asp Thr Pro Ile Leu Pro
              35                  40                  45
Gln Met Ser Tyr Asn Leu Leu Gly Phe Leu Gln Arg Ser Ser Asn Phe
         50                  55                  60
Gln Cys Gln Lys Leu Leu Trp Gln Leu Asn Gly Arg Leu Glu Tyr Cys
 65                  70                  75                  80
Leu Lys Asp Arg Met Asn Phe Asp Ile Pro Glu Glu Ile Lys Gln Leu
                 85                  90                  95
Gln Gln Phe Gln Lys Glu Asp Ala Ala Leu Thr Ile Tyr Glu Met Leu
            100                 105                 110
Gln Asn Ile Phe Ala Ile Phe Arg Gln Asp Ser Ser Ser Thr Gly Trp
            115                 120                 125
Asn Glu Thr Ile Val Glu Asn Leu Leu Ala Asn Val Tyr His Gln Ile
        130                 135                 140
Asn His Leu Lys Thr Val Leu Glu Glu Lys Leu Glu Lys Glu Asp Phe
145                 150                 155                 160
Thr Arg Gly Lys Leu Met Ser Ser Leu His Leu Lys Arg Tyr Tyr Gly
                165                 170                 175
Arg Ile Leu His Tyr Leu Lys Ala Lys Glu Tyr Ser His Cys Ala Trp
            180                 185                 190
Thr Ile Val Arg Val Glu Ile Leu Arg Asn Phe Tyr Phe Ile Asn Arg
        195                 200                 205
Leu Thr Gly Tyr Leu Arg Asn Ser Ser Ser Lys Ala Pro Pro
        210                 215                 220
Ser Leu Pro Ser Pro Ser Arg Leu Pro Gly Pro Ser Asp Thr Pro Ile
225                 230                 235                 240
Leu Pro Gln Ser Ser Ser Lys Ala Pro Pro Ser Leu Pro Ser
            245                 250                 255
Pro Ser Arg Leu Pro Gly Pro Ser Asp Thr Pro Ile Leu Pro Gln
            260                 265                 270
```

<210> SEQ ID NO 57
<211> LENGTH: 915
<212> TYPE: DNA
<213> ORGANISM: Homo sapiens
<400> SEQUENCE: 57

| | | | | | |
|---|---|---|---|---|---|
| acattctaac | tgcaaccttt | cgaagccttt | gctctggcac | aacaggtagt | aggcgacact | 60 |
| gttcgtgttg | tcaacatgac | caacaagtgt | ctcctccaaa | ttgctctcct | gttgtgcttc | 120 |
| tccactacag | ctctttcctc | ctcttcctca | aaggcccctc | cccgagcct | tccaagtcca | 180 |
| tcccgactcc | cggggccctc | ggacaccccg | atcctcccac | aaatgagcta | caacttgctt | 240 |
| ggattcctac | aaagaagcag | caatttcag | tgtcagaagc | tcctgtggca | attgaatggg | 300 |
| aggcttgaat | actgcctcaa | ggacaggatg | aactttgaca | tccctgagga | gattaagcag | 360 |
| ctgcagcagt | tccagaagga | ggacgccgca | ttgaccatct | atgagatgct | ccagaacatc | 420 |
| tttgctattt | tcagacaaga | ttcatctagc | actggctgga | atgagactat | tgttgagaac | 480 |
| ctcctggcta | atgtctatca | tcagataaac | catctgaaga | cagtcctgga | agaaaaactg | 540 |
| gagaaagaag | atttcaccag | ggaaaaactc | atgagcagtc | tgcacctgaa | agatattat | 600 |
| gggaggattc | tgcattacct | gaaggccaag | gagtacagtc | actgtgcctg | gaccatagtc | 660 |

```
agagtggaaa tcctaaggaa cttttacttc attaacagac ttacaggtta cctccgaaac    720
tcctcttcct caaaggcccc tcccccgagc cttccaagtc catcccgact cccggggccc    780
tcggacaccc cgatcctccc acaataatcc tcttcctcaa aggcccctcc cccgagcctt    840
ccaagtccat cccgactccc ggggccctcg acaccccga tcctcccaca atgaagatct     900
cctagcctgt gcctc                                                    915
```

<210> SEQ ID NO 58
<211> LENGTH: 409
<212> TYPE: PRT
<213> ORGANISM: Homo sapiens

<400> SEQUENCE: 58

```
Met Thr Asn Lys Cys Leu Leu Gln Ile Ala Leu Leu Cys Phe Ser
1               5                   10                  15

Thr Thr Ala Leu Ser Ser Ser Ser Lys Ala Pro Pro Ser Leu
            20                  25                  30

Pro Ser Pro Ser Arg Leu Pro Gly Pro Ser Asp Thr Pro Ile Leu Pro
            35                  40                  45

Gln Met Ser Tyr Asn Leu Leu Gly Phe Leu Gln Arg Ser Ser Asn Phe
        50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
        115                 120                 125

Asn Glu Thr Ile Val Glu Asn Leu Leu Ala Asn Val Tyr His Gln Ile
130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
        195                 200                 205

Leu Thr Gly Tyr Leu Arg Asn Ser Ser Ser Lys Ala Pro Pro
            210                 215                 220

Ser Leu Pro Ser Pro Ser Arg Leu Pro Gly Pro Ser Asp Thr Pro Ile
225                 230                 235                 240

Leu Pro Gln Met Ser Tyr Asn Leu Leu Gly Phe Leu Gln Arg Ser Ser
                245                 250                 255

Asn Phe Gln Cys Gln Lys Leu Leu Trp Gln Leu Asn Gly Arg Leu Glu
            260                 265                 270

Tyr Cys Leu Lys Asp Arg Met Asn Phe Asp Ile Pro Glu Glu Ile Lys
        275                 280                 285

Gln Leu Gln Gln Phe Gln Lys Glu Asp Ala Ala Leu Thr Ile Tyr Glu
    290                 295                 300

Met Leu Gln Asn Ile Phe Ala Ile Phe Arg Gln Asp Ser Ser Ser Thr
305                 310                 315                 320
```

```
Gly Trp Asn Glu Thr Ile Val Glu Asn Leu Leu Ala Asn Val Tyr His
                325                 330                 335

Gln Ile Asn His Leu Lys Thr Val Leu Glu Lys Leu Glu Lys Glu
            340                 345                 350

Asp Phe Thr Arg Gly Lys Leu Met Ser Ser Leu His Leu Lys Arg Tyr
                355                 360                 365

Tyr Gly Arg Ile Leu His Tyr Leu Lys Ala Lys Glu Tyr Ser His Cys
            370                 375                 380

Ala Trp Thr Ile Val Arg Val Glu Ile Leu Arg Asn Phe Tyr Phe Ile
385                 390                 395                 400

Asn Arg Leu Thr Gly Tyr Leu Arg Asn
                405

<210> SEQ ID NO 59
<211> LENGTH: 1326
<212> TYPE: DNA
<213> ORGANISM: Homo sapiens

<400> SEQUENCE: 59
acattctaac tgcaaccttt cgaagccttt gctctggcac aacaggtagt aggcgacact      60
gttcgtgttg tcaacatgac caacaagtgt ctcctccaaa ttgctctcct gttgtgcttc    120
tccactacag ctctttcctc ctcttcctca aggcccctc ccccgagcct tccaagtcca     180
tcccgactcc cggggccctc ggacaccccg atcctcccac aaatgagcta caacttgctt    240
ggattcctac aaagaagcag caattttcag tgtcagaagc cctgtggca attgaatggg     300
aggcttgaat actgcctcaa ggacaggatg aactttgaca tccctgagga gattaagcag    360
ctgcagcagt tccagaagga ggacgccgca ttgaccatct atgagatgct ccagaacatc    420
tttgctattt tcagacaaga ttcatctagc actggctgga atgagactat tgttgagaac    480
ctcctggcta atgtctatca tcagataaac catctgaaga cagtcctgga gaaaaactg    540
gagaagaag atttcaccag gggaaaactc atgagcagtc tgcacctgaa agatattat     600
gggaggattc tgcattacct gaaggccaag gagtacagtc actgtgcctg gaccatagtc    660
agagtggaaa tcctaaggaa cttttacttc attaacagac ttacaggtta cctccgaaac    720
tcctcttcct caaaggcccc tccccgagc cttccaagtc atcccgact cccggggccc     780
tcggacaccc cgatcctccc acaaatgagc tacaacttgc ttggattcct acaaagaagc    840
agcaattttc agtgtcagaa gctcctgtgg caattgaatg ggaggcttga atactgcctc    900
aaggacagga tgaactttga catccctgag gagattaagc agctgcagca gttccagaag    960
gaggacgccg cattgaccat ctatgagatg ctccagaaca tctttgctat ttcagacaa   1020
gattcatcta gcactggctg aatgagact attgttgaga acctcctggc taatgtctat   1080
catcagataa accatctgaa gacagtcctg gaagaaaaac tggagaaaga gatttcacc    1140
aggggaaaac tcatgagcag tctgcacctg aaaagatatt atgggaggat tctgcattac    1200
ctgaaggcca aggagtacag tcactgtgcc tggaccatag tcagagtgga aatcctaagg    1260
aacttttact tcattaacag acttacaggt tacctccgaa actgaagatc tcctagcctg    1320
tgcctc                                                              1326

<210> SEQ ID NO 60
<211> LENGTH: 215
<212> TYPE: PRT
<213> ORGANISM: Homo sapiens

<400> SEQUENCE: 60
```

Met Thr Asn Lys Cys Leu Leu Gln Ile Ala Leu Leu Cys Phe Ser
1               5                   10                  15

Thr Thr Ala Leu Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln Met Ser Tyr Asn Leu Leu Gly Phe Leu Gln Arg Ser Ser Asn Phe
50                      55                  60

Gln Cys Gln Lys Leu Leu Trp Gln Leu Asn Gly Arg Leu Glu Tyr Cys
65              70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
            115                 120                 125

Asn Glu Thr Ile Val Glu Asn Leu Leu Ala Asn Val Tyr His Gln Ile
130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
            195                 200                 205

Leu Thr Gly Tyr Leu Arg Asn
210                 215

<210> SEQ ID NO 61
<211> LENGTH: 744
<212> TYPE: DNA
<213> ORGANISM: Homo sapiens

<400> SEQUENCE: 61
acattctaac tgcaaccttt cgaagccttt gctctggcac aacaggtagt aggcgacact      60
gttcgtgttg tcaacatgac caacaagtgt ctcctccaaa ttgctctcct gttgtgcttc    120
tccactacag ctctttcctc ctcttcctca aaggcccctc ccccgagcct tccaagtcca    180
tcccgactcc cggggccctc ggacaccccg atcctcccac aaatgagcta caacttgctt    240
ggattcctac aaagaagcag caattttcag tgtcagaagc tcctgtggca attgaatggg    300
aggcttgaat actgcctcaa ggacaggatg aactttgaca tccctgagga gattaagcag    360
ctgcagcagt tccagaagga ggacgccgca ttgaccatct atgagatgct ccagaacatc    420
tttgctattt tcagacaaga ttcatctagc actggctgga atgagactat tgttgagaac    480
ctcctggcta atgtctatca tcagataaac catctgaaga cagtcctgga agaaaactg     540 gagaagaag atttcaccag gggaaaactc atgagcagtc tgcacctgaa aagatattat    600
gggaggattc tgcattacct gaaggccaag gagtacagtc actgtgcctg gaccatagtc    660
agagtggaaa tcctaaggaa cttttacttc attaacagac ttacaggtta cctccgaaac    720
tgaagatctc ctagcctgtg cctc                                           744

<210> SEQ ID NO 62

```
<211> LENGTH: 243
<212> TYPE: PRT
<213> ORGANISM: Homo sapiens

<400> SEQUENCE: 62

Met Thr Asn Lys Cys Leu Leu Gln Ile Ala Leu Leu Cys Phe Ser
1               5                   10                  15

Thr Thr Ala Leu Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln Met Ser Tyr Asn Leu Leu Gly Phe Leu Gln Arg Ser Ser Asn Phe
    50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
        115                 120                 125

Asn Glu Thr Ile Val Glu Asn Leu Leu Ala Asn Val Tyr His Gln Ile
    130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
        195                 200                 205

Leu Thr Gly Tyr Leu Arg Asn Ser Ser Ser Lys Ala Pro Pro
    210                 215                 220

Ser Leu Pro Ser Pro Ser Arg Leu Pro Gly Pro Ser Asp Thr Pro Ile
225                 230                 235                 240

Leu Pro Gln

<210> SEQ ID NO 63
<211> LENGTH: 828
<212> TYPE: DNA
<213> ORGANISM: Homo sapiens

<400> SEQUENCE: 63
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttcctc ctcttcctca aaggcccctc ccccgagcct tccaagtcca   180
tcccgactcc cggggccctc ggacaccccg atcctccac aaatgagcta caacttgctt   240
ggattcctac aaagaagcag caattttcag tgtcagaagc tcctgtggca attgaatggg   300
aggcttgaat actgcctcaa ggacaggatg aactttgaca tccctgagga gattaagcag   360
ctgcagcagt tccagaagga ggacgccgca ttgaccatct atgagatgct ccagaacatc   420
tttgctattt tcagacaaga ttcatctagc actggctgga atgagactat tgttgagaac   480
ctcctggcta atgtctatca tcagataaac catctgaaga cagtcctgga agaaaaactg   540
```

```
gagaaagaag atttcaccag gggaaaactc atgagcagtc tgcacctgaa aagatattat    600
gggaggattc tgcattacct gaaggccaag gagtacagtc actgtgcctg gaccatagtc    660
agagtggaaa tcctaaggaa cttttacttc attaacagac ttacaggtta cctccgaaac    720
tcctcttcct caaaggcccc tcccccgagc cttccaagtc catcccgact cccggggccc    780
tcggacaccc cgatcctccc acaatgaaga tctcctagcc tgtgcctc                 828
```

<210> SEQ ID NO 64
<211> LENGTH: 21
<212> TYPE: PRT
<213> ORGANISM: Homo sapiens

<400> SEQUENCE: 64

Met Thr Asn Lys Cys Leu Leu Gln Ile Ala Leu Leu Cys Phe Ser
1               5                   10                  15

Thr Thr Ala Leu Ser
            20

<210> SEQ ID NO 65
<211> LENGTH: 23
<212> TYPE: DNA
<213> ORGANISM: Homo sapiens

<400> SEQUENCE: 65
gaattctaga ggacatgacc aac                                            23

<210> SEQ ID NO 66
<211> LENGTH: 33
<212> TYPE: DNA
<213> ORGANISM: Homo sapiens

<400> SEQUENCE: 66
gcggccgcgg actcatcagt tcctcaggta gcc                                 33

<210> SEQ ID NO 67
<211> LENGTH: 12
<212> TYPE: PRT
<213> ORGANISM: Homo sapiens

<400> SEQUENCE: 67

Ser Ser Ser Ser Lys Ala Pro Pro Ser Leu Pro
1               5                   10

<210> SEQ ID NO 68
<211> LENGTH: 166
<212> TYPE: PRT
<213> ORGANISM: Homo sapiens

<400> SEQUENCE: 68

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn

```
                    85                      90                         95
His Leu Lys Thr Val Leu Glu Glu Lys Leu Glu Lys Glu Asp Phe Thr
            100                     105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

LONG-ACTING POLYPEPTIDES AND METHODS OF PRODUCING SAME

CROSS REFERENCE TO RELATED APPLICATIONS

This Application is a divisional of U.S. patent application Ser. No. 13/867,728, filed Apr. 22, 2013, which is a divisional of U.S. patent application Ser. No. 13/191,478, filed Jul. 27, 2011 which is a divisional of U.S. patent application Ser. No. 12/476,916, filed Jun. 2, 2009, which is a continuation-in-part of U.S. patent application Ser. No. 12/401,746, filed Mar. 11, 2009 which is a continuation of U.S. patent application Ser. No. 11/700,910, filed Feb. 1, 2007, which claims priority from U.S. Provisional Application Ser. No. 60/764,761, filed Feb. 3, 2006, all of which are hereby incorporated in their entirety by reference herein.

FIELD OF INVENTION

A polypeptide and polynucleotides encoding same comprising at least three carboxy-terminal peptides (CTP) of chorionic gonadotrophin attached to a cytokine are disclosed. Pharmaceutical compositions comprising the polypeptide and polynucleotides of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administrated by infusion, frequent injection of peptide drugs cause considerable discomfort to a subject. Thus, there is a need for technologies that will prolong the half-lives of therapeutic polypeptides while maintaining a high pharmacological efficacy thereof. Such desirous peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

SUMMARY OF THE INVENTION

In one embodiment, the present invention provides a polypeptide comprising a cytokine, one chorionic gonadotrophin carboxy terminal peptide (CTP) attached to an amino terminus of the cytokine, and two chorionic gonadotrophin carboxy terminal peptides attached to a carboxy terminus of the cytokine.

In another embodiment, the present invention further provides a polynucleotide comprising a coding portion encoding a polypeptide, wherein the polypeptide comprises a cytokine, one chorionic gonadotrophin carboxy terminal peptide (CTP) attached to an amino terminus of the cytokine, and two chorionic gonadotrophin carboxy terminal peptides attached to a carboxy terminus of the cytokine.

In another embodiment, the present invention further provides a method of reducing a dosing frequency of a cytokine, comprising the step of attaching one chorionic gonadotrophin carboxy terminal peptide to an amino terminus of the cytokine and two chorionic gonadotrophin carboxy terminal peptides to a carboxy terminus of the cytokine, thereby reducing a dosing frequency of a cytokine.

In another embodiment, the present invention further provides a method of increasing compliance in the use of cytokine therapy, comprising providing to a subject in need thereof, a polypeptide comprising a cytokine, one chorionic gonadotrophin carboxy terminal peptide (CTP) attached to an amino terminus of the cytokine, and two chorionic gonadotrophin carboxy terminal peptides attached to a carboxy terminus of the cytokine, thereby increasing compliance in the use of cytokine therapy.

In another embodiment, the present invention further provides a method of improving a biological half life of a cytokine, comprising the step of attaching one chorionic gonadotrophin carboxy terminal peptide to an amino terminus of the cytokine and two chorionic gonadotrophin carboxy terminal peptides to a carboxy terminus of the cytokine, thereby improving a biological half life of a cytokine.

In another embodiment, the present invention further provides a method of improving the area under the curve (AUC) of a cytokine, comprising the step of attaching one chorionic gonadotrophin carboxy terminal peptide to an amino terminus of the cytokine and two chorionic gonadotrophin carboxy terminal peptides to a carboxy terminus of the cytokine, thereby improving the area under the curve (AUC) of a cytokine.

BRIEF DESCRIPTION OF THE DRAWINGS

FIGS. 1A-1F are diagrams illustrating six EPO-CTP constructs.

FIG. 1A—is a diagram of the polypeptide of SEQ ID NO: 1.

FIG. 1B is a diagram of the polypeptide of SEQ ID NO: 2.

FIG. 1C is a diagram of the polypeptide of SEQ ID NO: 3.

FIG. 1D is a diagram of the polypeptide of SEQ ID NO: 4.

FIG. 1E is a diagram of the polypeptide of SEQ ID NO: 5.

FIG. 1F is a diagram of the polypeptide of SEQ ID NO: 6.

FIG. 2 is a photograph illustrating the expression of the EPO-CTP variants from transfected DG44 cells. Final test samples from transfected cells were prepared as described under "sample preparation" and run on SDS/PAGE. Proteins were detected by Western blot.

FIG. 14 presents the MOD-9010 amino acid sequence (SEQ ID NO: 48) (A) and nucleic acid sequence (SEQ ID NO: 49) (B); MOD-9011 amino acid sequence (SEQ ID NO: 52) (C) and nucleic acid sequence (SEQ ID NO: 53) (D); MOD-9012 amino acid sequence (SEQ ID NO: 54) (E) and nucleic acid sequence (SEQ ID NO: 55) (F); MOD-9013 amino acid sequence (SEQ ID NO: 56) (G) and nucleic acid sequence (SEQ ID NO: 57) (H); MOD-9014 amino acid sequence (SEQ ID NO: 58) (I) and nucleic acid sequence (SEQ ID NO: 59) (J); MOD-9015 amino acid sequence (SEQ ID NO: 60) (K) and nucleic acid sequence (SEQ ID NO: 61) (L); MOD-9016 amino acid sequence (SEQ ID NO: 62) (M) and nucleic acid sequence (SEQ ID NO: 63) (N) amino acid sequences (AA) followed by DNA sequences. Underline: Signal sequence, Black letters: Mature protein, Italic: CTP unit.

(FIG. 15A) or i.v. (FIG. 15B) administration of IFN-β1a or MOD-9012, and MOD-9013 in SD rats (n=3 per dose/route/timepoint). IFN-β1a serum concentrations were determined using commercial ELISA kit.

FIG. 23 is a glycan analysis. Structural assignments and percentage areas of peaks are based upon HPLC and enzyme array digests.

DETAILED DESCRIPTION OF THE INVENTION

Figure 3:
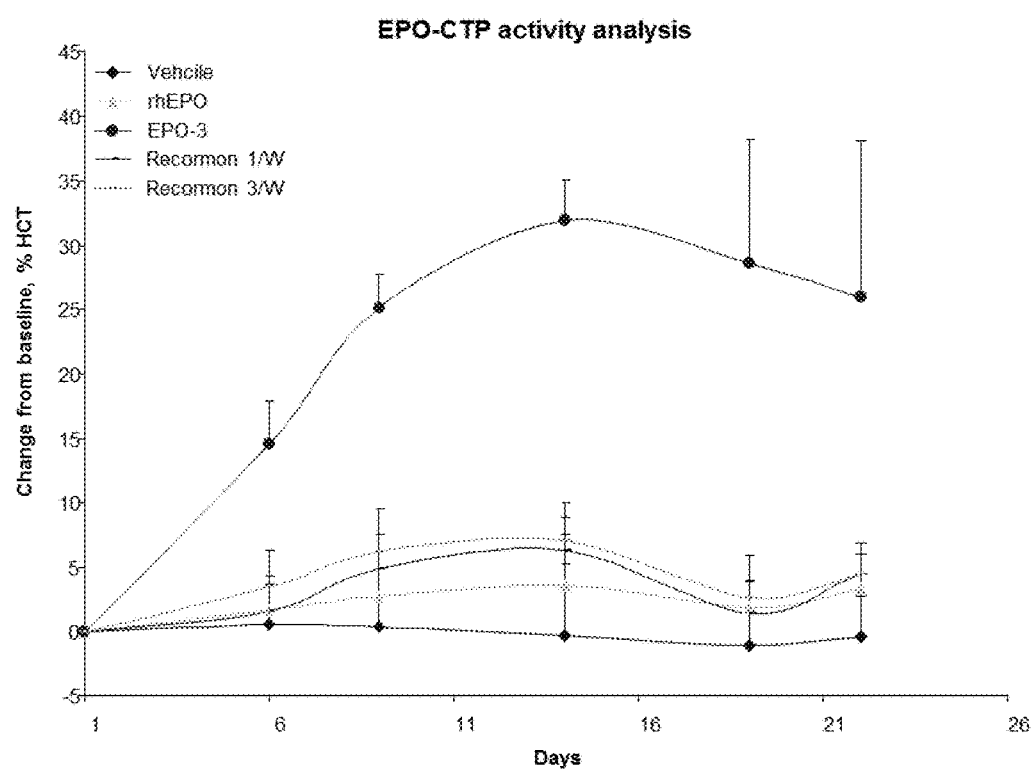
FIG. 3 is a graph illustrating the in vivo bioactivity of recombinant hEPO derivatives and EPO-3 (SEQ ID NO: 3). ICR mice (n=7/group) received a single IV injection/week (15 g/kg) for three weeks of EPO-3, rhEPO-WT (SEQ ID NO: 16), Recormon® (Commercial EPO) or Recormon® (5 µg/kg) 3 times a week. Control animals were injected IV with PBS. Blood samples were collected three times a week and haematocrit levels were detected. Each point represents the group average of haematocrit (%)±SE.

In one embodiment, the present invention provides long-acting cytokines and methods of producing and using same. In another embodiment, long-acting cytokines comprise carboxy terminal peptide (CTP, also referred to as CTP unit). In another embodiment, long-acting polypeptides comprise carboxy terminal peptide (CTP) of human Chorionic Gonadotropin (hCG). In another embodiment, CTP acts as a protectant against degradation of cytokines or polypeptides of interest. In another embodiment, CTP extends the $C_{max}$ of cytokines or polypeptides of interest. In another embodiment, CTP extends the $T_{max}$ of cytokines or polypeptides of interest. In another embodiment, CTP extends circulatory half-lives of cytokines or polypeptides of interest. In some embodiments, CTP enhances the potency of cytokines or polypeptides of interest.

In other embodiments, engineered cytokines or polypeptides of interest of the invention comprising a single CTP attached to the amino terminus and two CTP peptides attached in tandem to the carboxy terminus are at least equivalent to the non CTP modified cytokines or polypeptides of interest, in terms of biological activity. In other embodiments, engineered cytokines or polypeptides of interest of the invention comprising a single CTP attached to the amino terminus and two CTP peptides attached in tandem to the carboxy terminus are at least equivalent to the non CTP modified cytokines or polypeptides of interest, in terms of pharmacological measures such as pharmacokinetics and pharmacodynamics.

In another embodiment, the present invention provides a polypeptide comprising a cytokine and at least one CTP peptide attached to an amino terminus of the cytokine and at least two chorionic gonadotrophin carboxy terminal peptides attached to a carboxy terminus of the cytokine. In another embodiment, the present invention provides a polypeptide comprising one chorionic gonadotrophin carboxy terminal peptide attached to an amino terminus of a cytokine and two chorionic gonadotrophin carboxy terminal peptides attached to a carboxy terminus of a cytokine.

In another embodiment, the terms "CTP peptide," "carboxy terminal peptide" and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, the invention provides a polypeptide consisting a cytokine, a single chorionic gonadotrophin carboxy terminal peptide attached to the amino terminus of the cytokine, and two chorionic gonadotrophin carboxy terminal peptides attached to the carboxy terminus of the cytokine. In another embodiment, the invention provides a polypeptide consisting a cytokine, a single chorionic gonadotrophin carboxy terminal peptide attached to the amino terminus of the cytokine, two chorionic gonadotrophin carboxy terminal peptides attached to the carboxy terminus of the cytokine, and a signal peptide attached to the amino terminus of one chorionic gonadotrophin carboxy terminal peptide.

In another embodiment, a cytokine is a low molecular weight protein. In another embodiment, a cytokine is a protein secreted by a cell. In another embodiment, a cytokine induces and/or regulates an immune response. In another embodiment, a cytokine has a high affinity binding to a specific receptor or receptors. In another embodiment, cytokines as described herein include mimetics of cytokines that can be used to inhibit or potentiate their effects in vivo. In another embodiment, a cytokine comprises an autocrine activity. In another embodiment, a cytokine comprises a paracrine activity. In another embodiment, a cytokine comprises an endocrine activity.

In another embodiment, the cytokine is a Hematopoietin cytokine. In another embodiment, the cytokine is an Interferon cytokine. In another embodiment, the cytokine is a chemokine. In another embodiment, the cytokine is a Tumor Necrosis Factor cytokine. In another embodiment, a cytokine as used herein comprises biological activity and clinical efficacy. In another embodiment, a cytokine as used herein is a therapeutic protein.

In another embodiment, a cytokine comprising CTPs as described herein has enhanced biological activity in vivo compared the same cytokine without CTPs. In another embodiment, a cytokine comprising at least one CTP attached to its amino terminus and at least two CTPs attached to its carboxy terminus has enhanced biological activity in vivo compared the same cytokine without CTPs. In another embodiment, a cytokine comprising one CTP attached to its amino terminus and two CTPs attached to its carboxy terminus has enhanced biological in vivo activity compared the same cytokine in without CTPs.

In another embodiment, a cytokine modified with CTPs is used to facilitate organ transplantation. In another embodiment, a cytokine modified with CTPs is used to reduce inflammation. In another embodiment, a cytokine modified with CTPs is used to induce erythropoiesis. In another embodiment, a cytokine modified with CTPs is used to induce growth. In another embodiment, a cytokine modified with CTPs is used to induce weight gain. In another embodiment, a cytokine modified with CTPs is used in cancer therapy as will be readily understood by one of average skill in the art. In another embodiment, a cytokine modified with CTPs is used to induce an immune response. In another embodiment, a cytokine modified with CTPs is used in infectious disease therapy as will be readily understood by one of average skill in the art. In another embodiment, a cytokine modified with CTPs is used in treating allergy as will be readily understood by one of average skill in the art.

In another embodiment, a subject is a human subject. In another embodiment, a subject is a pet. In another embodiment, a subject is a mammal. In another embodiment, a subject is a farm animal. In another embodiment, a subject is a monkey. In another embodiment, a subject is a horse. In another embodiment, a subject is a cow. In another embodiment, a subject is a mouse. In another embodiment, a subject is a rat.

In another embodiment, a CTP-cytokine-CTP-CTP as described herein comprises a cytokine or an active fragment thereof connected via a peptide bond to at least one CTP unit. In another embodiment, a CTP-cytokine-CTP-CTP as described herein comprises a cytokine or an active fragment thereof connected via a peptide bond to at least one CTP unit which is connected to an additional CTP unit via a peptide bond. In another embodiment, a polypeptide as described herein comprising a cytokine fragments thereof and CTP units and/or fragments thereof are interconnected via a peptide bond. In another embodiment, one nucleic acid molecule encodes a polypeptide as described herein comprising a cytokine and/or fragments thereof and CTP units and/or fragments thereof.

In one embodiment, the cytokine is a homologue. In one embodiment, a homologue also refers to a deletion, insertion, or substitution variant, including an amino acid substitution, thereof and biologically active polypeptide fragments thereof.

In another embodiment, the invention provides a polypeptide consisting a cytokine antagonist, a single chorionic gonadotrophin carboxy terminal peptide attached to the amino terminus of the cytokine antagonist, and two chorionic gonadotrophin carboxy terminal peptides attached to the carboxy terminus of the cytokine antagonist. In another embodiment, the invention provides a polypeptide consisting a cytokine antagonist, a single chorionic gonadotrophin carboxy terminal peptide attached to the amino terminus of the cytokine antagonist, two chorionic gonadotrophin carboxy terminal peptides attached to the carboxy terminus of the cytokine antagonist, and a signal peptide attached to the amino terminus of one chorionic gonadotrophin carboxy terminal peptide.

In another embodiment, a cytokine antagonist modified with CTPs is applied as an anti-cytokine strategy. In another embodiment, a cytokine antagonist modified with CTPs is effective in decrease an inflammatory response. In another embodiment, a cytokine antagonist modified with CTPs is more effective in decreasing an inflammatory response compared to an unmodified cytokine antagonist. In another embodiment, a cytokine antagonist modified with CTPs is more stable than an unmodified cytokine antagonist. In another embodiment, a cytokine antagonist modified with CTPs is more stable in-vivo than an unmodified cytokine antagonist. In another embodiment, a cytokine antagonist modified with CTPs is more bioactive than an unmodified cytokine antagonist.

In another embodiment, a cytokine antagonist is a cytokine homologue. In another embodiment, a cytokine antagonist is a soluble fragment of a cytokine receptor. In another embodiment, a cytokine antagonist is a chemokine receptor homologue.

In another embodiment, a cytokine as described herein is involved in cytokine signaling cascade comprising Ras-MAP kinase pathway. In another embodiment, a cytokine as described herein is involved in induction of JNK. In another embodiment, a cytokine as described herein is involved in induction of p38MAP. In another embodiment, a cytokine as described herein induces cell proliferation. In another embodiment, a cytokine as described herein is involved in cytokine signaling cascade comprising the JAK/STAT pathway. In another embodiment, a cytokine as described herein induces cell growth inhibition. In another embodiment, a cytokine as described herein induces differentiation.

In another embodiment, a cytokine as described herein is a four α-helix bundle cytokine. In another embodiment, a cytokine as described herein is a long-chain 4-helix bundle cytokine. In another embodiment, a cytokine as described herein is a short-chain 4-helix bundle cytokine.

In another embodiment, a cytokine as described herein is a beta-trefoil cytokine. In another embodiment, a cytokine as described herein is a beta-sandwich cytokine. In another embodiment, a cytokine as described herein is an EGF-like cytokine. In another embodiment, a cytokine as described herein comprises a Cystine knot dimerization domain. In another embodiment, a cytokine as described herein comprises both alpha and beta chains. In another embodiment, a cytokine as described herein is an alpha superfamily cytokine such as IL-2, IL-4, IL-5, GM-CSF, IL-3, IFN-alpha, or IL-13. In another embodiment, a cytokine as described herein is a dimeric 4-helix bundles cytokine. In another embodiment, a cytokine as described herein is a member of the IL family of cytokines.

In another embodiment, a cytokine as described herein is a long-chain 4-helix bundle superfamily cytokine such as GH, G-CSF, Myelomonocytic growth factor, IL-6, IL-3, IL-7, LIF, Oncostatin M, Ciliary neurotrophic factor (CNTF), or cholinergic differentiation factor (CDF). In another embodiment, a cytokine as described herein is a short-chain 4-helix bundle superfamily cytokine such as IL-2, IL-4, IL-13, IFN-alpha, IL-5, GM-CSF, L-3, Macrophage colony-stimulating factor (M-CSF). In another embodiment, a cytokine as described herein is a dimeric 4-helix bundles such as IFN-Gamma, IL-10, or IFN-Beta.

In another embodiment, a cytokine as described herein is a Beta-Trefoil cytokine such as IL1-A, IL1-B, or FGF. In another embodiment, a cytokine as described herein is a Beta-sandwich cytokine such as TNF-alpha, or TNF-Beta. In another embodiment, a cytokine as described herein is an EGF-like cytokine such as TGF-Alpha. In another embodiment, a cytokine as described herein comprises cystine knot dimerization domains. In another embodiment, Gonadotropin, Nerve Growth Factor (NGF), Platelet-derived growth factor (PDGF), and TGF-Beta2 comprise cystine knot dimerization domains. In another embodiment, a cytokine as described herein comprises both alpha and beta chains. In another embodiment IL-8, IP10, platelet factor 4 (PF-4), bTG, GRO, 9E3, HLA-A2, macrophage inflammatory protein 1 alpha (MIP-1 alpha), macrophage inflammatory protein 1 beta (MIP-1 beta), and Melanoma growth stimulating activity (MGSA) comprise both alpha and beta chains.

In another embodiment, a cytokine as described herein binds a hematopoietin-receptor family member (also called the class I cytokine receptor family. In another embodiment, a cytokine as described herein binds a class II cytokine receptor (interferons or interferon-like cytokines). In another embodiment, a cytokine as described herein binds a tumor necrosis factor-receptor (TNFR). In another embodiment, a cytokine as described herein binds a, chemokine-receptor. In another embodiment, a cytokine as described herein binds a G protein-coupled receptor.

In another embodiment, a cytokine as described herein is an IL-2 cytokine. In another embodiment, a cytokine as described herein is an interferon. In another embodiment, a cytokine as described herein is an IL-10 cytokine. In another embodiment, a cytokine as described herein is EPO. In another embodiment, a cytokine as described herein is thrombopoietin (THPO). In another embodiment, a cytokine as described herein is IL-1, IL-18, or IL-17). In another embodiment, a cytokine as described herein promotes proliferation of T-cells.

In another embodiment, a cytokine as described herein is a member of the superfamily of growth hormone (GH)-like cytokines. In another embodiment, a cytokine as described herein is close to the cluster formed by ciliary neurotrophic factor and granulocyte colony-stimulating factor (CSF)

In another embodiment, a cytokine as described herein enhances cytokine responses, type 1 (IFN-γ, TGF-β etc.). In another embodiment, a cytokine as described herein enhances antibody responses, type 2 (IL-4, IL-10, IL-13, etc).

In another embodiment, a cytokine is a peptide. In another embodiment, the cytokine is glycosylated. In another embodiment, a cytokine is a polypeptide. In another embodiment, a cytokine as described herein is a modified cytokine comprising at least one CTP peptide attached to an amino terminus of said cytokine and at least two chorionic gonadotrophin carboxy terminal peptides attached to a carboxy terminus of said cytokine. In another embodiment, a cytokine as described herein is a modified cytokine consisting a cytokine, one CTP peptide attached to an amino terminus of the cytokine, and at least two chorionic gonadotrophin carboxy terminal peptides attached to a carboxy terminus of the cytokine. In another embodiment, a cytokine as described herein is a modified cytokine consisting a cytokine, at least one CTP peptide attached to an amino terminus of the cytokine, and two chorionic gonadotrophin carboxy terminal peptides attached to a carboxy terminus of the cytokine. In another embodiment, a cytokine as described herein is a modified cytokine consisting a cytokine, one CTP peptide attached to an amino terminus of the cytokine, and two chorionic gonadotrophin carboxy terminal peptides attached to a carboxy terminus of the cytokine.

In another embodiment, the carboxy-terminal peptide (CTP) is attached to the cytokine via a linker. In another embodiment, the linker which connects the CTP sequence to the cytokine is a covalent bond. In another embodiment, the linker which connects the CTP sequence to the cytokine is a peptide bond. In another embodiment, the linker which connects the CTP sequence to the cytokine is a substituted peptide bond. In another embodiment, the carboxy-terminal peptide (CTP) sequence comprises an amino acid sequence selected from the sequences set forth in SEQ ID NO: 17 and SEQ ID NO: 18.

In another embodiment, SEQ ID NO: 17 comprise the following amino acid (AA) sequence: DPRFQDSSSSKAP-PPSLPSPSRLPGPSDTPILPQ (SEQ ID NO: 17). In another embodiment, SEQ ID NO: 18 comprise the following amino acid (AA) sequence: SSSSKAPPPSLPSPSRLPGPSDT-PILPQ (SEQ ID NO: 18).

In another embodiment, the carboxy terminal peptide (CTP) peptide of the present invention comprises the amino acid sequence from amino acid 112 to position 145 of human chorionic gonadotrophin, as set forth in SEQ ID NO: 17. In another embodiment, the CTP sequence of the present invention comprises the amino acid sequence from amino acid 118 to position 145 of human chorionic gonadotropin, as set forth in SEQ ID NO: 18. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122 which is incorporated herein be reference. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native human CTP DNA sequence or a peptide thereof. In another embodiment, the CTP peptide DNA sequence of the present invention is at least 80% homologous to the native human CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 67. In another embodiment, SEQ ID NO: 67 comprises the following amino acid (AA) sequence: SSSSKAPPPSLP.

In one embodiment, the truncated CTP comprises the first 11 amino acids of SEQ ID NO:43. In one embodiment, the truncated CTP comprises the first 12 amino acids of SEQ ID NO: 67. In one embodiment, the truncated CTP comprises the first 8 amino acids of SEQ ID NO: 67. In one embodiment, the truncated CTP comprises SEQ ID NO: 43. In one embodiment, the truncated CTP comprises the first 14 amino acids of SEQ ID NO: 67. In one embodiment, the truncated CTP comprises the first 6 amino acids of SEQ ID NO: 67. In one embodiment, the truncated CTP comprises the first 5 amino acids of SEQ ID NO: 67.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites.

In another embodiment, at least one carboxy-terminal peptide (CTP) sequence comprises an amino acid sequence selected from the sequences set forth in SEQ ID NO: 17 and SEQ ID NO: 18. In another embodiment, at least one carboxy-terminal peptide (CTP) is truncated.

In another embodiment, the cytokine further comprises a signal peptide for its secretion. In some embodiments, signal sequences include, but are not limited to the endogenous signal sequence for IFN. In some embodiments, signal sequences include, but are not limited to the endogenous signal sequence of any known cytokine. In another embodiment, the polypeptides and methods of the present invention provide a cytokine having additionally a signal peptide of SEQ ID NO: 64 and at least one CTP peptide on the N-terminus and at least one CTP peptide on the C-terminus. In another embodiment, the polypeptides and methods of the present invention provide a cytokine having additionally on the N-terminus the signal peptide of SEQ ID NO: 64 and at least one CTP peptide on the N-terminus and at least two CTP peptides on the C-terminus. In another embodiment, the polypeptides and methods of the present invention provide a cytokine having additionally on the N-terminus the signal peptide of SEQ ID NO: 64 and a single CTP peptide on the N-terminus and two CTP peptides on the C-terminus. In another embodiment, SEQ ID NO: 64 comprise the following amino acid (AA) sequence: MTNKCLLQIALLLCFSTTALS (SEQ ID NO: 64).

In some embodiments, a CTP sequences are attached at both the amino terminal end of a cytokine and at the carboxy terminal end of the cytokine provide enhanced protection against degradation of a cytokine. In another embodiment, at least one CTP sequence is attached at the amino terminal end of a cytokine and two CTP units are attached in the carboxy terminal end of a cytokine provide enhanced protection against clearance. In another embodiment, at least one CTP sequence is attached at the amino terminal end of a cytokine and two CTP units are attached in the carboxy terminal end of a cytokine provide prolonged clearance time. In another embodiment, at least one CTP sequence is attached at the amino terminal end of a cytokine and two CTP units are attached in the carboxy terminal end of a cytokine enhance $C_{max}$ of a cytokine. In another embodiment, at least one CTP sequence is attached at the amino terminal end of a cytokine and two CTP units are attached in the carboxy terminal end of a cytokine enhance $T_{mx}$ of a cytokine. In another embodiment, at least one CTP sequence is attached at the amino terminal end of a cytokine and two CTP units are attached in the carboxy terminal end of a cytokine enhanced T½.

In some embodiments, CTP sequences at both the amino terminal end of a cytokine and at the carboxy terminal end of the cytokine extend the half-life of the attached cytokine. In another embodiment, at least a single CTP sequence at the amino terminal end of a cytokine and at least two CTP sequences at the carboxy terminal end of the cytokine provide extended half-life to the modified cytokine. In another embodiment, a single CTP sequence at the amino terminal end of a cytokine and two CTP sequences at the carboxy terminal end of the cytokine provide extended half-life to the attached cytokine. In another embodiment, a single CTP sequence at the amino terminal end of a cytokine and two CTP sequences in tandem at the carboxy terminal end of the cytokine provide extended half-life to the cytokine.

In some embodiments, a CTP sequence at the amino terminal end of a polypeptide, a CTP sequence at the carboxy terminal end of the cytokine, and at least one additional CTP sequence attached in tandem to the CTP sequence at the carboxy terminus provide enhanced protection against degradation to a cytokine. In some embodiments, a CTP sequence at the amino terminal end of a cytokine, a CTP sequence at the carboxy terminal end of the cytokine, and at least one additional CTP sequence attached in tandem to the CTP sequence at the carboxy terminus extend the half-life of the cytokine. In some embodiments, a CTP sequence at the amino terminal end of a cytokine, a CTP sequence at the carboxy terminal end of the cytokine, and at least one additional CTP sequence attached in tandem to the CTP sequence at the carboxy terminus enhance the biological activity of the cytokine.

In another embodiment, conjugated cytokines of this invention are used in the same manner as unmodified cytokines. In another embodiment, conjugated cytokines of this invention have an increased circulating half-life and plasma residence time, decreased clearance, and increased clinical activity in vivo. In another embodiment, due to the improved properties of the conjugated cytokines as described herein, these conjugates are administered less frequently than unmodified cytokines. In another embodiment, conjugated cytokines as described herein are administered once a week instead of the three times a week for unmodified cytokines. In another embodiment, decreased frequency of administration will result in improved patient compliance leading to improved treatment outcomes, as well as improved patient quality of life. In another embodiment, compared to conventional conjugates of cytokines linked to poly(ethylene glycol) it has been found that conjugates having the molecular weight and linker structure of the conjugates of this invention have an improved potency, improved stability, elevated AUC levels, enhanced circulating half-life. In another embodiment, compared to conventional conjugates of cytokines linked to poly(ethylene glycol) it has been found that EPO having the molecular weight and linker structure of the conjugates of this invention have an improved potency, improved stability, elevated AUC levels, enhanced circulating half-life. In another embodiment, a therapeutically effective amount of a conjugated cytokine is the amount of conjugate necessary for the in vivo measurable expected biological activity. In another embodiment, a therapeutically effective amount of a conjugated EPO is the amount of EPO conjugate necessary for the in biological activity of inducing bone marrow cells to increase production of reticulocytes and red blood cells. In another embodiment, a therapeutically effective amount of a conjugated cytokine is determined according to factors as the exact type of condition being treated, the condition of the patient being treated, as well as the other ingredients in the composition. In another embodiment, a therapeutically effective amount of a conjugated cytokine is 0.01 to 10 µg per kg body weight administered once a week. In another embodiment, a therapeutically effective amount of a conjugated cytokine is 0.1 to 1 µg per kg body weight, administered once a week. In another embodiment, a pharmaceutical composition comprising a conjugated cytokine is formulated at a strength effective for administration by various means to a human patient.

In another embodiment, the cytokine is an interferon. In another embodiment, the IFN amino acid sequence of the present invention is at least 60% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 70% homologous to an IFN sequence set forth in GenBank Accession No. NP_002167.1 as determined using BlastP software of the NCBI using default parameters). In another embodiment, the IFN amino acid sequence of the present invention is at least 80% homologous to an IFN sequence set forth in GenBank Accession No. NP_002167.1 as determined using BlastP software of the NCBI using default parameters). In another embodiment, the IFN amino acid sequence of the present invention is at least 90% homologous to an IFN sequence set forth in GenBank Accession No. NP_002167.1 as determined using BlastP software of the NCBI using default parameters).

In some embodiments, homology according to the present invention also encompasses deletions, insertions, or substitution variants, including an amino acid substitution, thereof and biologically active polypeptide fragments thereof. In one embodiment the substitution variant is one, in which the glutamine in position 65 of hGH is substituted by a valine (SEQ ID NO: 23) [Gellerfors et al., J Pharm Biomed Anal 1989, 7:173-83].

In another embodiment, a cytokine utilized according to the teachings of the present invention exhibits increased potency. In some embodiments, the attachment of CTP sequence to both the amino and carboxy termini of a cytokine results in prolonged in-vivo activity.

In one embodiment, the term "interferon" refers to the mammalian interferon polypeptide (e.g., Type I or Type II. In one embodiment, "interferon" refers to the mammalian interferon polypeptide Type II interferon) which exhibits an interferon activity, e.g. antiviral or antiproliferative activity. In another embodiment, GenBank accession numbers. of non-limiting examples of interferons are listed in Table 1 below. An interferon of the present invention also refers in one embodiment, to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to interferon sequences listed in Table 1 as determined using BlastP software of the NCBI using default parameters). In another embodiment, homolog may also refer to a deletion, insertion, or substitution variant, including an amino acid substitution, thereof and biologically active polypeptide fragments thereof. In some embodiments, additional suitable interferon polypeptides are as known to those of ordinary skill in the art. In some embodiments, the interferon is a Type I or Type II interferon, including those commonly designated as alpha-interferon. In some embodiments, the interferon is beta-interferon. In some embodiments, the interferon is gamma-interferon. In some embodiments, the interferon is omega-interferon. In another embodiment, interferon is subspecie such as of a type I or Type II interferon (e.g. some embodiments, the interferon is a subspecies interferon. In one embodiment, the subspecies interferon (IFN) is IFN-α2a. In one embodiment, the subspecies interferon (IFN) is IFN-α2b. In one embodiment, the subspecies interferon (IFN) is IFN-β1a. In one embodiment, the interferon (IFN) subspecies is IFN-β1b.

In some embodiments, GenBank accession nos. of non-limiting examples of interferons are listed in Table 1 below.

In one embodiment, an interferon of the present invention also refers to a homologue. In one embodiment, interferon amino acid sequence of the present invention is at least 50% homologous to interferon sequences listed in Table 1 as determined using BlastP software of the NCBI using default parameters). In one embodiment, interferon amino acid sequence of the present invention is at least 60% homologous interferon sequences listed in Table 1 as determined using BlastP software of the NCBI using default parameters). In one embodiment, interferon amino acid sequence of the present invention is at least 70% homologous interferon sequences listed in Table 1 as determined using BlastP software of the NCBI using default parameters). In one embodiment, interferon amino acid sequence of the present invention is at least 80% homologous to interferon sequences listed in Table 1 as determined using BlastP software of the NCBI using default parameters). In one embodiment, interferon amino acid sequence of the present invention is at least 90% homologous to interferon sequences listed in Table 1 as determined using BlastP software of the NCBI using default parameters). In one embodiment, interferon amino acid sequence of the present invention is at least 95% homologous interferon sequences listed in Table I as determined using BlastP software of the NCBI using default parameters). In some embodiments, homology according to the present invention also encompasses deletions, insertions, or substitution variants, including an amino acid substitution, thereof and biologically active polypeptide fragments thereof. In one embodiment the cysteine in position 17 of interferon β is substituted by a Serine (SEQ ID NO: 24).

Table 1 below lists examples of interferons with their respective NCBI sequence numbers.

TABLE 1

| Interferon name | NCBI sequence number |
| --- | --- |
| interferon, α 1 | NP_076918.1 |
| interferon, α 10 | NP_002162.1 |
| interferon, α 13 | NP_008831.2 |
| interferon, α 14 | NP_002163.1 |
| interferon, α 16 | NP_002164.1 |
| interferon, α 17 | NP_067091.1 |
| interferon, α 2 | NP_000596.2 |
| interferon, α 21 | NP_002166.1 |
| interferon, α 4 | NP_066546.1 |
| interferon, α 5 | NP_002160.1 |
| interferon, α 6 | NP_066282.1 |
| interferon, α 7 | NP_066401.2 |
| interferon, α 8 | NP_002161.2 |
| interferon, β 1 | NP_002167.1 |
| interferon, ε1 | NP_795372.1 |
| interferon, γ | NP_000610.2 |
| interferon, ε | NP_064509.1 |
| interferon, Ω1 | NP_002168.1 |

In another embodiment, a method of treating or reducing a disease treatable or reducible by a cytokine or a pharmaceutical formulation comprising the same, in a subject, comprises the step of administering to a subject a therapeutically effective amount of the polypeptide comprising a cytokine and CTP units as described herein, thereby treating or reducing a disease treatable or reducible by a cytokine in a subject.

In another embodiment, a method of treating or reducing a disease treatable or reducible by an interferon or a pharmaceutical formulation comprising the same, in a subject, comprises the step of administering to a subject a therapeutically effective amount of the polypeptide comprising IFN protein and CTP units as described herein, thereby treating or reducing a disease treatable or reducible by an interferon in a subject.

In another embodiment, a disease treatable or reducible by an interferon is hepatitis C infection, cancer, bacterial infection, viral infection, injury, multiple sclerosis, hairy cell leukemia, malignant melanoma, Kaposi's sarcoma, bladder cancer, chronic myelocytic leukemia, kidney cancer, carcinoid tumors, non-Hodgkin's lymphoma, ovarian cancer, skin chronic hepatitis C (CHC), condylomata acuminata (CA), chronic hepatitis B, follicular non-Hodgkin's lymphoma, chronic granulomatous disease, *Mycobacterium avium* complex (MAC), pulmonary fibrosis osteoarthritis, and osteoporosis.

In another embodiment, polypeptides of the present invention comprising IFN α-2a as well as pharmaceutical compositions comprising the same are indicated for hairy cell leukemia (HCL), acquired immune deficiency syndrome (AIDS)-related Kaposi's sarcoma (KS), chronic-phase Philadelphia (Ph) chromosome-positive chronic myelogenous leukemia (CML) and chronic hepatitis C (CHC). IFN α-2a dosage varies depending on the indication. In another embodiment, the effectiveness of IFN α2a as an antineoplastic, immunomodulator and antiviral agent has been established.

In another embodiment, polypeptides of the present invention comprising IFN α-2b as well as pharmaceutical compositions comprising the same are indicated for HCL, AIDS-related Kaposi's sarcoma and CHC. It is also indicated for condylomata acuminata (CA), chronic hepatitis B, malignant melanoma and follicular non-Hodgkin's lymphoma. IFN α-2b dosage varies depending on its indication of usage.

In another embodiment, a polypeptide comprising an IFN protein, at least a single CTP attached to its carboxy terminus, and at least a single CTP attached to its amino terminus is used to trigger an immune response. In another embodiment, a polypeptide comprising an IFN protein, a single CTP attached to its amino terminus, and at least two CTP units attached to its carboxy terminus is used to trigger an immune response. In another embodiment, a polypeptide comprising an IFN protein, a single CTP attached to its amino terminus, and two CTP units attached to its carboxy terminus is used to trigger an immune response. In another embodiment, a polypeptide comprising an IFN protein and CTP units is formulated in a pharmaceutical composition that is administered to a subject in need of triggering an immune response.

In another embodiment, a polypeptide comprising an IFN protein and CTP units as described herein is used to trigger an immune response against a viral infection. In another embodiment, a polypeptide comprising an IFN protein and CTP units is formulated in a pharmaceutical composition that is administered to a subject in need of triggering an immune response against a viral infection.

In another embodiment, a polypeptide comprising an IFN β and CTP units as described herein is used to trigger an immune response via the enhancement of activity of lymphocyte cells. In another embodiment, a polypeptide comprising an IFN β and CTP units is formulated in a pharmaceutical composition that is administered to a subject in need of triggering an immune response via the enhancement of activity of lymphocyte cells.

In another embodiment, a polypeptide comprising a cytokine and CTP units as described herein is used as an anti-tumor agent. In another embodiment, a polypeptide comprising an IFN α and CTP units as described herein is used as an anti-tumor agent. In another embodiment, a polypeptide comprising an IFN α and CTP units is formulated in a pharmaceutical composition that is administered to a patient afflicted with cancer.

In another embodiment, a polypeptide comprising an IFN protein and CTP units as described herein is used equivalently to a regular or a recombinant interferon as known to one of average skill in the art. In another embodiment, a polypeptide comprising an IFN protein and CTP units is formulated equivalently to a regular or a recombinant interferon as known to one of average skill in the art.

In another embodiment, a polypeptide comprising a cytokine and CTP units as described herein modulates an immune response. In another embodiment, a polypeptide comprising a cytokine and CTP units as described herein modulates a cellular immune response. In another embodiment, a polypeptide comprising a cytokine and CTP units as described herein modulates an antibody immune response. In another embodiment, a polypeptide comprising a cytokine and CTP units as described herein inhibits an immune response as described herein. In another embodiment, a polypeptide comprising a cytokine and CTP units as described herein trigger an immune response as described herein.

In another embodiment, a polypeptide comprising an IFN inhibits the activity of T-cells, while simultaneously reducing the production cytokines that operate in the inflammatory response to infection and injury. In another embodiment, a polypeptide comprising an IFN protein and CTP units as described herein enhances the activity of T-cells, while simultaneously reducing the production cytokines that operate in the inflammatory response to infection and injury. In another embodiment, a polypeptide comprising an IFN protein and CTP units is formulated in a pharmaceutical composition that is administered to a patient in need of T-cells activity enhancement. In another embodiment, a polypeptide comprising an IFN protein and CTP units is formulated in a pharmaceutical composition that is administered to a patient afflicted with multiple sclerosis. In another embodiment, a polypeptide comprising an IFN protein and CTP units is formulated in a pharmaceutical composition that is administered to a patient afflicted with hepatitis C infection.

In another embodiment, a cytokine is an interferon (IFN). In another embodiment, a cytokine is a type I interferon. In another embodiment, the interferon (IFN) is IFN-α1a. In another embodiment, the interferon (IFN) is IFN-β1a. In another embodiment, the interferon (IFN) is IFN-γ. In another embodiment, an interferon (IFN) as described herein comprises an amino acid sequence as described herein including the sequences provided in FIGS. 14A, 14C, 14E, 14G, 14I, 14K and 14M. In another embodiment, a polypeptide of the invention comprising interferon (IFN) peptide and at least one CTP unit attached to an amino and/or a carboxy terminus of the polypeptide as described herein comprises an amino acid sequence as described herein including the sequences provided in FIGS. 14A, 14C, 14E, 14G, 14I, 14K and 14M. In another embodiment, an interferon (IFN) peptide as described herein comprises an amino acid sequence set forth in SEQ ID NO: 48. In another embodiment, SEQ ID NO: 48 comprises the following amino acid (AA) sequence:

MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRN (SEQ ID NO:

48, Human Interferon-β 1a-MOD-9010).

In another embodiment, an interferon (IFN) peptide as described herein comprises an amino acid sequence of human interferon β1a (hIFN β1a). In another embodiment, an interferon (IFN) peptide as described herein comprises an amino acid sequence set fourth in GenBank Accession No. NP_002167.1

In another embodiment, an interferon (IFN) as described herein is encoded by a nucleotide acid sequence set forth in SEQ ID NO: 49. In another embodiment, SEQ ID NO: 49 comprises the following nucleotide acid (NA) sequence:

(SEQ ID NO: 49, Human Interferon-β 1a-MOD-9010)
tctagaggacatgaccaacaagtgctgctgcagatcgccagtgagtgct tcagcaccaccgccctgagcatgagctacaacctgctgggcttcctgca gaggtccagcaacttccagtgccagaagagctgtggcagtgaacggcag -continued
```
gctggaatactgcctgaaggacaggatgaacttcgacatcccagaggaa atcaagcagagcagcagttccagaaggaggacgccgccagaccatctac gagatgctgcagaacatcttcgccatcttcaggcaggacagcagcagca ccggctggaacgagaccatcgtggagaacctgctggccaacgtgtacca ccagatcaaccacctgaaaaccgtgctggaagagaagaggaaaaggagg acttcaccaggggcaagctgatgagcagcctgcacctgaagaggtacta cggcagaatcctgcactacctgaaggccaaggagtacagccactgcgcc tggaccatcgtgagggtggagatcctgaggaacttctacttcatcaaca ggctgaccggctacctgaggaactgatgagtccgcggccgc.
```

In another embodiment, an interferon (IFN) peptide as described herein is encoded by a nucleic acid (NA) molecule of human interferon β1a (hIFN β1a). In another embodiment, an interferon (IFN) peptide as described herein is encoded by a nucleic acid (NA) molecule comprising a nucleotide acid sequence set fourth in GenBank Accession No. NM_002176.

In another embodiment, an interferon (IFN) peptide as described herein comprises an amino acid sequence set forth in SEQ ID NO: 50. In another embodiment, SEQ ID NO: 50 comprises the following amino acid (AA) sequence:

```
                                    (SEQ ID NO: 50)
TF*LQPFEAFALAQQVVGDTVRVVNMTNKCLLQIALLLCFSTTALSMSYN

LLGFLQRSSNFQCQKLLWQLNGRLEYCLKDRMNFDIPEEIKQLQQFQKED

AALTIYEMLQNIFAIFRQDSSSTGWNETIVENLLANVYHQINHLKTVLEE

KLEKEDFTRGKLMSSLHLKRYYGRILHYLKAKEYSHCAWTIVRVEILRNF

YFINRLTGYLRN.
```

In another embodiment, an interferon (IFN) peptide as described herein is encoded by a nucleotide acid sequence set forth in SEQ ID NO: 51. In another embodiment, SEQ ID NO: 51 comprises the following nucleotide acid (NA) sequence:

```
                                       (SEQ ID NO: 51)
acattctaactgcaacctttcgaagcctttgctctggcacaacaggtagt aggcgacactgttcgtgttgtcaacatgaccaacaagtgtctcctccaaa ttgctctcctgttgtgcttctccactacagctctttccatgagctacaac ttgcttggattcctacaaagaagcagcaattttcagtgtcagaagctcct gtggcaattgaatgggaggcttgaatactgcctcaaggacaggatgaact ttgacatccctgaggagattaagcagctgcagcagttccagaaggaggac gccgcattgaccatctatgagatgctccagaacatctttgctattttcag acaagattcatctagcactggctggaatgagactattgttgagaacctcc tggctaatgtctatcatcagataaaccatctgaagacagtcctggaagaa aaactggagaaagaagatttcaccaggggaaaactcatgagcagtctgca cctgaaaagatattatgggaggattctgcattacctgaaggccaaggagt acagtcactgtgcctggaccatagtcagagtggaaatcctaaggaacttt tacttcattaacagacttacaggttacctccgaaactga.
```

In another embodiment, the cytokine as described herein comprises a cytokine and at least three CTP units. In another embodiment, the polypeptide as described herein comprises an interferon (IFN) peptide and three CTP units. In another embodiment, the cytokine as described herein comprises an interferon (IFN) peptide-CTP polypeptide encoded by an amino acid sequence comprising the amino acid sequence set forth in SEQ ID NO: 52. In another embodiment, SEQ ID NO: 52 comprises the following amino acid (AA) sequence:

```
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRNSSSSKAPPPSLPS

PSRLPGPSDTPILPQ  (SEQ ID NO: 52, MOD-9011).
```

In another embodiment, the cytokine as described herein comprising an interferon (IFN) peptide- and CTP is encoded by a nucleic acid molecule set forth in SEQ ID NO: 53. In another embodiment, SEQ ID NO: 53 comprises the following nucleotide acid (NA) sequence:

```
tctagaggacatgaccaacaagtgctgctgcagatcgccagtgagtgctt cagcaccaccgccctgagcatgagctacaacctgctgggcttcctgcaga ggtccagcaacttccagtgccagaagagctgtggcagtgaacggcaggct ggaatactgcctgaaggacaggatgaacttcgacatcccagaggaaatca agcagagcagcagttccagaaggaggacgccgccagaccatctacgagat gctgcagaacatcttcgccatcttcaggcaggacagcagcagcaccggct ggaacgagaccatcgtggagaacctgctggccaacgtgtaccaccagatc aaccacctgaaaaccgtgctggaagagaagaggaaaaggaggacttcacc aggggcaagctgatgagcagcctgcacctgaagaggtactacggcagaat cctgcactacctgaaggccaaggagtacagccactgcgcctggaccatcg tgagggtggagatcctgaggaacttctacttcatcaacaggctgaccggc tacctgaggaacagtccagcagcaaggcccctccaccttccctgcccagt ccaagccgactccctgggccctccgatacaccaattctgccacagtgatg a  (SEQ ID NO: 53, MOD-9011).
```

In another embodiment, the cytokine as described herein comprises an interferon (IFN) peptide and two CTP units attached to its carboxy terminus. In another embodiment, the polypeptide as described herein comprises an interferon (IFN) peptide—CTP (×2) encoded by an amino acid sequence comprising the amino acid sequence set forth in SEQ ID NO: 54. In another embodiment, SEQ ID NO: 54 comprises the following amino acid (AA) sequence:

```
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRNSSSSKAPPPSLPS

PSRLPGPSDTPILPQSSSSKAPPPSLPSPSRLPGPSDTPILPQ  (SEQ

ID NO: 54, MOD-9012).
```

In another embodiment, the cytokine as described herein comprising an interferon (IFN) peptide and two CTP units attached to its carboxy terminus is encoded by a nucleic acid molecule set forth in SEQ ID NO: 55. In another embodiment, SEQ ID NO: 55 comprises the following nucleotide acid (NA) sequence:

```
                                 (SEQ ID NO: 55, MOD-9012)
tctagaggacatgaccaacaagtgcctgctgcagatcgccagctgagtg cttcagcaccaccgccctgagcatgagctacaacctgctgggcttcctg cagaggtccagcaacttccagtgccagaagagctgtggcagctgaacgg caggctggaatactgcctgaaggacaggatgaacttcgacatcccagag gaaatcaagcagctgcagcagttccagaaggaggacgccgccctgacca tctacgagatgctgcagaacatcttcgccatcttcaggcaggacagcag cagcaccggctggaacgagaccatcgtggagaacctgctggccaacgtg taccaccagatcaaccacctgaaaaccgtgctggaagagaagaggaaaa ggaggacttcaccaggggcaagctgatgagcagcctgcacctgaagagg tactacggcagaatcctgcactacctgaaggccaaggagtacagccact gcgcctggaccatcgtgagggtggagatcctgaggaacttctacttcat caacaggctgaccggctacctgaggaacagaccagcagcaaggcccctc caccttcctgcccagtccaagccgactccagggccaccgacacaccaa tcctgccacagagcagctcctctaaggcccctcctccatccctgccatc ccctcccggctgcctggcccctctgacacccctatcctgcctcagtga tgaaggtaggatccgcggccgc.
```

In another embodiment, the cytokine as described herein comprises an interferon (IFN) peptide, a single CTP unit attached to the IFN's amino terminus, and two CTP units attached to the IFN's carboxy terminus. In another embodiment, the polypeptide as described herein comprises an interferon (IFN) peptide, a single CTP unit attached to the IFN's amino terminus and two CTP units attached in tandem to the IFN's carboxy terminus. In another embodiment, the polypeptide as described herein comprises (from amino to carboxy termini): CTP (×1)—interferon (IFN) peptide—CTP (×2) comprising an amino acid sequence set forth in SEQ ID NO: 56. In another embodiment, SEQ ID NO: 56 comprises the following amino acid (AA) sequence:

```
                                 (SEQ ID NO: 56, MOD-9013)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQSSSSKAP

PPSLPSPSRLPGPSDTPILPQ.
```

In another embodiment, the cytokine as described herein comprising an interferon (IFN) peptide, a single CTP unit attached to the IFN's amino terminus and two CTP units attached to the IFN's carboxy terminus is encoded by a nucleic acid molecule set forth in SEQ ID NO: 57. In another embodiment, SEQ ID NO: 57 comprises the following nucleotide acid (NA) sequence:

```
                                 (SEQ ID NO: 57, MOD-9013)
tctagaggacatgaccaacaagtgctgctgcagatcgccagtgagtgct tcagcaccaccgccctgagcagcagcagctccaaggccccacccccag cctgcccagccccagcagactgccaggccccagcgacacccccatcctg ccccagatgagctacaacctgctgggcttcctgcagaggtccagcaact tccagtgccagaagagctgtggcagtgaacggcaggctggaatactgcc tgaaggacaggatgaacttcgacatcccagaggaaatcaagcagagcag cagttccagaaggaggacgccgccagaccatctacgagatgctgcagaa catcttcgccatcttcaggcaggacagcagcagcaccggctggaacgag accatcgtggagaacctgctggccaacgtgtaccaccagatcaaccacc tgaaaaccgtgctggaagagaagaggaaaaggaggacttcaccaggggc aagctgatgagcagcctgcacctgaagaggtactacggcagaatcctgc actacctgaaggccaaggagtacagccactgcgcctggaccatcgtgag ggtggagatcctgaggaacttctacttcatcaacaggctgaccggctac ctgaggaacagtccagcagcaaggcccctccaccttcctgcccagtcc aagccgactccctgggccaccgacacaccaatcctgccacagagcagct cctctaaggcccctcctccatccctgccatcccctcccggctgcctgg ccctctgacacccctatcctgcctcagtgatgaaggtaggatccgcgg ccgc.
```

In another embodiment, the cytokine as described herein comprises an interferon (IFN) peptide, a single CTP attached to the IFN's amino terminus, and a single CTP located within an IFN coding sequence. In another embodiment, the polypeptide as described herein comprises (from amino to carboxy termini): CTP (×1)-interferon (IFN) peptide (fragment 1)—CTP-interferon (IFN) peptide (fragment 2) comprising an amino acid sequence set forth in SEQ ID NO: 58. In another embodiment, SEQ ID NO: 58 comprises the following amino acid (AA) sequence:

```
                                 (SEQ ID NO: 58, MOD-9014)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQMSYNLLG

FLQRSSNFQCQKLLWQLNGRLEYCLKDRMNFDIPEEIKQLQQFQKEDAAL

TIYEMLQNIFAIFRQDSSSTGWNETIVENLLANVYHQINHLKTVLEEKLE

KEDFTRGKLMSSLHLKRYYGRILHYLKAKEYSHCAWTIVRVEILRNFYFI

NRLTGYLRN.
```

In another embodiment, the cytokine as described herein comprising an interferon (IFN) peptide, a single CTP unit attached to the IFN's amino terminus, and a single CTP unit located within the IFN coding sequence is encoded by a nucleic acid molecule set forth in SEQ ID NO: 59. In another embodiment, SEQ ID NO: 59 comprises the following nucleotide acid (NA) sequence:

(SEQ ID NO: 59, MOD-9014)
tctagaggacatgaccaacaagtgcctgctgcagatcgccagctgagtg cttcagcaccaccgccctgagcagcagcagctccaaggccccaccccccc agcctgcccagcccagcaggctgccaggccccagcgacaccccatcc tgccccagatgagtacaacctgctgggcttcctgcagaggtccagcaac ttccagtgccagaaactgctgtggcagtgaacggcaggctggaatactg cctgaaggaccggatgaacttcgacatccccgaagagatcaagcagctg cagcagttccagaaagaggacgccgccctgaccatctacgagatgctgc agaacatcttcgccatcttcaggcaggacagcagcagcaccggctggaa cgagaccatcgtggagaacctgctggccaacgtgtaccaccagatcaac cacctgaaaaccgtgctggaagagaagaggaaaaagaggacttcaccag gggcaagtgatgagcagcctgcacctgaagaggtactacggcagaatcc tgcactacctgaaggccaaagagtacagccactgcgcctggaccatcgt gagggtggagatcctgcggaacttctacttcatcaacaggctgaccggc tacctgaggaacagctccagcagcaaggcccctccaccaccagccctcc ccaagcagactgcccggaccaccgacacaccaattctgccacagatgtc ctacaatctgctcggatttctgcagcgctcctccaactttcagtgtcag aagctcctaggcagctcaatggccgcctggaatattgtagaaagacaga atgaattttgacatcccagaggaaattaaacagaccagcagtttcgaa agaagatgctgactcacaatctatgaaatgaccagaatatattgcaata ttcgccaggacagctcctccaccgggtggaatgagacaattgtcgaaa tctgctcgccaatgtctatcatcagatcaatcacctcaagacagtcctc gaagaaaaactcgaaaaagaagatttcacacgcggcaaactgatgtcct ccctgcatctgaaggctactatgggcgcatcctgcattatctgaaagct aaagaatactcccactgtgcttggacaattgtgcgcgtcgagatcctga gaaacttttatttcattaaccgcctgacaggatacctgcgcaactgatg aaggtctggatgcggccgc.

In another embodiment, the cytokine as described herein comprises an interferon (IFN) peptide and a single CTP unit attached to its amino terminus. In another embodiment, the polypeptide as described herein comprises an interferon (IFN) peptide—CTP comprising an amino acid sequence set forth in SEQ ID NO: 60. In another embodiment, SEQ ID NO: 60 comprises the following amino acid (AA) sequence:

(SEQ ID NO: 60, MOD-9015)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRN*.

In another embodiment, the polypeptide as described herein comprising an interferon (IFN) peptide—and a single CTP attached to its amino terminus is encoded by a nucleic acid molecule set forth in SEQ ID NO: 61. In another embodiment, SEQ ID NO: 61 comprises the following nucleotide acid (NA) sequence:

(SEQ ID NO: 61, MOD-9015)
tctagaggacatgaccaacaagtgctgctgcagatcgccagtgagtgct tcagcaccaccgccctgagcagcagcagctccaaggccccacccccag cctgcccagccccagcaggctgccaggccccagcgacaccccatcctg ccccagatgagctacaacctgctgggcttcctgcagaggtccagcaact tccagtgccagaaactgctgtggcagtgaacggcaggctggaatactgc ctgaaggaccggatgaacttcgacatccccgaagagatcaagcagagca gcagttccagaaagaggacgccgccagaccatctacgagatgctgcaga acatcttcgccatcttcaggcaggacagcagcagcaccggctggaacga gaccatcgtggagaacctgctggccaacgtgtaccaccagatcaaccac ctgaaaaccgtgctggaagagaagaggaaaaagaggacttcaccagggg caagtgatgagcagcctgcacctgaagaggtactacggcagaatcctgc actacctgaaggccaaagagtacagccactgcgcctggaccatcgtgag ggtggagatcctgcggaacttctacttcatcaacaggctgaccggctac ctgaggaactgatgagtccgcggccgc.

In another embodiment, the polypeptide as described herein comprises an interferon (IFN) peptide, a single CTP unit attached to its amino terminus, and a single CTP unit attached to its carboxy terminus. In another embodiment, the polypeptide as described herein comprises an interferon (IFN) peptide—CTP comprising an amino acid sequence set forth in SEQ ID NO: 62. In another embodiment, SEQ ID NO: 62 comprises the following amino acid (AA) sequence:

(SEQ ID NO: 62, MOD-9016)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQ*.

In another embodiment, the cytokine as described herein comprising an interferon (IFN) peptide, a single CTP unit attached to its amino terminus, and a single CTP unit attached to its carboxy terminus is encoded by a nucleic acid molecule set forth in SEQ ID NO: 63. In another embodiment, SEQ ID NO: 63 comprises the following nucleotide acid (NA) sequence:

(SEQ ID NO: 63, MOD-9016)
tctagaggacatgaccaacaagtgctgctgcagatcgccagtgagtgct tcagcaccaccgccctgagcagcagcagctccaaggccccacccccag cctgcccagccccagcagactgccaggccccagcgacaccccatcctg ccccagatgagctacaacctgctgggcttcctgcagaggtccagcaact tccagtgccagaagagctgtggcagtgaacggcaggctggaatactgcc tgaaggacaggatgaacttcgacatcccagaggaaatcaagcagagcag cagttccagaaggaggacgccgccagaccatctacgagatgctgcagaa catcttcgccatcttcaggcaggacagcagcagcaccggctggaacgag -continued

```
accatcgtggagaacctgctggccaacgtgtaccaccagatcaaccacc tgaaaaccgtgctggaagagaagaggaaaaggaggacttcaccaggggc aagctgatgagcagcctgcacctgaagaggtactacggcagaatcctgc actacctgaaggccaaggagtacagccactgcgcctggaccatcgtgag ggtggagatcctgaggaacttctacttcatcaacaggctgaccggctac ctgaggaacagtccagcagcaaggccctccaccttccctgcccagtcc aagccgactccctgggccaccgatacaccaattctgccacagtgatgaa ggtaggatgcggccgc.
```

In another embodiment, an interferon P3 peptide comprises SEQ ID NO: 6 comprising the following amino acid (AA) sequence:

(SEQ ID NO: 68)
MSYNLLGFLQRSSNFQSQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYGRILHYLKAKEYSHCAWTIVRVEI

LRNFYFINRLTGYLRN.

In another embodiment, the methods of the present invention provide an interferon beta 1 peptide having additionally one CTP amino acid peptide on the N-terminus and two CTP amino acid peptides on the C-terminus for treating or inhibiting multiple sclerosis. In another embodiment, the methods of the present invention provide an interferon beta 1 protein comprising an interferon beta 1 sequence as provided herein for treating diseases such as but not limited to multiple sclerosis, cancer, or viral infections. In another embodiment, the methods of the present invention provide an interferon beta 1 protein comprising an interferon beta 1 sequence as provided herein for treating diseases such as but not limited to multiple sclerosis, cancer, or viral infections. In another embodiment, the methods of the present invention provide an interferon beta 1 peptide set forth in SEQ ID NO: 56 for treating diseases such as but not limited to multiple sclerosis, cancer, or viral infections. In another embodiment, the methods of the present invention provide an interferon beta 1 peptide set forth in SEQ ID NO: 58 for treating diseases such as but not limited to multiple sclerosis, cancer, or viral infections. In another embodiment, the methods of the present invention provide an interferon beta 1 peptide set forth in SEQ ID NO: 60 for treating diseases such as but not limited to multiple sclerosis, cancer, or viral infections. In another embodiment, the methods of the present invention provide an interferon beta 1 peptide set forth in SEQ ID NO: 62 for treating diseases such as but not limited to multiple sclerosis, cancer, or viral infections.

As provided herein, attachment of CTP sequence to both the amino and carboxy termini of the EPO protein results in increased potency at stimulating erythropoiesis (FIGS. 3-5) and (Table 6 of Example 4), as compared to recombinant EPO and other combinations of EPO and CTP. In some embodiments, an EPO attached to three CTP sequences does not impair binding to its receptor as evidenced in Table 4 of Example 3, which demonstrates that EPO attached to three CTP sequences is equally effective at stimulating proliferation of TF-1 cells as wild-type EPO. I In some embodiments, "homology" according to the present invention also encompasses deletions, insertions, or substitution variants, including an amino acid substitution, thereof and biologically active polypeptide fragments thereof. In one embodiment the substitution variant comprises a glycine in position 104 of erythropoietin amino acid sequence is substituted by a serine (SEQ ID NO: 22).

In another embodiment, the methods of the present invention provide an EPO protein having additionally at least one CTP amino acid peptide on the N-terminus and at least one CTP amino acid peptide on the C-terminus for the treatment of anemia. In another embodiment, the methods of the present invention provide an EPO protein having additionally one CTP amino acid peptide on the N-terminus and two CTP amino acid peptides on the C-terminus for the treatment of anemia.

In another embodiment, the methods of the present invention provide an EPO protein set forth in SEQ ID NO: 1 having additionally at least one CTP amino acid peptide on the N-terminus for the treatment of anemia. In another embodiment, the methods of the present invention provide an EPO protein set forth in SEQ ID NO: 1 having additionally at least one CTP amino acid peptide on the N-terminus and at least one additional CTP amino acid peptide on the C-terminus for the treatment of anemia. In another embodiment, the methods of the present invention provide an EPO protein set forth in SEQ ID NO: 2 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 3 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 4 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 5 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 6 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 16 having additionally at least one CTP amino acid peptide on the N-terminus and at least one CTP amino acid peptide on the C-terminus for the treatment of anemia. In another embodiment, the methods of the present invention provide an EPO protein set forth in SEQ ID NO: 22 having additionally at least one CTP amino acid peptide on the N-terminus and at least one CTP amino acid peptide on the C-terminus for the treatment of anemia.

In another embodiment, the methods of the present invention provide a nucleic acid sequence encoding an EPO protein having additionally at least one CTP amino acid peptide on the N-terminus and at least one CTP amino acid peptide on the C-terminus for the treatment of anemia. In another embodiment, the methods of the present invention provide a nucleic acid sequence encoding an EPO protein having additionally one CTP amino acid peptide on the N-terminus and two CTP amino acid peptides on the C-terminus for the treatment of anemia. In another embodiment, the methods of the present invention provide a nucleic acid set forth in SEQ ID NO: 20 encoding an EPO protein and one CTP amino acid peptide on the N-terminus and at least one CTP amino acid peptide on the C-terminus for the treatment of anemia. In another embodiment, the methods of the present invention provide a nucleic acid set forth in SEQ ID NO: 21 encoding an EPO protein and one CTP amino acid peptide on the N-terminus and two CTP amino acid peptides on the C-terminus for the treatment of anemia.

In another embodiment, the methods of the present invention provide an EPO protein having additionally one CTP amino acid peptide on the N-terminus and two CTP amino acid peptides on the C-terminus for inhibiting anemia, for treating or inhibiting tumor-associated anemia for treating or inhibiting tumor hypoxia for treating or inhibiting chronic infections such as HIV, inflammatory bowel disease, or septic episodes, for treating fatigue syndrome following cancer chemotherapy, for improving stem cell engraftment, for increasing the survival rate of a patient with aplastic anemia or myelodysplastic syndrome. In another embodiment, the methods of the present invention provide an EPO protein as set forth in SEQ ID NO: 1, SEQ ID NO: 2, SEQ ID NO: 3, SEQ ID NO: 4, SEQ ID NO: 5, SEQ ID NO: 6, SEQ ID NO: 16 or SEQ ID NO: 22 having additionally one CTP peptide on the N-terminus and two CTP peptides on the C-terminus for inhibiting anemia, for treating or inhibiting tumor-associated anemia for treating or inhibiting tumor hypoxia for treating or inhibiting chronic infections such as HIV, inflammatory bowel disease, or septic episodes, for treating fatigue syndrome following cancer chemotherapy, for improving stem cell engraftment, for increasing the survival rate of a patient with aplastic anemia or myelodysplastic syndrome.

In another embodiment, the methods of the present invention provide a nucleic acid sequence encoding an EPO protein having additionally one CTP peptide on the N-terminus and two CTP amino acid peptides on the C-terminus for inhibiting anemia, for treating or inhibiting tumor-associated anemia for treating or inhibiting tumor hypoxia for treating or inhibiting chronic infections such as HIV, inflammatory bowel disease, or septic episodes, for treating fatigue syndrome following cancer chemotherapy, for improving stem cell engraftment, for increasing the survival rate of a patient with aplastic anemia or myelodysplastic syndrome. In another embodiment, the methods of the present invention provide a nucleic acid set forth in SEQ ID NO: 20, SEQ ID. NO: 21 encoding an EPO protein and one CTP peptide on the N-terminus and two CTP peptides on the C-terminus for inhibiting anemia, for treating or inhibiting tumor-associated anemia, for treating or inhibiting tumor hypoxia, for treating or inhibiting chronic infections such as HIV, inflammatory bowel disease, or septic episodes, for treating fatigue syndrome following cancer chemotherapy, for improving stem cell engraftment, for increasing the survival rate of a patient with aplastic anemia or myelodysplastic syndrome.

In another embodiment, human growth hormone (hGH) is the cytokine as described herein. In another embodiment, CTP-hGH-CTP-CTP constructs of the invention bind adipocytes and stimulates them to break down triglyceride and suppresses their ability to take up and accumulate circulating lipids. In another embodiment, CTP-hGH-CTP-CTP constructs of the invention exert indirect effects mediated primarily by a insulin-like growth factor-I (IGF-I) (as shown in the examples section).

In another embodiment, CTP-hGH-CTP-CTP constructs of the invention stimulate body growth by stimulating the liver and other tissues to secrete IGF-I. In another embodiment, IGF-I stimulates proliferation of chondrocytes, resulting in bone growth.

In another embodiment, CTP-hGH-CTP-CTP constructs of the invention induce metabolic effects on protein, lipid and carbohydrate metabolism. In another embodiment, CTP-hGH-CTP-CTP constructs of the invention have a direct effect. In another embodiment, CTP-hGH-CTP-CTP constructs of the invention have an indirect effect through induction of IGF-I. In another embodiment, CTP-hGH-CTP-CTP constructs include constructs comprising a leader peptide. In another embodiment, CTP-hGH-CTP-CTP constructs include truncated constructs.

In another embodiment, CTP-hGH-CTP-CTP constructs of the invention stimulate protein anabolism in a tissue. In another embodiment, CTP-hGH-CTP-CTP constructs of the invention stimulate amino acid uptake, increased protein synthesis, and decreased oxidation of proteins.

In another embodiment, CTP-hGH-CTP-CTP constructs of the invention stimulate fat metabolism. In another embodiment, CTP-hGH-CTP-CTP constructs of the invention stimulate the utilization of fat by stimulating triglyceride breakdown and oxidation in adipocytes.

In another embodiment, CTP-hGH-CTP-CTP constructs of the invention stimulate carbohydrate metabolism. In another embodiment, CTP-hGH-CTP-CTP constructs of the invention maintain blood glucose within a normal range. In another embodiment, CTP-hGH-CTP-CTP constructs of the invention comprise an anti-insulin activity. In another embodiment, CTP-hGH-CTP-CTP constructs of the invention suppress the abilities of insulin to stimulate uptake of glucose in peripheral tissues and enhance glucose synthesis in the liver. In another embodiment, CTP-hGH-CTP-CTP constructs of the invention stimulate insulin secretion, leading to hyperinsulinemia.

In another embodiment, CTP-hGH-CTP-CTP constructs of the invention are used to compensate for limited or no production of growth hormone in a subject. In another embodiment, CTP-hGH-CTP-CTP constructs of the invention compensate for limited or no production of growth hormone-releasing hormone (GHRH). In another embodiment, CTP-hGH-CTP-CTP constructs of the invention compensate for the increased activity of somatostatin. In another embodiment, CTP-hGH-CTP-CTP constructs of the invention compensate for limited or no production of ghrelin.

In another embodiment, CTP-hGH-CTP-CTP constructs of the invention are used to treat diseases associated with lesions in either the hypothalamus, the pituitary, or in target cells. In another embodiment, CTP-hGH constructs of the invention are used to treat diseases associated with reduced target cell's response to the hormone.

In another embodiment, CTP-hGH-CTP-CTP constructs of the invention are used to treat children with severe growth retardation. In another embodiment, CTP-hGH-CTP-CTP constructs of the invention are used to treat children of pathologically short stature. In another embodiment, CTP-hGH-CTP-CTP constructs of the invention are used to enhance athletic performance. In another embodiment, CTP-hGH-CTP-CTP constructs of the invention are used to treat symptoms of aging. In another embodiment, CTP-hGH constructs of the invention are used to treat cosmetic symptoms of aging.

In another embodiment, CTP-hGH-CTP-CTP constructs of the invention are used for enhancing milk production in a female subject. In another embodiment, CTP-cowGH-CTP-CTP constructs of the invention are used for enhancing milk production in dairy cattle. In another embodiment, CTP-animal-GH-CTP-CTP constructs of the invention are used in animal agriculture technology. In another embodiment, CTP-farm animal-GH-CTP-CTP constructs of the invention are used for enhancing growth of farm animal such as but not limited to pigs.

Figure 11:
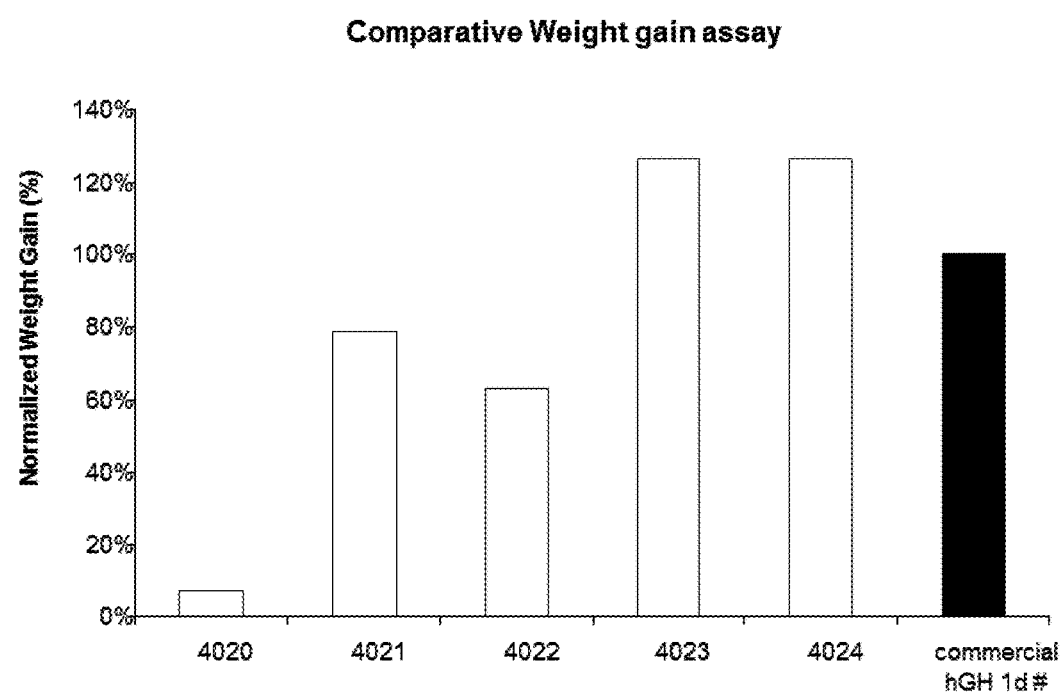
FIG. 11 is a bar graph illustrating the weight gain of hypophysectomized rats following administration of the GH-CTP polypeptides of the present invention.

In some embodiments, human growth hormone (hGH) is utilized according to the teachings of the present invention. In some embodiments, the attachment of CTP sequence to both the amino and carboxy termini of the hGH protein results in increased potency (FIG. 11). In some embodiments, the attachment of CTP sequence to both the amino and carboxy termini of the hGH protein results in prolonged in-vivo activity. In one embodiment, CTP-hGH polypeptides of the present invention are set forth in SEQ ID NO: 39-41.

In one embodiment, the phrase "human growth hormone" (hGH) refers to a polypeptide, such as set forth in Genbank Accession No. P01241 (SEQ ID NO: 47), exhibiting hGH activity (i.e. stimulation of growth).

In one embodiment, "human growth hormone" (hGH) refers to a polypeptide, such as set forth in Genbank Accession No. P01241, exhibiting hGH activity (i.e. stimulation of growth). In one embodiment, hGH of the present invention also refers to homologues. In one embodiment, hGH amino acid sequence of the present invention is at least 50% homologous to an hGH sequence set forth in GenBank Accession No. P01241 as determined using BlastP software of the NCBI using default parameters). In one embodiment, hGH amino acid sequence of the present invention is at least 60% homologous to an hGH sequence set forth in GenBank Accession No. P01241 as determined using BlastP software of the NCBI using default parameters). In one embodiment, hGH amino acid sequence of the present invention is at least 70% homologous to an hGH sequence set forth in GenBank Accession No. P01241 as determined using BlastP software of the NCBI using default parameters). In one embodiment, hGH amino acid sequence of the present invention is at least 80% homologous to an hGH sequence set forth in GenBank Accession No. P01241 as determined using BlastP software of the NCBI using default parameters). In one embodiment, hGH amino acid sequence of the present invention is at least 90% homologous to an hGH sequence set forth in GenBank Accession No. P01241 as determined using BlastP software of the NCBI using default parameters). In one embodiment, hGH amino acid sequence of the present invention is at least 95% homologous to an hGH sequence set forth in GenBank Accession No. P01241 as determined using BlastP software of the NCBI using default parameters).

Exemplary CTP-hGH polypeptides of the present invention are set forth in SEQ ID NO: 39, SEQ ID NO: 40 and SEQ ID NO: 41.

In another embodiment, the methods of the present invention provide a, CTP-hGH-CTP-CTP construct is used for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 23 having additionally at least one CTP amino acid peptide on the N-terminus and at least one CTP amino acid peptide on the C-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 36 having additionally at least one CTP amino acid peptide on the N-terminus and at least one CTP amino acid peptide on the C-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 37 having additionally at least one CTP amino acid peptide on the N-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 38 having additionally at least one CTP amino acid peptide on the N-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 39 for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 40 for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 41 for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein set forth in SEQ ID NO: 42 having additionally at least one CTP amino acid peptide on the N-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide an hGH protein encoded by SEQ ID NO: 44 for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof.

In another embodiment, the methods of the present invention provide a nucleic acid sequence encoding an hGH protein as described herein. In another embodiment, the methods of the present invention provides a nucleic acid of SEQ ID NO: 45 encoding an hGH protein comprising one CTP amino acid peptide on the N-terminus and two CTP amino acid peptides on the C-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof. In another embodiment, the methods of the present invention provide a nucleic acid of SEQ ID NO: 46 encoding an hGH protein and one CTP amino acid peptide on the N-terminus and two CTP amino acid peptides on the C-terminus for stimulating muscle growth, increasing cardiac function, stimulating bone growth, maintaining muscle integrity, balancing muscle metabolism, inducing muscle buildup, inducing de-novo muscle build-up, enhancing bone load, treating symptoms associated with osteoporosis, treating a wasting disease, increasing lipolysis, improving fluid balance, treating osteoporosis, improving lung function, improving immunity, regrowing a vital organ, increasing sense of well-being, restoring REM sleep, or any combination thereof In some embodiments, glucagon-like peptide-1 is utilized according to the teachings of the present invention. In some embodiments, the attachment of CTP sequences to both the amino and carboxy termini of a "glucagon-like peptide-1" results in increased potency. In some embodiments, the attachment of CTP to both the amino and carboxy termini of a peptide results in prolonged in-vivo activity. In some embodiments, the attachment of CTP to both the amino and carboxy termini of the glucagon-like peptide-results in prolonged in-vivo activity.

In one embodiment, "glucagon-like peptide-1" (GLP-1) refers to a mammalian polypeptide. In one embodiment, "glucagon-like peptide-1" (GLP-1) refers to a human polypeptide. In some embodiments, GLP-1 is cleaved from the glucagon preproprotein (Genbank ID No. NP002045) that has the ability to bind to the GLP-1 receptor and initiate a signal transduction pathway resulting in insulinotropic activity. In one embodiment, "insulinotropic activity" refers to the ability to stimulate insulin secretion in response to elevated glucose levels, thereby causing glucose uptake by cells and decreased plasma glucose levels. In some embodiments, GLP-1 polypeptides include, but are not limited to those described in U.S. Pat. No. 5,118,666; which is incorporated by reference herein.

In one embodiment, "GLP-1" refers to a polypeptide, such as set forth in sequences set forth in SEQ ID NO: 25 as determined using BlastP software of the NCBI using default parameters). In one embodiment, a GLP-1 of the present invention also refers to a GLP-1 homologue. In one embodiment, GLP-1 amino acid sequence of the present invention is at least 50% homologous to GLP-1 sequences set forth in SEQ ID NO: 25 as determined using BlastP software of the NCBI using default parameters). In one embodiment, GLP-1 amino acid sequence of the present invention is at least 60% homologous to GLP-1 sequences set forth in SEQ ID NO: 25 as determined using BlastP software of the National Center of Biotechnology Information (NCBI) NCBI using default parameters). In one embodiment, GLP-1 amino acid sequence of the present invention is at least 70% homologous to GLP-1 sequences set forth in SEQ ID NO: 25 as determined using BlastP software of the NCBI using default parameters). In one embodiment, GLP-1 amino acid sequence of the present invention is at least 80% homologous to GLP-1 sequences set forth in SEQ ID NO: 25 as determined using BlastP software of the NCBI using default parameters). In one embodiment, GLP-1 amino acid sequence of the present invention is at least 90% homologous to GLP-1 sequences set forth in SEQ ID NO: 25 as determined using BlastP software of the NCBI using default parameters). In one embodiment, GLP-1 amino acid sequence of the present invention is at least 95% homologous to GLP-1 sequences set forth in SEQ ID NO: 25 as determined using BlastP software of the NCBI using default parameters).

In another embodiment, the methods of the present invention provides a GLP-1 peptide having additionally at least one CTP amino acid peptide on the N-terminus and at least one CTP amino acid peptide on the C-terminus for treating or inhibiting type II diabetes. In another embodiment, the methods of the present invention provides a GLP-1 peptide having additionally one CTP amino acid peptide on the N-terminus and two CTP amino acid peptides on the C-terminus for treating or inhibiting type II diabetes. In another embodiment, the methods of the present invention provides a GLP-1 peptide set forth in SEQ ID NO: 25 having additionally at least one CTP amino acid peptide on the N-terminus and at least one CTP amino acid peptide on the C-terminus for treating or inhibiting type II diabetes.

In another embodiment the polypeptide sequence-of-interest is an insulin-like growth factor. In another embodiment the polypeptide sequence-of-interest is an epidermal growth factor. In another embodiment the polypeptide sequence-of-interest is an acidic or basic fibroblast growth factor. In another embodiment the polypeptide sequence-of-interest is a platelet-derived growth factor. In another embodiment the polypeptide sequence-of-interest is a granulocyte-CSF. In another embodiment the polypeptide sequence-of-interest is a macrophage-CSF. In another embodiment the polypeptide sequence-of-interest is an IL-2. In another embodiment the polypeptide sequence-of-interest is an IL-3. In another embodiment the polypeptide sequence-of-interest is a tumor necrosis factor. In another embodiment the polypeptide sequence-of-interest is an LHRH. In another embodiment the polypeptide sequence-of-interest is an LHRH analog. In another embodiment the polypeptide sequence-of-interest is a somatostatin. In another embodiment the polypeptide sequence-of-interest is a growth hormone releasing factor. In another embodiment the polypeptide sequence-of-interest is an endorphin. In another embodiment the polypeptide sequence-of-interest is an alveolar surfactant protein. In another embodiment the polypeptide sequence-of-interest is a natriuretic factor. In another embodiment the polypeptide sequence-of-interest is an adhesion. In another embodiment the polypeptide sequence-of-interest is an angiostatin. In another embodiment the polypeptide sequence-of-interest is an endostatin. In another embodiment the polypeptide sequence-of-interest is a receptor peptide. In another embodiment the polypeptide sequence-of-interest is a receptor binding ligand. In another embodiment the polypeptide sequence-of-interest is an antibody. In another embodiment the polypeptide sequence-of-interest is an antibody fragment. In another embodiment the polypeptide sequence-of-interest is a peptide or a protein including any modified form.

In another embodiment, the polypeptide of the invention comprises a cytokine having additionally at least one CTP amino acid peptide on the N-terminus and one CTP amino acid peptide on the C-terminus. In another embodiment, the cytokine having additionally at least one CTP amino acid peptide on the N-terminus and two CTP amino acid peptides on the C-terminus is selected from lymphokines, monokines, chemokine, and interleukin. In another embodiment, the cytokine comprises an autocrine action activity. In another embodiment, the cytokine comprises a paracrine action activity. In another embodiment, the cytokine comprises an endocrine action activity.

In another embodiment, the methods of the present invention provide insulin having additionally at least one CTP amino acid peptide on the N-terminus and one CTP amino acid peptide on the C-terminus for the treatment of diabetes.

In another embodiment, the methods of the present invention provide albumin having additionally at least one CTP amino acid peptide on the N-terminus and one CTP amino acid peptide on the C-terminus for the treatment of hypovolemic shock, hemodialysis or cardiopulmonary bypass.

In another embodiment, the methods of the present invention provide Activase-altiplase/tPA having additionally at least one CTP amino acid peptide on the N-terminus and one CTP amino acid peptide on the C-terminus for the treatment of acute myocardial infarction, acute massive pulmonary embolism, or (change throughout) ischemic stroke.

In another embodiment, the methods of the present invention provide adenosine deaminase having additionally at least one CTP amino acid peptide on the N-terminus and one CTP amino acid peptide on the C-terminus for the treatment of severe combined immunodeficiency disease.

In another embodiment, the methods of the present invention provide immune globulin having additionally at least one CTP amino acid peptide on the N-terminus and one CTP amino acid peptide on the C-terminus for the treatment of transplant recipients.

In another embodiment, the methods of the present invention provide immune globulin is a CMV immune globulin. In another embodiment, the methods of the present invention provide glucocerebrosidase having additionally at least one CTP amino acid peptide on the N-terminus and one CTP amino acid peptide on the C-terminus for the treatment of Gaucher disease.

In another embodiment, the methods of the present invention provide Leukine-sargramostim/GM-CSF having additionally at least one CTP amino acid peptide on the N-terminus and one CTP amino acid peptide on the C-terminus for the Stimulation of hematopoietic progenitor cells.

In another embodiment, the methods of the present invention provide G-CSF having additionally at least one CTP amino acid peptide on the N-terminus and one CTP amino acid peptide on the C-terminus for the treatment of Neutropenia. In another embodiment, the methods of the present invention provide Venoglobulin-S/IgG having additionally at least one CTP amino acid peptide on the N-terminus and one CTP amino acid peptide on the C-terminus for the treatment of Immunodeficiency diseases.

In another embodiment, the methods of the present invention provide Proleukin-aldesleukin having additionally at least one CTP amino acid peptide on the N-terminus and one CTP amino acid peptide on the C-terminus for the treatment of renal carcinoma or metastatic melanoma.

In another embodiment, the methods of the present invention provide DNase having additionally at least one CTP amino acid peptide on the N-terminus and one CTP amino acid peptide on the C-terminus for the treatment of Cystic fibrosis.

In another embodiment, the methods of the present invention provide factor VIII having additionally at least one CTP amino acid peptide on the N-terminus and one CTP amino acid peptide on the C-terminus for the treatment of Hemophilia A.

In another embodiment, the methods of the present invention provide Helixate having additionally at least one CTP amino acid peptide on the N-terminus and one CTP amino acid peptide on the C-terminus for the treatment of Hemophilia A.

In another embodiment, the methods of the present invention provide L-asparaginase having additionally at least one CTP amino acid peptide on the N-terminus and one CTP amino acid peptide on the C-terminus for the treatment of acute lymphoblastic leukemia.

In another embodiment, the methods of the present invention provide WinRho SDF Rh IgG having additionally at least one CTP amino acid peptide on the N-terminus and one CTP amino acid peptide on the C-terminus for the treatment of Rh isoimmunization and immune thrombocytopenic purpura.

In another embodiment, the methods of the present invention provide Retavase retaplase/tPA having additionally at least one CTP amino acid peptide on the N-terminus and one CTP amino acid peptide on the C-terminus for the treatment of acute myocardial infarction.

In another embodiment, the methods of the present invention provide Factor IX having additionally at least one CTP amino acid peptide on the N-terminus and at least one CTP amino acid peptide on the C-terminus for the treatment of Hemophilia B.

In another embodiment, the methods of the present invention provide Factor IX having additionally at least one CTP amino acid peptide on the N-terminus and at least one CTP amino acid peptide on the C-terminus for the treatment of Hemophilia B.

In another embodiment, the methods of the present invention provide FSH having additionally at least one CTP amino acid peptide on the N-terminus and at least one CTP amino acid peptide on the C-terminus for stimulation of ovulation during assisted reproduction.

In another embodiment, the methods of the present invention provide globulin having additionally at least one CTP amino acid peptide on the N-terminus and at least one CTP amino acid peptide on the C-terminus for the prevention of respiratory syncytial virus disease.

In another embodiment, the methods of the present invention provide fibrin having additionally at least one CTP amino acid peptide on the N-terminus and at least one CTP amino acid peptide on the C-terminus for wound management and hemostasis. In another embodiment, the methods of the present invention provide interleukin-11 having additionally at least one CTP amino acid peptide on the N-terminus and at least one CTP amino acid peptide on the C-terminus for chemotherapy-induced thrombocytopenia.

In another embodiment, the methods of the present invention provide becaplermin/PDGF having additionally at least one CTP amino acid peptide on the N-terminus and at least one CTP amino acid peptide on the C-terminus for the treatment of diabetic foot ulcers.

In another embodiment, the methods of the present invention provide lepirudin/herudin having additionally at least one CTP amino acid peptide on the N-terminus and at least one CTP amino acid peptide on the C-terminus for anticoagulation in heparin-induced thrombocytopenia.

In another embodiment, the methods of the present invention provide soluble TNF having additionally at least one CTP amino acid peptide on the N-terminus and at least one CTP amino acid peptide on the C-terminus for the treatment of rheumatoid arthritis.

In another embodiment, the methods of the present invention provide Thymoglobulin having additionally at least one CTP amino acid peptide on the N-terminus and at least one CTP amino acid peptide on the C-terminus for the treatment of organ transplant rejection disease.

In another embodiment, the methods of the present invention provide factor VIIa having additionally at least one CTP amino acid peptide on the N-terminus and at least one CTP amino acid peptide on the C-terminus for the treatment of hemophilia.

In another embodiment, the methods of the present invention provide interferon alpha-2a having additionally at least one CTP amino acid peptide on the N-terminus and at least one CTP amino acid peptide on the C-terminus for the treatment of hairy cell leukemia and AIDS-related Kaposi's sarcoma.

In another embodiment, the methods of the present invention provide interferon alpha-2b having additionally at least one CTP amino acid peptide on the N-terminus and at least one CTP amino acid peptide on the C-terminus for the treatment of Hairy cell leukemia, genital warts, AIDS-related Kaposi's sarcoma, hepatitis C, hepatitis B, malignant melanoma, and follicular lymphoma.

In another embodiment, the methods of the present invention provide interferon alfa-N3 having additionally at least one CTP amino acid peptide on the N-terminus and at least one CTP amino acid peptide on the C-terminus for the treatment of genital warts.

In another embodiment, the methods of the present invention provide interferon gamma-1b having additionally at least one CTP amino acid peptide on the N-terminus and at least one CTP amino acid peptide on the C-terminus for the treatment of chronic granulomatous disease.

In another embodiment, the methods of the present invention provide interferon alfa n–1 having additionally at least one CTP amino acid peptide on the N-terminus and at least one CTP amino acid peptide on the C-terminus for the treatment of hepatitis C infection.

In another embodiment, the methods of the present invention provide Interleukin-2 having additionally at least one CTP amino acid peptide on the N-terminus and at least one CTP amino acid peptide on the C-terminus for the treatment of renal carcinoma and metastatic melanoma.

In another embodiment, the methods of the present invention provide interferon beta-1b having additionally at least one CTP amino acid peptide on the N-terminus and at least one CTP amino acid peptide on the C-terminus for the treatment of multiple sclerosis.

In another embodiment, the methods of the present invention provide hGH having additionally at least one CTP amino acid peptide on the N-terminus and at least one CTP amino acid peptide on the C-terminus for the treatment of wasting disease, AIDS, cachexia, or hGH deficiency.

In another embodiment, the methods of the present invention provide an OKT3 monoclonal antibody having additionally at least one CTP amino acid peptide on the N-terminus and at least one CTP amino acid peptide on the C-terminus for organ transplant.

In another embodiment, the methods of the present invention provide a Reo monoclonal antibody having additionally at least one CTP amino acid peptide on the N-terminus and at least one CTP amino acid peptide on the C-terminus for prevention of complications from coronary intervention and angioplasty.

In another embodiment, the methods of the present invention provide a monoclonal antibody having additionally at least one CTP amino acid peptide on the N-terminus and at least one CTP amino acid peptide on the C-terminus for treating colorectal cancer, Non-Hodgkin's lymphoma, kidney transplant rejection, metastatic breast cancer, or the prevention of respiratory syncytial virus disease.

In some embodiments, the CTP sequences modification is advantageous in permitting lower dosages to be used.

In some embodiments, "polypeptide" or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereivunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2—NH—). In some embodiments, the polypeptide bonds are substituted by hydroxyethylene bonds (—CH(OH)—CH2-). In some embodiments, the polypeptide bonds are substituted by thioamide bones (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the cytokines of the present invention are utilized in a linear form, although it will be appreciated by one skilled in the art that in cases where cyclicization does not severely interfere with cytokines characteristics, cyclic forms of the cytokines can also be utilized.

In some embodiments, the cytokines of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the cytokines are relatively short (about 5-15 kDa) and/or when it cannot be produced by recombinant techniques (i.e., not encoded by a nucleic acid sequence) and therefore involves different chemistry.

In some embodiments, solid phase cytokines synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the cytokines of the present invention. In some embodiments, recombinant protein techniques are used for generation of relatively long polypeptides (e.g., longer than 18-25 amino acid). In some embodiments, recombinant protein techniques are used for the generation of large amounts of the cytokines of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In another embodiment, cytokines of the present invention are synthesized using a polynucleotide encoding a polypeptide of the present invention. In some embodiments, the polynucleotide encoding cytokines of the present invention is ligated into an expression vector, comprising a transcriptional control of a cis-regulatory sequence (e.g., promoter sequence). In some embodiments, the cis-regulatory sequence is suitable for directing constitutive expression of the cytokines of the present invention. In some embodiments, the cis-regulatory sequence is suitable for directing tissue specific expression of the cytokines of the present invention. In some embodiments, the cis-regulatory sequence is suitable for directing inducible expression of the cytokines of the present invention.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the cytokines of the present invention. In some embodiments, signal sequences include, but are not limited to the endogenous signal sequence for EPO as set forth in SEQ ID NO: 19 or the endogenous signal sequence for IFN-□1 as set forth in SEQ ID NO: 64. In another embodiment, the signal sequence is N-terminal to the CTP sequence that is in turn N-terminal to the polypeptide sequence of interest; e.g. the sequence is (a) signal sequence—(b) CTP—(c) sequence-of-interest—(d) optionally 1 or more additional CTP sequences. In another embodiment, 1 or more CTP sequences is inserted between the signal sequence of a polypeptide sequence of interest and the polypeptide sequence of interest itself, thus interrupting the wild-type sequence of interest. Each possibility represents a separate embodiment of the present invention.

In one embodiment, following expression and secretion, the signal peptides are cleaved from the precursor proteins resulting in the mature proteins.

In some embodiments, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the cytokines of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the cytokines of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the cytokines of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the cytokines of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using a cytokine has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant cytokines of the present invention either remain within the recombinant cell, secreted into the fermentation medium, secreted into a space between two cellular membranes, such as the periplasmic space in E. coli; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, cytokines of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In one embodiment, production of CTP-cytokine polypeptides using recombinant DNA technology is illustrated in Example 1.

In some embodiments, the recombinant polypeptides are synthesized and purified; their therapeutic efficacy can be assayed either in vivo or in vitro. In one embodiment, the binding activities of the recombinant cytokines of the present invention can be ascertained using various assays as described in Examples 2-6 and 8-9.

In another embodiment, in vitro binding activity is ascertained by measuring the ability of the cytokine as described herein as well as pharmaceutical compositions comprising the same to treat diseases such as cancers such as hairy cell leukemia, malignant melanoma, Kaposi's sarcoma, bladder cancer, chronic myelocytic leukemia, kidney cancer, carcinoid tumors, non-Hodgkin's lymphoma, ovarian cancer, and skin cancers (for interferons). In one embodiment, in vivo activity is deduced by analyzing heamatocrit levels (FIGS. 3-5) and/or as a percentage of reticulocytes (for EPO). In another embodiment, in vivo activity is deduced by known measures of the disease that is being treated.

In some embodiment, the phrase "erythropoietin-associated conditions" refers to any condition associated with below normal, abnormal, or inappropriate modulation of erythropoietin. In some embodiment, levels of erythropoietin associated with such conditions are determined by any measure accepted and utilized by those of skill in the art. In some embodiment, erythropoietin-associated conditions typically include anemic conditions.

In some embodiment, "anemic conditions" refers to any condition, disease, or disorder associated with anemia. In some embodiment, anemic conditions include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplasic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

In one embodiment, the present invention comprises CTP-hGH-CTP-CTP polypeptides. In one embodiment, recombinant DNA technology methods are used for the production of CTP-hGH-CTP-CTP polypeptides as illustrated in Example 7. In one embodiment, the therapeutic efficacy of the CTP-hGH-CTP-CTP polypeptides of the present invention is assayed either in vivo. In one embodiment, the therapeutic efficacy of the CTP-hGH-CTP-CTP polypeptides of the present invention is assayed either in vitro. In one embodiment, the binding activities of the recombinant hGH polypeptides of the present invention are measured using Nb2 (a prolactin-dependent rat lymphoma cell line (ECACC Cell Bank)) or a FCD-P1 murine cell line, previously transfected with human growth hormone receptor. In one embodiment, binding of hGH to these receptors induces cell proliferation which in one embodiment is measured by the levels of MTT cellular stain as a function of hGH activity. In one embodiment, in vivo activity is deduced by measuring weight gain over time in treated growth hormone deficient animals.

In some embodiment, human growth hormone polypeptides of the present invention can be used to treat a subject, with conditions related to growth and weight, such as a growth deficiency disorder, AIDS wasting, aging, impaired immune function of HIV-infected subjects, a catabolic illness, surgical recovery, a congestive cardiomyopathy, liver transplantation, liver regeneration after hepatectomy, chronic renal failure, renal osteodystrophy, osteoporosis, achondroplasia/hypochondroplasia, skeletal dysplasia, a chronic inflammatory or nutritional disorder such as Crohn's disease, short bowel syndrome, juvenile chronic arthritis, cystic fibrosis, male infertility, X-linked hypophosphatemic rickets, Down's syndrome, Spina bifida, Noonan Syndrome, obesity, impaired muscle strength and fibromyalgia.

In some embodiments, interferon polypeptides of the present invention are used to treat a subject, with a variety of conditions such as hairy cell leukemia (HCL), Kaposi's sarcoma (KS), chronic myelogenous leukemia (CML), chronic hepatitis C (CHC), condylomata acuminata (CA), chronic hepatitis B, malignant melanoma, follicular non-Hodgkin's lymphoma, multiple sclerosis, chronic granulomatous disease, *Mycobacterium avium* complex (MAC), pulmonary fibrosis, osteoarthritis, and osteoporosis.

In another embodiment, polypeptides of the present invention comprising IFN α-2a as well as pharmaceutical compositions comprising the same are indicated for hairy cell leukemia (HCL), acquired immune deficiency syndrome (AIDS)-related Kaposi's sarcoma (KS), chronic-phase Philadelphia (Ph) chromosome-positive chronic myelogenous leukemia (CML) and chronic hepatitis C (CHC). IFN α-2a dosage varies depending on the indication. In another embodiment, the effectiveness of IFN α-2a as an antineoplastic, immunomodulator and antiviral agent has been established.

In another embodiment, polypeptides of the present invention comprising IFN α2b as well as pharmaceutical compositions comprising same are indicated for HCL, AIDS-related Kaposi's sarcoma and CHC. It is also indicated for condylomata acuminata (CA), chronic hepatitis B, malignant melanoma and follicular non-Hodgkin's lymphoma. IFN α-2b dosage varies depending on its indication of usage.

In another embodiment, cytokines of the present invention comprising a cytokine are administered in a dose of 1-90 micrograms in 0.1-5 ml solution. In another embodiment, polypeptides of the present invention comprising a cytokine are administered in a dose of 1-50 micrograms in 0.1-5 ml solution. In another embodiment, polypeptides of the present invention comprising a cytokine are administered in a dose of 1-25 micrograms in 0.1-5 ml solution. In another embodiment, polypeptides of the present invention comprising a cytokine are administered in a dose of 50-90 micrograms in 0.1-5 ml solution. In another embodiment, polypeptides of the present invention comprising a cytokine are administered in a dose of 10-50 micrograms in 0.1-5 ml solution.

In another embodiment, cytokines of the present invention comprising a cytokine are administered in a dose of 1-90 micrograms in 0.1-5 ml solution by intramuscular (IM) injection, subcutaneous (SC) injection, or intravenous (IV) injection once a week. In another embodiment, polypeptides of the present invention comprising a cytokine are administered in a dose of 1-90 micrograms in 0.1-5 ml solution by intramuscular (IM) injection, subcutaneous (SC) injection, or intravenous (IV) injection twice a week. In another embodiment, polypeptides of the present invention comprising a cytokine are administered in a dose of 1-90 micrograms in 0.1-5 ml solution by intramuscular (IM) injection, subcutaneous (SC) injection, or intravenous (IV) injection three times a week. In another embodiment, polypeptides of the present invention comprising a cytokine are administered in a dose of 1-90 micrograms in 0.1-5 ml solution by intramuscular (IM) injection, subcutaneous (SC) injection, or intravenous (IV) injection once every two weeks. In another embodiment, polypeptides of the present invention comprising a cytokine are administered in a dose of 1-90 micrograms in 0.1-5 ml solution by intramuscular (IM) injection, subcutaneous (SC) injection, or intravenous (IV) injection once every 17 days. In another embodiment, polypeptides of the present invention comprising a cytokine are administered in a dose of 1-90 micrograms in 0.1-5 ml solution by intramuscular (IM) injection, subcutaneous (SC) injection, or intravenous (IV) injection once every 19 days weeks.

In another embodiment, cytokines of the present invention comprise recombinant cytokines. In another embodiment, polypeptides of the present invention comprise a recombinant IFN-β. In another embodiment, polypeptides of the present invention comprise a recombinant IFN-α. In another embodiment, various recombinant IFN are known to one of skill in the art.

In another embodiment, protein drugs of molecular weight lower than 50,000 daltons, such as interferons, are in general short-lived species in vivo, having short circulatory half-lives of several hours. In another embodiment, the subcutaneous route of administration in general provides slower release into the circulation. In another embodiment, the CTP modified polypeptide of the invention prolongs the half-live of protein drugs of molecular weight lower than 50,000 daltons, such as interferons. In another embodiment, the CTP modified polypeptide of the invention enable interferons to exert their beneficial effects for a longer period of time.

In another embodiment, the immunogenicity of a CTP modified polypeptide comprising a cytokine is equal to an isolated cytokine. In another embodiment, the immunogenicity of a CTP modified polypeptide comprising a cytokine is comparable to an isolated cytokine. In another embodiment, modifying a cytokine as described herein with CTP peptides reduces the immunogenicity of the cytokine. In another embodiment, the CTP modified polypeptide comprising a cytokine is as active as an isolated cytokine protein. In another embodiment, the CTP modified polypeptide comprising a cytokine is more active than an isolated cytokine. In another embodiment, the CTP modified polypeptide comprising a cytokine maximizes the cytokine's protective ability against degradation while minimizing reductions in bioactivity.

In another embodiment, the cytokine of the present invention can be provided to the individual per se. In one embodiment, the cytokine of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, any of the compositions of this invention will comprise at least two CTP sequences bound to a cytokine of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In another embodiment, the preparation is administered in a local rather than systemic manner, for example, via injection of the preparation directly into a specific region of a patient's body.

Various embodiments of dosage ranges are contemplated by this invention. The dosage of the cytokine of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, a polypeptide comprising a cytokine and CTP units is formulated in an intranasal dosage form. In another embodiment, a polypeptide comprising a cytokine and CTP units is formulated in an injectable dosage form. In another embodiment, a polypeptide comprising a cytokine and CTP units is administered to a subject in a dose ranging from 0.0001 mg to 0.6 mg. In another embodiment, a polypeptide comprising a cytokine and CTP units is administered to a subject in a dose ranging from 0.001 mg to 0.005 mg. In another embodiment, a polypeptide comprising a cytokine and CTP units is administered to a subject in a dose ranging from 0.005 mg to 0.01 mg. In another embodiment, a polypeptide comprising a cytokine and CTP units is administered to a subject in a dose ranging from 0.01 mg to 0.3 mg. In another embodiment, a polypeptide comprising a cytokine and CTP units is administered to a subject in a dose in a dose ranging from 0.2 mg to 0.6 mg.

In another embodiment, a polypeptide comprising a cytokine and CTP units is administered to a subject in a dose ranging from 1-100 micrograms. In another embodiment, a polypeptide comprising a cytokine and CTP units is administered to a subject in a dose ranging from 10-80 micrograms. In another embodiment, a polypeptide comprising a cytokine and CTP units is administered to a subject in a dose ranging from 20-60 micrograms. In another embodiment, a polypeptide comprising a cytokine and CTP units is administered to a subject in a dose ranging from 10-50 micrograms. In another embodiment, a polypeptide comprising a cytokine and CTP units is administered to a subject in a dose ranging from 40-80 micrograms. In another embodiment, a polypeptide comprising a cytokine and CTP units is administered to a subject in a dose ranging from 10-30 micrograms. In another embodiment, a polypeptide comprising a cytokine and CTP units is administered to a subject in a dose ranging from 30-60 micrograms.

In another embodiment, a polypeptide comprising a cytokine and CTP units is administered to a subject in a dose ranging from 0.2 mg to 2 mg. In another embodiment, a polypeptide comprising a cytokine and CTP units is administered to a subject in a dose ranging from 2 mg to 6 mg. In another embodiment, a polypeptide comprising a cytokine and CTP units is administered to a subject in a dose ranging from 4 mg to 10 mg. In another embodiment, a polypeptide comprising a cytokine and CTP units is administered to a subject in a dose ranging from 5 mg and 15 mg.

In another embodiment, a polypeptide comprising a cytokine and CTP units is injected into the muscle (intramuscular injection). In another embodiment, a polypeptide comprising a cytokine and CTP units is injected below the skin (subcutaneous injection). In another embodiment, a polypeptide comprising an IFN protein and CTP units is injected into the muscle. In another embodiment, a polypeptide comprising an IFN protein and CTP units is injected below the skin.

In another embodiment, the methods of the invention include increasing the compliance in the use of cytokine therapy, comprising providing to a subject in need thereof, a polypeptide comprising a cytokine, one chorionic gonadotrophin carboxy terminal peptide (CTP) attached to an amino terminus of the cytokine, and two chorionic gonadotrophin carboxy terminal peptides attached to a carboxy terminus of the cytokine, thereby increasing compliance in the use of cytokine therapy.

In another embodiment, the methods of the invention include increasing the compliance of patients afflicted with chronic illnesses that are in need of a cytokine therapy. In another embodiment, the methods of the invention enable reduction in the dosing frequency of a cytokine by modifying the cytokine with CTPs as described hereinabove. In another embodiment, the term compliance comprises adherence. In another embodiment, the methods of the invention include increasing the compliance of patients in need of a cytokine therapy by reducing the frequency of administration of the cytokine. In another embodiment, reduction in the frequency of administration of the cytokine is achieved due to the CTP modifications which render the CTP-modified cytokine more stable. In another embodiment, reduction in the frequency of administration of the cytokine is achieved as a result of increasing T½ of the cytokine. In another embodiment, reduction in the frequency of administration of the cytokine is achieved as a result of increasing the clearance time of the cytokine. In another embodiment, reduction in the frequency of administration of the cytokine is achieved as a result of increasing the AUC measure of the cytokine.

In another embodiment, a polypeptide comprising a cytokine and CTP units is administered to a subject once a day. In another embodiment, a polypeptide comprising a cytokine and CTP units is administered to a subject once every two days. In another embodiment, a polypeptide comprising a cytokine and CTP units is administered to a subject once every three days. In another embodiment, a polypeptide comprising a cytokine and CTP units is administered to a subject once every four days. In another embodiment, a polypeptide comprising a cytokine and CTP units is administered to a subject once every five days. In another embodiment, a polypeptide comprising a cytokine and CTP units is administered to a subject once every six days. In another embodiment, a polypeptide comprising a cytokine and CTP units is administered to a subject once every week. In another embodiment, a polypeptide comprising a cytokine and CTP units is administered to a subject once every 7-14 days. In another embodiment, a polypeptide comprising a cytokine and CTP units is administered to a subject once every 10-20 days. In another embodiment, a polypeptide comprising a cytokine and CTP units is administered to a subject once every 5-15 days. In another embodiment, a polypeptide comprising a cytokine and CTP units is administered to a subject once every 15-30 days.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the cytokine dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired cytokine of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.001% to about 10.0% w/v of a subject compound, more preferably from about 00.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a cytokine as described herein is administered via systemic administration. In another embodiment, a cytokine as described herein is administered by intravenous, intramuscular or subcutaneous injection. In another embodiment, a cytokine as described herein is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized cytokine as described in sterile water for injection. In another embodiment, a pharmaceutical composition comprises a lyophilized cytokine as described in sterile PBS for injection. In another embodiment, a pharmaceutical composition comprises a lyophilized cytokine as described in sterile o.9% NaCl for injection.

In another embodiment, the pharmaceutical composition comprises a cytokine as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a cytokine as described herein and lactobionic acid and an acetate/glycine buffer. In another embodiment, the pharmaceutical composition comprises a cytokine as described herein and amino acids, such as arginine or glutamate that increase the solubility of interferon compositions in water. In another embodiment, the pharmaceutical composition comprises a lyophilized cytokine as described herein and glycine or human serum albumin (HSA), a buffer (e.g. acetate) and an isotonic agent (e.g NaCl). In another embodiment, the pharmaceutical composition comprises a lyophilized cytokine as described herein and phosphate buffer, glycine and HSA.

In another embodiment, the pharmaceutical composition comprising a cytokine as described herein is stabilized when placed in buffered solutions having a pH between about 4 and 7.2. In another embodiment, the pharmaceutical composition comprising a cytokine as described herein is stabilized with an amino acid as a stabilizing agent and in some cases a salt (if the amino acid does not contain a charged side chain).

In another embodiment, the pharmaceutical composition comprising a cytokine as described herein is a liquid composition comprising a stabilizing agent at between about 0.3% and 5% by weight which is an amino acid.

In another embodiment, the pharmaceutical composition comprising a cytokine as described herein provides dosing accuracy and product safety. In another embodiment, the pharmaceutical composition comprising a cytokine as described herein provides a biologically active, stable liquid formulation for use in injectable applications. In another embodiment, the pharmaceutical composition comprises a non-lyophilized cytokine as described herein.

In another embodiment, the pharmaceutical composition comprising a cytokine as described herein provides a liquid formulation permitting storage for a long period of time in a liquid state facilitating storage and shipping prior to administration.

In another embodiment, the pharmaceutical composition comprising a cytokine as described herein comprises solid lipids as matrix material. In another embodiment, the injectable pharmaceutical composition comprising a cytokine as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a cytokine as described herein is in the form of liposomes (J. E. Diederichs and al., Pharm./nd. 56 (1994) 267-275).

In another embodiment, the pharmaceutical composition comprising a cytokine as described herein comprises polymeric microparticles. In another embodiment, the injectable pharmaceutical composition comprising a cytokine as described herein comprises polymeric microparticles. In another embodiment, the pharmaceutical composition comprising a cytokine as described herein comprises nanoparticles. In another embodiment, the pharmaceutical composition comprising a cytokine as described herein comprises liposomes. In another embodiment, the pharmaceutical composition comprising a cytokine as described herein comprises lipid emulsion In another embodiment, the pharmaceutical composition comprising a cytokine as described herein comprises microspheres. In another embodiment, the pharmaceutical composition comprising a cytokine as described herein comprises lipid nanoparticles. In another embodiment, the pharmaceutical composition comprising a cytokine as described herein comprises lipid nanoparticles comprising amphiphilic lipids. In another embodiment, the pharmaceutical composition comprising a cytokine as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the cytokines of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074;

4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation of EPO Constructs

Materials and Methods:

Construction of Expression Vector pCI-dhfr:

pCI-neo mammalian expression vector was purchased from Promega (catalog no. E1841). The vector contains a CMV IE enhancer/promoter and neomycin phosphotransferase gene. The pSV2-dhfr clone was purchased from ATCC (Catalog No. 37146). The plasmid contains the murine dhfr gene. The construction of pCI-dhfr vector was performed as follows:

The pSV2-dhfr plasmid was digested with restriction enzyme BglII (3' end of the dhfr gene). DNA polymerase I, Large (Klenow) Fragment was used to fill-in the 5' overhangs to form blunt ends. The DNA was then digested with restriction enzyme AvrII (5' end of the dhfr gene). The dhfr gene (AvrII-blunt end) fragment was isolated.

The pCI-neo vector was digested with restriction enzyme BstXI (3' end of the neo gene). DNA polymerase I, Large (Klenow) Fragment was used to remove the 3' overhangs to form blunt ends. The DNA was then digested with restriction enzyme AvrII (5' end of the neo gene). The expression vector (AvrII-blunt end) was isolated.

The dhfr gene was ligated into pCI vector to form an expression vector containing the dhfr gene (pCI-dhfr).

Construction of hEPO-CTP Variants:

A cassette gene containing the C-Terminal peptide (CTP) of the beta subunit of hCG was fused to the coding sequence of human EPO (NP_000790.2) at different locations. Six EPO-CTP variants were constructed as illustrated in FIGS. 1A-1F. The proEPO signal peptide was used for the construction of the secreted EPO-CTP variants. XbaI-NotI fragments containing Epo sequences were ligated into the pCI-dhfr expression vector of the present invention.

Table 2 hereinbelow summarizes the primer sequences used for constructing the CTP—containing polypeptides of the present invention.

TABLE 2

| Primer number | SEQ ID NO | sequence | Restriction site (underlined in sequence) |
|---|---|---|---|
| 1 | 7 | 5' AA<u>TCTAGA</u>GGTCATCATGG GGGTGC 3' | XbaI |
| 2 | 8 | 5' ATT<u>GCGGCCGC</u>GGATCCAG AAGACCTTTATTG 3' | NotI |

TABLE 2 -continued

| Primer number | SEQ ID NO | sequence | Restriction site (underlined in sequence) |
|---|---|---|---|
| 17$^R$ | 9 | 5' TAA<u>ATATT</u>GGGGTGTCCGA GGGCCC 3' | SspI |
| 10 | 10 | 5' CC<u>AATATT</u>ACCACAAGCCC CACCACGCCTCAT 3' | SspI |
| 11$^R$ | 11 | 5' T<u>GCGGCCGC</u>GGATCCTTAT CTGTCCCCTGTCCTGC 3' | NotI |
| 15 | 12 | 5' GCCCTGCTGTCGGAAGC 3' | |
| 2$^R$ | 13 | 5' ATT<u>GCGGCCGC</u>GGATCCAG AAGACCTTTATTG | NotI |
| 23$^R$ | 14 | 5' CTTTGAGGAAGAGGAGCCC AGGACTGGGAGGC3' | |
| 24 | 15 | 5' CCTGGGCTCCTCTTCCTCA AAGGC 3' | |
| 38$^R$ | 16 | 5' GCTTCCGACAGCAGGGC 3' | |

EPO-1 701-1-p17-6 (Epo-1—SEQ ID NO: 1):

The XbaI-NotI 702 bp fragment was constructed by PCR using the above primers (SEQ ID NOs: 7-16). Then the XbaI-NotI PCR fragment containing Epo-ctp sequence was ligated into pCI-dhfr expression vector.

EPO-2 701-2-p24-2 (Epo-2—SEQ ID NO: 2):

The XbaI/ApaI fragment (hGH-ctp) of pCI-dhfr-401-2-p21-2 (hGH-ctpx2) was replaced by the XbaI/ApaI fragment (EPO-ctp) of 701-1-p17-6 to create an Epo-ctpx2.

EPO-4-701-4-p42-(Epo-4—SEQ ID NO: 4):

Firstly, a fragment from pCI-dhfr-EPO-ctp (701-1-p17-6) was constructed by PCR using primers 1 and 17 followed by XbaI/SspI digestion. This resulted in a fragment containing EPO and partial 5' CTP.

Secondly, a new fragment was constructed by overlapping PCR, on pGT123-hEpo as a template, using primer 10 and primer 11. SspI/NotI digestion resulted in fragment containing 3' partial CTP and Epo.

The two fragments were ligated into pCI-dhfr to construct the p701-4-p42-1 clone.

EPO-3-p56-6 (Epo-3 SEQ ID NO; 3):

Primers were purchased from Sigma-Genosys. PCR reaction was performed using primer 15 (SEQ ID NO: 12) and primer 2$^R$ (SEQ ID NO: 13) and plasmid DNA of pCI-dhfr-EPO-ctp x2 (701-2-p24-2) as a template. As a result of the PCR amplification, a 486 bp product was formed and ligated into TA cloning vector (Invitrogen, catalog K2000-01). Stu I-NotI fragment containing *Epo-ctp x2 sequence was isolated (209 bp).

Three sequential PCR reactions were performed. The first reaction was conducted with primer 1 (SEQ ID NO: 7) and primer 23$^R$ (SEQ ID NO: 14) and plasmid DNA of pGT123-epo-ctp as a template; as a result of the PCR amplification, an 80 bp product was formed (signal peptide).

The second reaction was conducted with primer 24 (SEQ ID NO: 15) and primer 11$^R$ (SEQ ID NO: 11) and plasmid DNA of 701-4-p42-1 as a template; as a result of the PCR amplification, a 610 bp product was formed.

The last reaction was conducted with primers 1 (SEQ ID NO: 7) and 11$^R$ (SEQ ID NO: 11) and a mixture of the products of the previous two reactions as a template; as a result of the PCR amplification, a 700 bp product was formed and the XbaI-StuI fragment was isolated.

The two fragments (XbaI-StuI and StuI-NotI) were inserted into the eukaryotic expression vector pCI-dhfr (triple ligation) to yield the 701-3-p56-6 clone.

EPO-5-p91-4 (Epo-5 SEQ ID NO; 5—(ctp-Epo):

Primers were ordered from Sigma-Genosys. A PCR reaction was performed using primer 1 (SEQ ID NO: 7) and primer 11$^R$ (SEQ ID NO: 11) and plasmid DNA of pCI-dhfr-ctp-EPO-ctp ×2 (701-3-p56-6) as a template; as a result of the PCR amplification, a 670 bp product was formed and ligated into TA cloning vector (Invitrogen, catalog K2000-01). XbaI-NotI fragment containing ctp-Epo sequence was ligated into our eukaryotic expression vector pCI-dhfr to yield the 701-5-p91-4 clone.

EPO-6-p90-1 (Epo-6 SEQ ID NO: 6—(ctp-Epo-ctp):

Three PCR reactions were performed. The first reaction was conducted with primer 1 (SEQ ID NO: 7) and primer 38$^R$ (SEQ ID NO: 16) and plasmid DNA of 701-3-p56-6 as a template; as a result of the PCR amplification, a 400 bp product was formed.

The second reaction was conducted with primer 15 (SEQ ID NO: 12) and primer 2$^R$ (SEQ ID NO: 13) and plasmid DNA of 701-1-p17-6 as a template; as a result of the PCR amplification, a 390 bp product was formed.

The last reaction was conducted with primers 1 (SEQ ID NO: 7) and 2$^R$ (SEQ ID NO: 13) and a mixture of the products of the previous two reactions as a template; as a result of the PCR amplification, a 787 bp product was formed and ligated into TA cloning vector (Invitrogen, catalog K2000-01). The XbaI-NotI fragment containing ctp-Epo-ctp sequence was ligated into the eukaryotic expression vector pCI-dhfr to yield the 701-6-p90-1 clone.

Example 2

Expression and Isolation of EPO-CTP Polypeptides

Materials and Methods

DNA Transfection and Clone Selection:

DG44 cells were transfected with pCI-DHFR expression vectors containing EPO-CTP variants using FuGENE6 Reagent (FuGENE Transfection Reagent—Roche Cat. 1 815 091 001). 48 hr following transfection, cells were diluted and seeded at 50-200 cells per well in a selective medium (CD DG44 Medium w/o HT (Gibco: Scotland part: #07990111A) Sku num.:ME060027 supplemented with 8 mM L-Glutamine Biological Industries: Cat: 03-020-1A) and 18 mL/L of 10% Pluronic F-68 solution (Gibco: Cat: 240040-032). Selected clones were screened for highest protein production using commercial ELISA. 3-5 producing clones per each variant were frozen for a backup cell bank. A selected clone for each variant was adapted to growth in larger scale cultures up to 1 L flasks on an orbital shaker platform. Supernatants were collected and analyzed by ELISA, SDS-PAGE and Western blot. Following the withdrawal of aliquots, the protein-containing supernatants were kept frozen until further use.

Cell Culture:

DG44 cells were maintained in DG44 medium with HT (cat#12610-010, Gibco) supplemented with 8 mM L-Glutamine (Biological Industries: Cat: 03-020-1A) and 18 mL/L of 10% Pluronic F-68 solution (Gibco: Cat: 240040-032), at 37° C. in humidified 8% CO$_2$ incubator. Transfected clones were maintained in DG44 basal medium without HT supplement, hypoxanthine and thymidine, with pluronic acid and L-glutamine.

Sample Preparation:

Supernatants were collected, filtrated and analyzed by ELISA to determine protein concentration. SDS-PAGE and Western blot were used to determine purity and identity. Following ELISA, sample concentrations were defined and the solution was dialyzed against PBS. Following the withdrawal of aliquots, the protein-contained supernatants were kept frozen at −20° C. until further use.

Western Blotting:

Samples were electrophoresed on nondenaturing 15% SDS-polyacrylamide gels. Gels were allowed to equilibrate for 10 min in 25 mM Tris and 192 mM glycine in 20% (vol/vol) methanol). Proteins were transferred to a 0.2 m pore size nitrocellulose membrane (Sigma, Saint Louis, Mo.) at 250 mA for 3 h, using a Mini Trans-Blot electrophoresis cell (Biorad Laboratories, Richmond, Calif.). The nitrocellulose membrane was incubated in 5% non-fat dry milk for 2 h at room temperature. The membrane was incubated with EPO anti-serum (1:1000 titer) overnight at 4° C. followed by three consecutive washes in PBS containing 0.1% Tween (10 min/wash). The membrane was incubated with secondary antibody conjugated to Horse Radish Peroxidase (HRP) (Zymed, San Francisco, Calif.) for 2 h at room temperature, followed by three washes. Finally, the nitrocellulose paper was reacted with enhanced chemiluminescent substrate (ECL) (Pierce, Rockford, Ill.) for 5 min, dried with a Whatman sheet, and exposed to X-ray film.

Results

Table 3 hereinbelow shows the concentrations of the various CTP-modified EPO forms obtained from 5 selected clones and their preparation for further testing.

TABLE 3

| #Version | # Clone | Stock Titer IU/ml[1] | Post dilution in Mock sup. according to Epo3 titer IU/ml[2] | Post ultrafiltration IU/ml[3] |
|---|---|---|---|---|
| Epo0 SEQ ID NO: 16 | 17 | 3093 | 102 | 335 |
| Epo1 SEQ ID NO: 1 | 47 | 1049 | 104 | 291 |
| Epo2 SEQ ID NO: 2 | 67 | 2160 | 110 | 303 |
| Epo3 SEQ ID NO: 3 | 85 | 105 | 119 | 392 |
| Epo4 SEQ ID NO: 4 | 112 | 6100 | ND | 342 |

[1]EPO variants stock concentration were determined by ELISA (Quantikine IVD Epo ELISA, DEP00, R&D Systems)
[2]Samples EPO-0, 1, 2 and 4 were diluted to 105 IU/ml in mock sup (Adjusted to Epo3 titer). Epo0 = wild type EPO expressed in the same system as the CTP modified EPOs
[3]All samples were concentrated and dialyzed by ultrafiltration against PBS to a final concentration of 180 IU/ml.

All proteins were detected by Western blot as illustrated in FIG. 2.

Example 3

Biological Activity of the EPO-CTP Polypeptides of the Present Invention

The TF-1 bioactivity test represents the ability of the EPO-CTP variants to bind its receptor and then stimulate activity which results in cell proliferation. Therefore, this test was used as a first step in evaluating the biological potency of the EPO-CTP polypeptides of the present invention.

Materials and Methods
Cell Proliferation Analysis:
Proliferation assay was performed with the cell line TF-1, measuring levels of MTT cellular stain as a function of EPO activity (Kitamura et al., Kitamura, T. et al. (1989) *Establishment and characterization of a unique human cell line that proliferates*; Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996). Exponentially growing TF-1 cells were washed twice, plated at about $10^4$ cells/well in microtiter plates, and incubated in basal medium with a titrated dilution series of EPO (Recormon®), EPO standard (NIBSC standard), rhEPO (MOD-7010), MOD-701 variants (EPO-1, EPO-2, EPO-3 and EPO-4) for 48 hours. 4 hours prior to assaying for cell proliferation, MTT reagent was added to the wells, and absorbance was measured by ELISA reader. A calculated protein concentration value for each variant protein was obtained from Eprex®'s (Epoetin (EPO)-man-made form of the human hormone) dose-response standard curve.

Results

The in vitro biological activity of EPO polypeptides was determined with an Epo-dependent cell line, human erythroleukemia TF-1 (DSMZ Cell Bank) [Dong et al., Biochemical and Biophysical Research Communications, Volume 339, Issue 1, 6 Jan. 2006, Pages 380-385]. The MTT assay was performed [Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996);], and the laboratory standard of EPO used to generate the standard curve was calibrated against the International Standard (Epo ampoule code 87/684 of NIBSC).

The results are summarized in Table 4 hereinbelow. The results indicate that the highest potency was achieved by using EPO 3 and EPO 0 in both 2 and 0.5 IU/ml concentrations.

TABLE 4

| TF-1 Bioactivity IU/ml | | | | | | | |
|---|---|---|---|---|---|---|---|
| Eprex ® STD IU/ml | EPO 0 SEQ ID NO: 16 | EPO 1 SEQ ID NO: 1 | EPO 2 SEQ ID NO: 2 | EPO 3 SEQ ID NO: 3 | EPO 4 SEQ ID NO: 4 | Recormon ® | EPO st |
| 2 | 4.93 | 2.32 | 2.13 | 6.91 | 3.55 | 3.44 | 7.40 |
| 0.5 | 1.60 | 0.76 | 0.53 | 1.34 | 0.84 | 0.87 | 1.53 |

Conclusion

As summarized in Table 4 hereinabove, different levels of potency were exerted by EPO-CTP polypeptides, indicating differences in receptor binding. EPO-CTP polypeptides differ by the number of CTP cassettes and the location to which they are fused. EPO-1 and EPO-2 contain 1 CTP sequence or 2 CTP sequences at the C-terminal of EPO, while EPO-3 contains 1 CTP at N-terminal and 2 CTP sequences at C-terminal. EPO-4 is a dimer of two EPO molecules linked by CTP sequence. EPO-3 demonstrated potency level quite similar to WT-EPO, while EPO-1 and EPO-4 were about 50% less potent than WT-EPO, and EPO-2 potency was even less than 50%.

Example 4

Evaluation of the EPO-CTP Polypeptides of the Present Invention in a Mouse Model The following experiment was performed in order to compare the bio-activity of the EPO-CTP polypeptides of the present invention and commercial EPO Materials and Methods
Animals:
Species/Strain: ICR or CD-1 Mice of either sex about 20-25 g
Group Size: n=7
No. Groups: 9
Total No. Animals: n=63
Experimental Design of the Study:
The experiment was set up as summarized in Table 5 hereinbelow.

TABLE 5

| | No. Mice per | TREATMENT | | |
|---|---|---|---|---|
| Group No. | Group | Compound | Dose Level | Dosing Regimen |
| 1 | n = 7 | Vehicle | 0 | 1x weekly |
| 2 | | MOCK | | |
| 3 | | MOD-7010 | 15 µg/kg | |
| 4 | | MOD-7011 | | |
| 5 | | MOD-7012 | | |
| 6 | | MOD-7013 | | |
| 7 | | MOD-7014 | | |
| 8 | | Commercial | 15 µg/kg | |
| 9 | | rhEPO | 5 µg/kg | 3 x weekly |

Animal Treatment:
All animals were administered with either control or the test EPO polypeptides of the present invention by bolus injection. The injection volume did not exceed 10 ml/kg. The length of the experiment was 22 days. A morbidity and mortality check was performed daily.

Reticulocyte Count and Hematocrit (hct) Examination:
Reticulocyte count was carried out in all test animals at day 2 and 14 hrs following the 1st respective vehicle or treatment injection. HCT was determined in all animals once prior to initial treatment ("0" Baseline control) and at 24 hrs after the 1st respective vehicle or treatment injection, and thereafter twice weekly until study termination (Day-22).

Results

Figure 4:
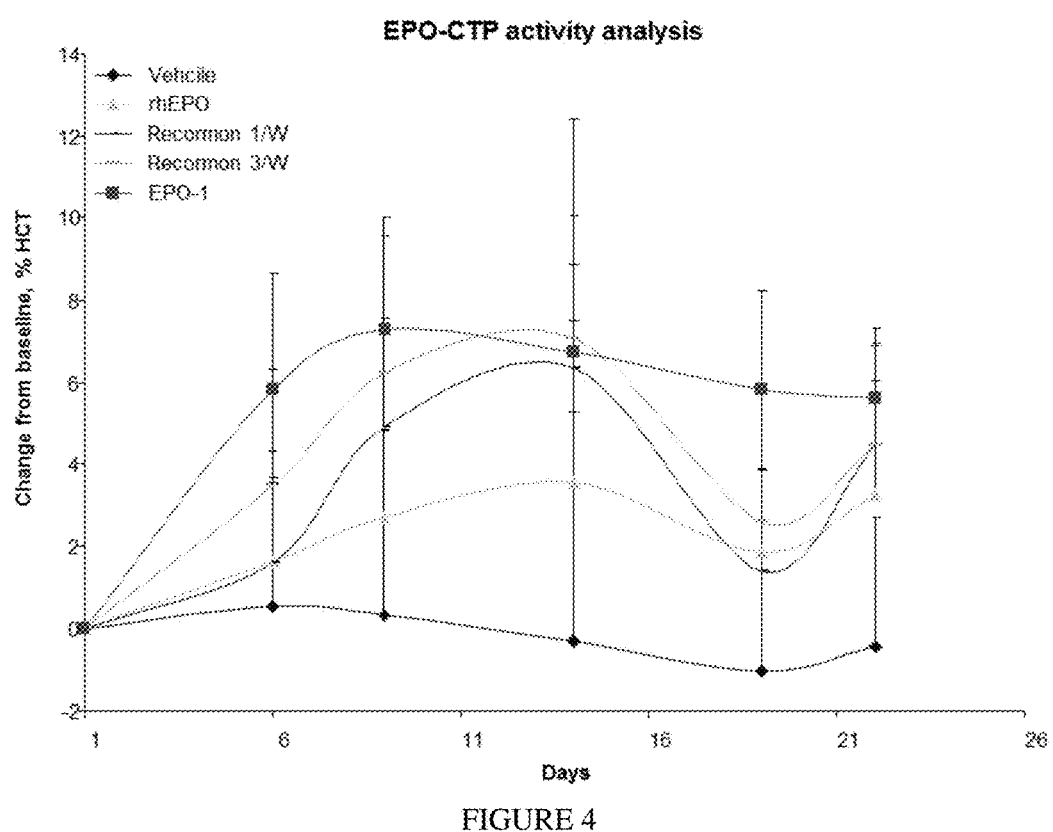
FIG. 4 is a graph illustrating the in vivo bioactivity of recombinant hEPO derivatives and EPO-1 (SEQ ID NO: 1). ICR mice (n=7/group) received a single IV injection/week (15 µg/kg) for three weeks of EPO-1, rhEPO-WT (SEQ ID NO: 16), Recormon® or Recormon® (5 µg/kg) 3 times a week. Control animals were injected IV with PBS. Blood samples were collected three times a week and haematocrit levels were detected. Each point represents the group average of haematocrit (%)±SE.
Figure 5:
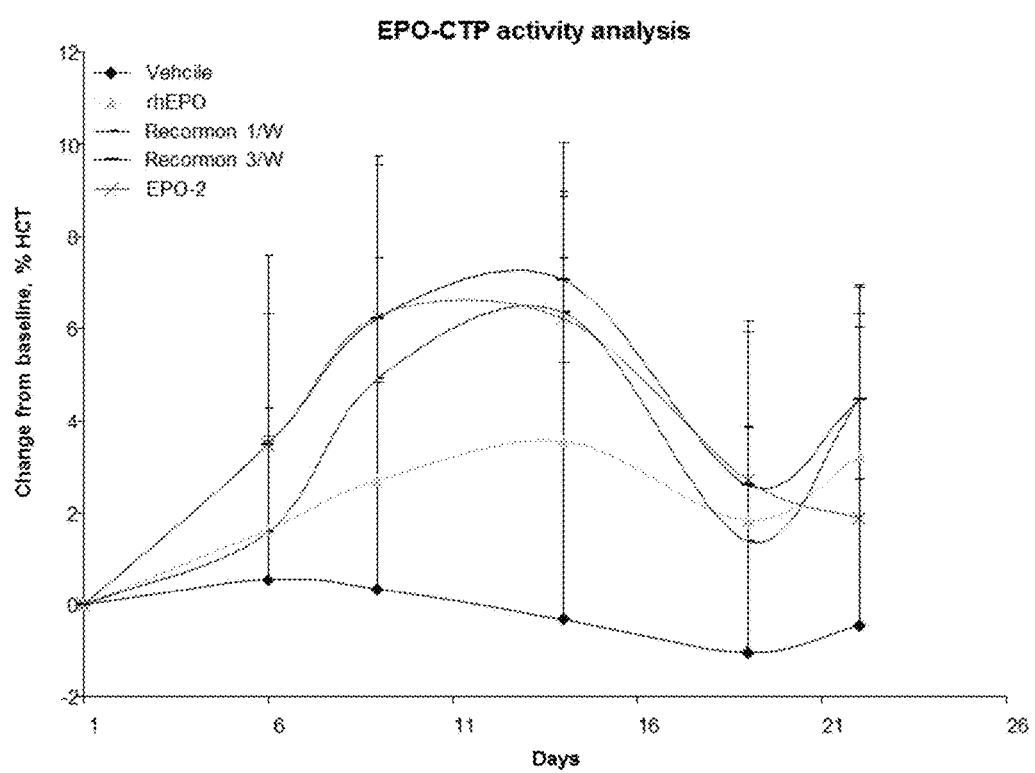
FIG. 5 is a graph illustrating the in vivo bioactivity of recombinant hEPO derivatives and EPO-2 (SEQ ID NO: 2). ICR mice (n=7/group) received a single IV injection/week (15 µg/kg) for three weeks of EPO-2 (SEQ ID NO: 2), rhEPO-WT (SEQ ID NO: 16), Recormon® or Recormon® (5 µg/kg) 3 times a week. Control animals were injected IV with PBS. Blood samples were collected three times a week and haematocrit levels were detected. Each point represents the group average of haematocrit (%)±SE.
Figure 6:
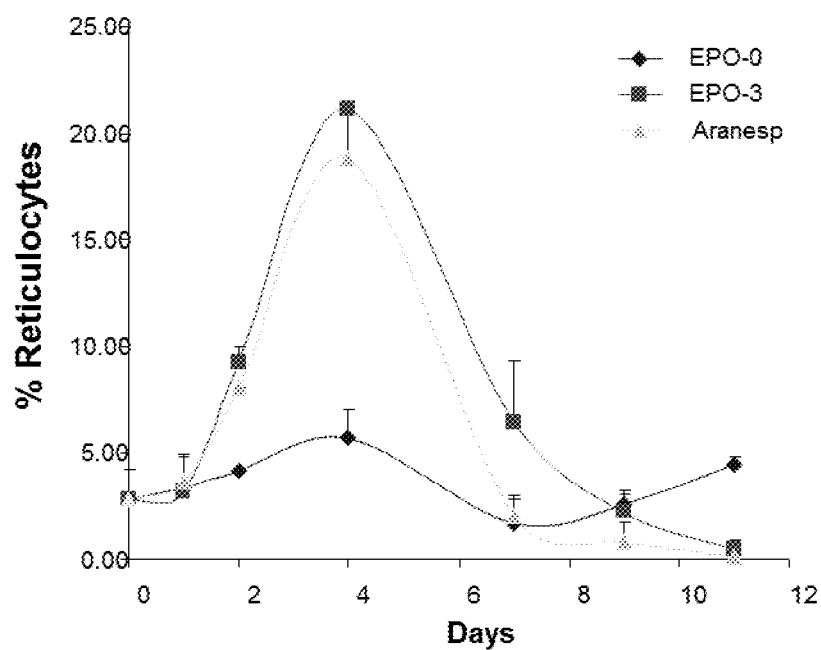
FIG. 6 is a time graph illustrating the change in reticulocyte level following a single bolus dose of EPO-0 (SEQ ID NO: 16), EPO-3 (SEQ ID NO: 3) and Aranesp®.
Figure 7:
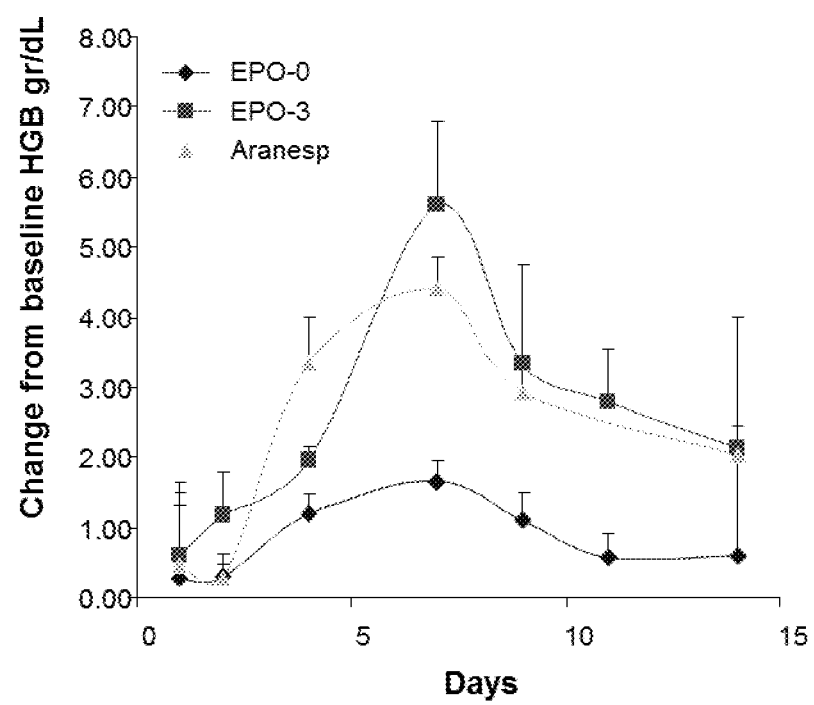
FIG. 7 is a time graph illustrating the change in hemoglobin level (presented as change from baseline) following a single bolus dose of EPO-0 (SEQ ID NO: 16), EPO-3 (SEQ ID NO: 3) and Aranesp®.
Figure 8:
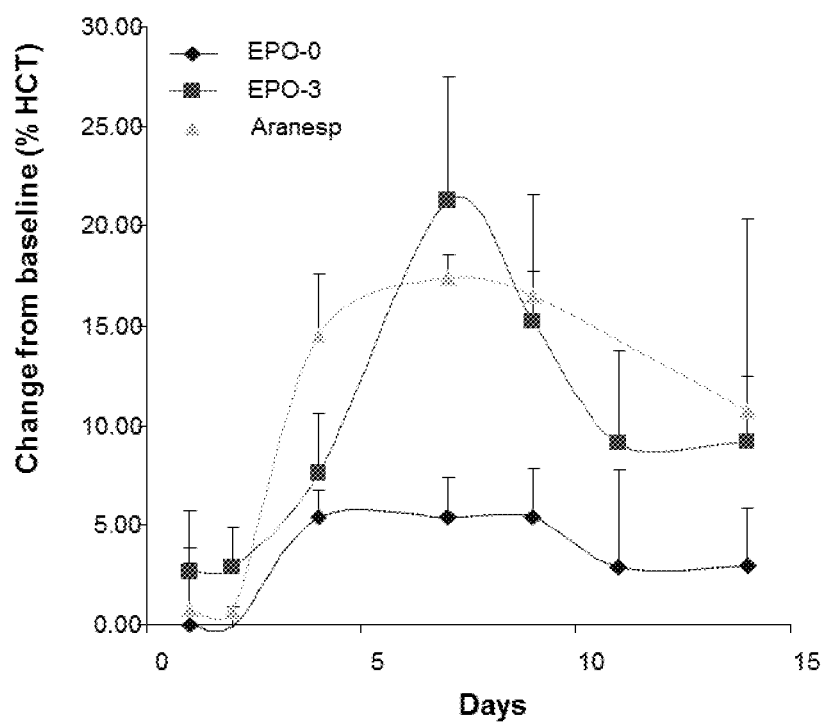
FIG. 8 is a time graph illustrating the change in hematocrit level following a single bolus dose of EPO-0 (SEQ ID NO: 16), EPO-3 (SEQ ID NO: 3) and Aranesp®.

The hematocrit results which are illustrated in FIGS. 3-5 show that EPO 3 has the highest hematocrit percentage change from baseline compared to EPO 1, EPO 2, Recormon® 1, Recormon® 3, rhEPO, and vehicle. The results demonstrating the percentage of reticulocytes in mice treated with the EPO-CTP polypeptides are summarized in Table 6 hereinbelow. These results show that EPO-3 is the most potent stimulator of erythropoiesis.

TABLE 6

| Days | % reticulocytes | |
|---|---|---|
| | 2 | 14 |
| Control | 3.72 | 3.46 |
| | 1.08 | 0.8 |
| Mock | 3.5 | 3.64 |
| | 0.6 | 1.13 |
| 7010 SEQ ID NO: 16 | 3.5 | 3.9 |
| | 0.6 | 1.54 |
| 7011 SEQ ID NO: 1 | 3.52 | 1.94 |
| | 1.38 | 1.08 |
| 7012 SEQ ID NO: 2 | 3.82 | 3.0 |
| | 1.02 | 0.88 |
| 7013 SEQ ID NO: 3 | 2.66 | 5.20 |
| | 0.97 | 2.96 |
| 7014 SEQ ID NO: 4 | 3.48 | 3.82 |
| | 0.71 | 0.90 |
| Recormon 1/W | 3.23 | 3.27 |
| | 0.73 | 0.59 |
| Recormon 3/w | 4.13 | 4.24 |
| | 1.21 | 1.14 |

Conclusion

The in vivo experiment was designed to measure two parameters; the first was to measure erythropoiesis parameters such as percentage of reticulocytes and increase of hemoglobin, RBC and hematocrit levels. The second was to measure the durability of the biological activity of each variant by injecting once weekly doses.

A superior performance of EPO-3 in its ability to stimulate erythropoiesis was observed in normal mice.

Example 5

Comparison of the EPO-CTP Polypeptides of the Present Invention to Aranesp®

The following experiment was performed in order to compare the biological activity of a single bolus dose of some EPO-CTP polypeptides of the present invention, commercial EPO and Aranesp®. Aranesp® is a commercial long-acting recombinant erythropoietin in which two site mutations were introduced, resulting in two additional N-glycosylation sites and an increase in the number of incorporated sialic acid residues.

Materials and Methods
Animals:
Species/Strain: Female CD-1 Mice of either sex about 20-25 g
Group Size: n=3
Experimental Design of the Study:
The experiment was set up as summarized in Table 7 hereinbelow.

TABLE 7

| Group # | Test Article | animals/ group/ time-point | Dose Solution Conc. (μg/mL) | Dose Volume (mL/kg) | Time-Points * (hours post-administration) |
|---|---|---|---|---|---|
| 1 | MOD-7010 SEQ ID NO: 11 | 3 | 1.5 | 10 | 0 (Pre-dose), 0.25, 0.5, 1, 2, 6, 24, 48, 96, 168, 216, 264 and 336 hr post-dose administration |
| 2 | MOD-7013 SEQ ID NO: 3 | 3 | 1.5 | 10 | 0.25, 0.5, 1, 2, 6, 24, 48, 96, 168, 216, 264 and 336 hr post-dose administration |

TABLE 7-continued

| Group # | Test Article | animals/ group/ time-point | Dose Solution Conc. (μg/mL) | Dose Volume (mL/kg) | Time-Points * (hours post-administration) |
|---|---|---|---|---|---|
| 3 | Aranesp ® | 3 | 1.5 | 10 | 0.25, 0.5, 1, 2, 6, 24, 48, 96, 168, 216, 264 and 336 hr post-dose administration |

Animal Treatment:
All animals were administered with either control or the test EPO polypeptides of the present invention by bolus injection. The injection volume did not exceed 10 ml/kg. The length of the experiment was 14 days. A morbidity and mortality check was performed daily.

Reticulocyte Count and Hematocrit (hct) Examination:
Reticulocyte count and hematocrit examination were performed as described above.

Results
The results are illustrated in FIGS. 6-9. Following a single I.V. injection of 15 μg/kg of EPO 3, all three blood parameters associated with erythropoietin i.e. number of reticulocytes, hemoglobin level and hematocrit, were improved relative to those obtained with similar injected dose of rhEPO or Aranesp®.

Example 6

Comparison of the Pharmacokinetics of EPO-CTP Polypeptides of the Present Invention to Aranesp®

The following experiment was performed in order to compare the pharmacokinetics of EPO-CTP polypeptide of the present invention, commercial EPO and Aranesp®.

Materials and Methods
Serum samples were analyzed in order to determine specific concentration levels for each sample. Concentration and time-point data were processed using WinNonLin non-compartmental analysis. Parameters determined included: AUC, CL, Ke, t½, Cmax, Tmax, and Vdz.

Serum concentrations were determined using two ELISA kits in parallel. EPO-3 serum concentration was measured using StemCell ELISA kit in comparison to EPO-0 and Aranesp® serum concentration which were determined using R&D system ELISA kit.

Results
The results of the pharmacokinetic analysis are summarized in Table 8, hereinbelow. These results show that EPO 3 exhibited favorable pharmacokinetic measures as indicated for example in AUC measures, t½, and Cmax. Tmax measures were equal to EPO-0, EPO-3, and Aranesp®.

TABLE 8

| Parameters | Units | EPO-0 | EPO-3 | Aranesp ® |
|---|---|---|---|---|
| AUClast | hr*mIU/mL | 31739 | 306072 | 178661 |
| CL^ | mL/hr/kg | 1.1152 | 0.2188 | 0.1207 |
| Ke | 1/hr | 0.157 | 0.0529 | 0.0639 |
| t½ | hr | 4.4139 | 13.1141 | 10.84 |
| Cmax | mIU/mL | 10766 | 16466 | 13266 |
| Tmax | Hr | 0.25 | 0.25 | 0.25 |
| Vdz | mL/kg | 7.1017 | 4.1394 | 1.8877 |

Figure 9:
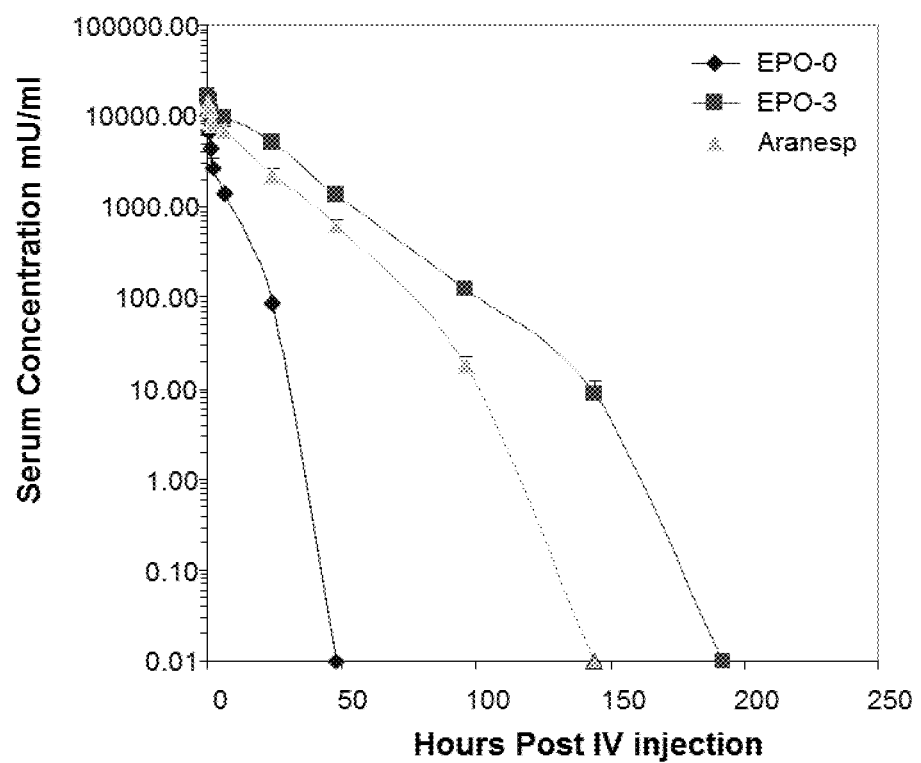
FIG. 9 is a graph illustrating the change in serum concentration of EPO-0 (SEQ ID NO: 16), EPO-3 (SEQ ID NO: 3) and Aranesp® post i.v. injection.

The results of the serum concentration analysis are illustrated in FIG. 9. These results show that EPO-3 was still detectable in the serum after about 190 hours. Both EPO-0 and Aranesp® were not detectable in the serum after about 140 hours and 50 hours, respectively.

Conclusion

Clearance of EPO-3 (MOD-7013) from the blood of CD-1 mice was significantly slower than that for rhEPO or Aranesp®. The corresponding calculated half life times were: rhEPO—4.41 h; Aranesp®—0.84 h; and MOD-7013-13.11 h.

Example 7

Generation of hGH Constructs

Materials and Methods

Four hGH clones (variants of 20 kD protein) were synthesized. Xba I-Not I fragments containing hGH sequences from the four variants were ligated into the eukaryotic expression vector pCI-dhfr previously digested with XbaI-NotI. DNA from the 4 clones (401-0, 1, 2, 3 and 4) was prepared. Another partial hGH clone (1-242 bp) from 22 kD protein was also synthesized (0606114). Primers were ordered from Sigma-Genosys. The primer sequences used to generate the hGH-CTP polypeptides of the present invention are summarized in Table 9, hereinbelow.

TABLE 9

| Primer number | SEQ ID NO | sequence | Restriction site (underlined in sequence) |
|---|---|---|---|
| 25 | 27 | 5' <u>CTCTAGA</u>GGACATGGCCAC 3' | XbaI |
| $32^R$ | 28 | 5' ACAGGGAGGTCTGGGGGTTCTG CA 3' | |
| 33 | 29 | 5' TGCAGAACCCCCAGACCTCCCT GTGC 3' | |
| $4^R$ | 30 | 5' CCAAACTCATCAATGTATCTT A 3' | |
| 25 | 31 | 5' <u>CTCTAGA</u>GGACATGGCCAC 3' | XbaI |
| $35^R$ | 32 | 5' CGAACTCCTGGTAGGTGTCAAA GGC 3' | |
| 34 | 33 | 5' GCCTTTGACACCTACCAGGAGT TCG 3' | |
| $37^R$ | 34 | 5' AC<u>GCGGCCGC</u>ATCCAGACCTTC ATCACTGAGGC 3' | NotI |
| $39^R$ | 35 | 5' <u>GCGGCCGC</u>GGACTCATCAGAAG CCGCAGCTGCCC 3' | |

Construction of 402-0-p69-1 (hGH) SEQ ID NO: 36:

MOD-4020 is the wild type recombinant human growth hormone (without CTP) which was prepared for use as control in the below described experiments.

Three PCR reactions were performed. The first reaction was conducted with primer 25 and primer $32^R$ and plasmid DNA of 0606114 (partial clone of hGH 1-242 bp) as a template; as a result of the PCR amplification, a 245 bp product was formed.

The second reaction was conducted with primer 33 and primer $4^R$ and plasmid DNA of 401-0-p57-2 as a template; as a result of the PCR amplification, a 542 bp product was formed.

The last reaction was conducted with primers 25 and $4^R$ and a mixture of the products of the previous two reactions as a template; as a result of the PCR amplification, a 705 bp product was formed and ligated into the TA cloning vector (Invitrogen, catalog K2000-01). The XbaI-NotI fragment containing hGH-0 sequence was ligated into the eukaryotic expression vector pCI-dhfr. The vector was transfected into DG-44 CHO cells. Cells were grown in protein-free medium.

Construction of 402-1-p83-5 (hGH-CTP)—SEQ ID NO: 37 and 402-2-p72-3(hGH-CTPx2)—SEQ ID NO: 38:

MOD-4021 is a recombinant human growth hormone which was fused to 1 copy of the C-terminal peptide of the beta chain of human Chorionic Gonadotropin (CTP). The CTP cassette of MOD-4021 was attached to the C-terminus (one cassette). MOD-4022 is a recombinant human growth hormone which was fused to 2 copies of the C-terminal peptide of the beta chain of human Chorionic Gonadotropin (CTP). The two CTP cassettes of MOD-4022 were attached to the C-terminus (two cassettes).

Construction of hGH-CTP and hGH-CTP-CTP was performed in the same way as the construction of hGH-0. pCI-dhfr-401-1-p20-1 (hGH*-ctp) and pCI-dhfr-401-2-p21-2 (hGH*-ctp x2) were used as templates in the second PCR reaction.

Figure 10:
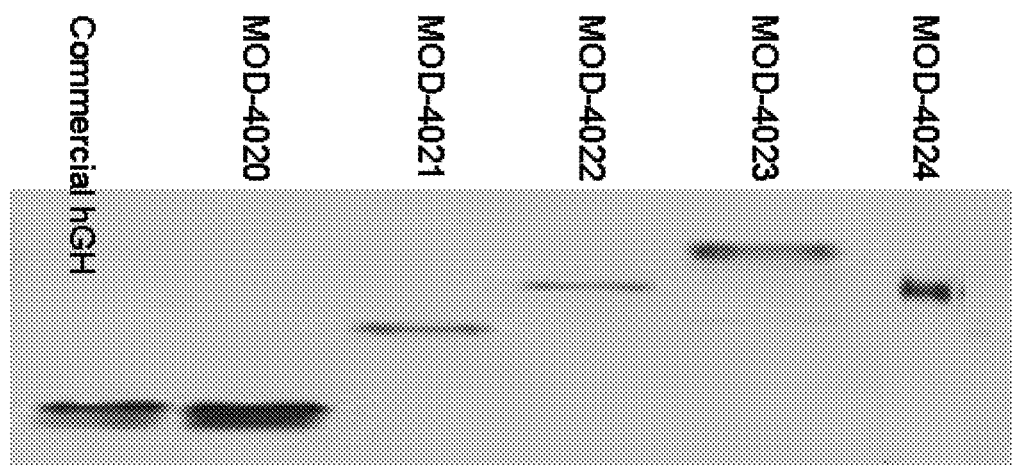
FIG. 10 is a Western blot illustrating the molecular weight & identity of MOD-4020 (SEQ ID NO: 36), MOD-4021 (SEQ ID NO: 37), MOD-4022 (SEQ ID NO: 38), MOD-4023 (SEQ ID NO: 39) and MOD-4024 (SEQ ID NO: 40). PAGE SDS gel was blotted and stained using monoclonal anti-hGH antibodies. The photograph indicates that like commercial and wild type hGH, MOD-7020-4 variants are recognized by anti-hGH antibodies.

MOD-4021 and MOD-4022 were expressed in DG-44 CHO cells. Cells were grown in protein-free medium. The molecular weight of MOD-4021 is ~30.5 Kd since hGH has a MW of 22 Kd while each "CTP cassette" contributes 8.5 Kd to the overall molecular weight (see FIG. 10). The molecular weight of MOD-4022 is ~39 Kd (see FIG. 10).

Construction of 402-3-p81-4 (CTP-hGH-CTP-CTP)—SEQ ID NO: 39 and 402-4-p82-9(CTP*hGH-CTP-CTP)—SEQ ID NO: 40:

MOD-4023 is a recombinant human growth hormone which was fused to 3 copies of the C-terminal peptide of the beta chain of human Chorionic Gonadotropin (CTP). The three CTP cassettes of MOD-4023 were attached to both N-terminus (one cassette) and the C-terminus (two cassettes). MOD-4024 is a recombinant human growth hormone which is fused to 1 truncated and 2 complete copies of the C-terminal peptide of the beta chain of human Chorionic Gonadotropin (CTP). The truncated CTP cassette of MOD-4024 was attached to the N-terminus and two CTP cassettes were attached to the C-terminus (two cassettes).

Three PCR reactions were performed. The first reaction was conducted with primer 25 and primer $35^R$ and plasmid DNA of p401-3-p12-5 or 401-4-p22-1 as a template; as a result of the PCR amplification, a 265 or 220 bp product was formed. The second reaction was conducted with primer 34 and primer $37^R$ and plasmid DNA of TA-hGH-2-q65-1 as a template; as a result of the PCR amplification, a 695 bp product was formed. The last reaction was conducted with primers 25 and $37^R$ and a mixture of the products of the previous two reactions as a template; as a result of the PCR amplification, a 938 or 891 bp product was formed and ligated into TA cloning vector (Invitrogen, catalog K2000-01). Xba I-Not I fragment containing hGH sequence was ligated into our eukaryotic expression vector pCI-dhfr.

MOD-4023 and MOD-4024 were expressed in DG-44 CHO cells. Cells were grown in protein-free medium. The molecular weight of MOD-4023 is ~47.5 Kd (see FIG. 10) and the molecular weight of MOD-4024 is ~43.25 Kd (see FIG. 10).

Construction of 402-6-p95a-8 (CTP-hGH-CTP)—SEQ ID NO: 41: Construction of hGH-6 was performed in the same way as the construction of hGH-3. pCI-dhfr-402-1-p83-5 (hGH-ctp) was used as a template in the second PCR reaction.

Construction of 402-5-p96-4 (CTP-hGH)—SEQ ID NO: 42:

PCR reaction was performed using primer 25 and primer 39$^R$ and plasmid DNA of pCI-dhfr-ctp-EPO-ctp (402-6-p95a-8) as a template; as a result of the PCR amplification, a 763 bp product was formed and ligated into TA cloning vector (Invitrogen, catalog K2000-01). Xba I-Not I fragment containing ctp-hGH sequence was ligated into our eukaryotic expression vector pCI-dhfr to yield 402-5-p96-4 clone.

Example 8

In Vivo Bioactivity Tests of hGH-CTP Polypeptides of the Present Invention

The following experiment was performed in order to test the potential long acting biological activity of hGH-CTP polypeptides in comparison with commercial recombinant human GH and MOD-4020.

Materials and Methods

Female hypophysectomized rats (60-100 g) received a weekly S.C. injection of 21.7 μg hGH-CTP polypeptides or a once daily 5 μg S.C. injection of control commercial rhGH.

Weight was measured in all animals before treatment, 24 hours following first injection and then every other day until the end of the study on day 21. Each point represents the group's average weight gain percentage ((Weight day 0−weight last day)/Weight day 0). Average weight gain was normalized against once-daily injection of commercial hGH. The treatment schedule is summarized in Table 10.

TABLE 10

| No. | Drug | N | Route | Treatment Schedule | Equi-molar Dose (μg/rat) | Accumu-late Dosage (μg/rat) | Dose Vol. (ml) |
|---|---|---|---|---|---|---|---|
| 1 | Vehicle | 7 | s.c. | days 1, 7 and 13; 1/W | NA | NA | 0.25 |
| 2 | Mock | 7 | s.c. | days 1, 7 and 13; 1/W | NA | NA | 0.25 |
| 3 | MOD-4020 SEQ ID NO: 36 | 7 | s.c. | days 1, 7 and 13; 1/W | 21.7 | 65 | 0.25 |
| 4 | MOD-4021 SEQ ID NO: 37 | 7 | s.c. | days 1, 7 and 13; 1/W | 21.7 | 65 | 0.25 |
| 5 | MOD-4022 SEQ ID NO: 38 | 7 | s.c. | days 1, 7 and 13; 1/W | 21.7 | 65 | 0.25 |
| 6 | MOD-4023 SEQ ID NO: 39 | 7 | s.c. | days 1, 7 and 13; 1/W | 21.7 | 65 | 0.25 |
| 7 | MOD-4024 SEQ ID NO: 40 | 7 | s.c. | days 1, 7 and 13; 1/W | 21.7 | 65 | 0.25 |
| 8 | Commercial hGH v.1 | 7 | s.c. | days 1, 7 and 13; 1/W | 21.7 | 65 | 0.25 |
| 9 | Commercial hGH v.1 | 7 | s.c. | days 1-13; d/W | 5 | 65 | 0.25 |

Results

Results are summarized in FIG. 11. These results show that MOD-4023 (SEQ ID NO: 39) and MOD-4024 (SEQ ID NO: 40) induced over 120% weight gain compared to commercial rhGH which induced 100% weight gain.

Conclusion 3 weekly doses (Days of injections; 1, 7, and 13) of 21.7 μg of MOD-4023 (SEQ ID NO: 39) and MOD-4024 (SEQ ID NO: 40) induced a 30% greater weight increase in hypophysectomised rats compared to commercial rhGH injected at the same accumulated dose which was administered once per day at a dose of 5 μg for 13 days.

Example 9

The Superiority hGH-CTP Polypeptides of the Present Invention

Pharmacokinetic Studies

Single-dose pharmacokinetic studies were conducted in Sprague-Dawley rats. All animal experimentation was conducted in accordance with the Animal Welfare Act, the Guide for the Care and Use of Laboratory Animals, and under the supervision and approval of the Institutional Animal Care and Use Committees of Modigene, Biotechnology General Ltd. Rats were housed either individually or two per cage in rooms with a 12-h light/dark cycle. Access to water (municipal supply) and noncertified rodent chow was provided ad libitum.

To compare the pharmacokinetics of MOD-4023 and GH in rats, four groups of Sprague-Dawley rats (270-290 g), three to six male rats per group. The rats were randomly assigned to four treatment groups (see Table 11). Rats were administered a single s.c. or i.v. injection of GH (50 μg/kg i.v. or s.c.) or MOD-4023 (108 μg/kg i.v. or s.c.). With the exception of the predose sample, which was collected under isoflurane anesthesia, blood collection was performed in unanesthetized animals. Blood samples (approximately 0.25 ml) were collected in EDTA-coated microtainers for ELISA analyses of MOD-4023 plasma concentration at the times outlined in Table 11. After each sampling, the blood volume was replaced with an equal volume of sterile 0.9% saline. Samples were stored on wet ice for up to 1 h prior to centrifugation and plasma harvest. Plasma samples were stored at approximately −20° C. prior to analysis.

TABLE 11

Experimental design of rat pharmacokinetic study

| Trt. Grp. | Test Article | No. of animals/ group/ timepoint | Dose Route | Gender | Dose Level (μg/kg) | Injected Vol. (μl) | Concentration (μg/ml)/Total vol. (ml) | Time-Points * (hours post-dose) |
|---|---|---|---|---|---|---|---|---|
| 1 | Biotropin ® | 6# | SC | Male | 50 | 500 | 20/5 | 0 (Pre-dose) 0.5, 2, 4, 8, 24, 48 |
| 2 | MOD-4023 | 6# | SC | Male | 108 | 500 | 43.2/5 | 0.5, 2, 4, 8, 24, 48, 72, 96 |
| 3 | Biotropin ® | 6# | IV | Male | 50 | 300 | 20/3 | 0, 0.12, 2, 4, 8, 24 |

TABLE 11-continued

Experimental design of rat pharmacokinetic study

| Trt. Grp. | Test Article | No. of animals/ group/ timepoint | Dose Route | Gender | Dose Level (µg/kg) | Injected Vol. (µl) | Concentration (µg/ml)/Total vol. (ml) | Time-Points * (hours post-dose) |
|---|---|---|---|---|---|---|---|---|
| 4 | MOD-4023 | 6# | IV | Male | 108 | 300 | 43.2/3 | 0.12, 2, 4, 8, 24, 48, 72 Terminal blood samples |

Volume of blood sample/time point - 500 µl

3 rats per time point.

A commercial sandwich ELISA kit specific for detection of human growth hormone (Roche Diagnostics) was used for evaluation of the rat plasma samples. This kit detects human growth hormone in plasma by means of an antibody sandwich ELISA format. This kit was initially used to measure the concentration of MOD-4023 in rat plasma. For these plasma samples, an MOD-4023 standard curve (1.2-100 ng/ml) was used and the concentrations of MOD-4023 in rat plasma were interpolated from this curve.

Standard pharmacokinetic parameters, including clearance (CL or CL/F), volume of distribution (Vd or Vd/F), half-life ($t_{1/2}$), area under the plasma concentration versus time curve (AUC), maximal observed plasma concentration ($C_{max}$) and time to maximal observed plasma concentration ($T_{max}$), were obtained from plasma albutropin or GH concentration/time curves by noncompartmental analysis using the modeling program WinNonlin (Pharsight, version 3.1). Plasma MOD-4023 or GH concentration data were uniformly weighted for this analysis. The AUC was calculated using the log-linear trapezoidal analysis for the i.v. data and the linear-up/log-down trapezoidal method for the s.c. data. Plasma concentration profiles for each rat (with the exception of the s.c. albutropin data) or monkey were analyzed individually, and mean±standard error of the mean (S.E.M.) values for the pharmacokinetic parameters are reported in Table 13, and FIG. 17.

Single Dose/Repeated Dose Weight Gain Assay (WGA)

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized were 70-90, at the time of the experiment. This is the standard USP and EP bioassay for hGH. Hypophysectomized rats (rats from which the pituitary gland was removed) lose their ability to gain weight. Injections of hGH (and of MOD-4023) to these rats result in weight gain. Based on the measured weight gain along a defined period of time and the amount of hGH injected, the specific activity of hGH (and MOD-4023) is determined. Rats were administered either a single s.c. doses of 0.4, 0.8 and 4 mg/Kg or repeated s.c. doses of 0.6 and 1.8 mg/Kg 4 days apart for 3 weeks. Individual body weights of all animals are determined at randomization, prior to the first dosing, thereafter every two days or in case of decedents at the time of death, and prior to sacrifice.

Pharmacodynamics/Pharmacokinetics Studies

Hypophysectomized (interaural method) male rats, 3-4 weeks of age, were obtained from CRL Laboratories. During a post-surgical acclimation period of 3 weeks, rats were examined and weighed twice weekly to eliminate animals deemed to have incomplete hypophysectomy evidenced by weight gain similar to that of sham-operated rats. Those rats with incomplete hypophysectomized were eliminated from the study. The average body weights of the hypophysectomized and sham rats were 70 and 150 g, respectively, at the time of the experiment.

Rats were administered a single s.c. with MOD-4023, vehicle, human growth hormone MOD-4023 or human growth hormone (20 µg/rat) was administered s.c. in an injection volume of 0.2 ml/rat. The dose of GH was 0.35 and 1.05 µg/Kg, a dose of growth hormone that was equimolar with the amount of GH in a corresponding 0.6 and 1.8 µg/Kg dose of MOD-4023. The treatment groups are summarized in Table 12. Following injection, plasma samples for IGF-1 analyses were obtained at the times described in Table 12. Samples were analyzed for IGF-1 concentration using a commercial ELISA (R&D systems).

TABLE 12

Treatment schedule for hypophysectomized rat study

| Trt. Grp. | Test Article | No. of animals/ group/ timepoint | Dose Route | Eq. Dose (mg/rat) | Eq. Dose Dosage (mg/Kg) | MOD-4023 Conc. mg/ml | Dose Vol. (ml) | Time-Points * (hours post-dose) |
|---|---|---|---|---|---|---|---|---|
| M7 | Biotropin ® | 9 | SC | 0.032 | 0.35 | 0.16 | 0.2 | 0 (Pre-dose) 0.5, 2, 4, 8, 24, 48, 72, 96 |
| M8 | Biotropin ® | 9 | SC | 0.095 | 1.05 | 0.475 | 0.2 | 0 (Pre-dose) 0.5, 2, 4, 8, 24, 48, 72, 96 |
| M9 | EN648-01-08-005 | 12 | SC | 0.032 (0.055) | 0.35 (0.6) | 0.275 | 0.2 | 1, 2, 4, 8, 24, 48, 72, 96 |
| M10 | EN648-01-08-005 | 12 | SC | 0.095 (0.165) | 1.05 (1.8) | 0.825 | 0.2 | 1, 2, 4, 8, 24, 48, 72, 96 |

Volume of blood sample/time point - 500 µl     Terminal blood samples

Carbohydrate Content and Sialic Acid Content

Analysis of O-glycans is based on a Prozyme kit. O-glycans are chemically and enzymatically cleaved from the protein and separated from peptides using paper chromatography. Sequencing of the O-glycan pool is performed by sequential enzymatic digestions (exo-glycosidases) followed by HPLC analysis compared to standards.

Glycoprofiling with Sequence Analysis

Glycoprofiling was performed by Ludger Ltd. Two samples (EN648 and RS0708) were taken through triplicate releases and each release was also analyzed by HPLC in triplicate. Triplicate 300 µg samples of EN648 and RS0708 and a single 100 µl sample of citrate/sodium chloride buffer, plus a positive control fetuin (250 µg) and a 100 µl water negative control, were ultra-filtratered by centrifugation using a molecular weight cut off membrane of 10,000 Da to replace the buffer with water, then taken through hydrazinolysis under O-mode conditions (6 h at 60° C.). Released glycans were re-N-acetylated and cleaned up by LudgerClean CEX cartridges. An aliquot of the released glycans was then labeled with 2-aminobenzamide (2AB), cleaned up with Ludger Clean S cartridges and analyzed by LudgerSep-N2 HILIC-HPLC.

Monosaccharide Content

Analysis of neutral monosaccharides requires hydrolysis of glycans to their constituent monosaccharide components. The hydrolysis was performed by Ludger Ltd, on intact glycoprotein samples. Specifically, 50 µg of intact glycoprotein was acid hydrolyzed, 2-AB (2-aminobenzamide) labeled and run on a reverse phase HPLC column. This method hydrolyzes all glycans present on the glycoprotein inclusive of N and O linked types.

Sialic Acid Profiling

Two samples (EN648 and RS0708) and a buffer control were analyzed. Sialic acid analysis requires mild acid release of the monosaccharides followed by DMB fluorophore labeling and HPLC analysis on a LudgerSep-R1 column. 50 µg of intact glycoprotein was acid hydrolyzed for each analysis.

Results and Conclusions

MOD-4023 (CTP-hGH-CTP-CTP) is a single chain protein of 275 amino acids and up to twelve O-linked carbohydrates. The structure consists of modified human Growth Hormone (Somatropin) attached to three copies of the C-terminal peptide (CTP) of the beta chain of human Chorionic Gonadotropin (hCG); one copy at the N-terminus and two copies (in tandem) at the C terminus. Human Growth Hormone is comprised of 191 amino acids. CTP is comprised of 28 amino acids and four O-linked sugar chains.

Pharmacokinetics of MOD-4023 in SD Rats

The pharmacokinetics of MOD-4023 was evaluated and compared to that of commercial hGH (Biotropin®).

TABLE 13

Mean pharmacokinetic parameters following single-dose i.v. and s.c. administration of MOD-4023 and GH (Biotropin ®) in Sprague-Dawley rats
PK Statistics

| Parameters | Units | SC | | IV | |
| --- | --- | --- | --- | --- | --- |
| | | Biotropin ® | MOD-4023 | Biotropin ® | MOD-4023 |
| Dose | mg/Kg | 50 | 50 | 50 | 50 |
| AUClast | hr*ng/mL | 41 | 680 | 162.7 | 1568.3 |

TABLE 13-continued

Mean pharmacokinetic parameters following single-dose i.v. and s.c. administration of MOD-4023 and GH (Biotropin ®) in Sprague-Dawley rats
PK Statistics

| Parameters | Units | SC | | IV | |
| --- | --- | --- | --- | --- | --- |
| | | Biotropin ® | MOD-4023 | Biotropin ® | MOD-4023 |
| Cmax | ng/ml | 13 | 36.8 | 275.8 | 926 |
| Tmax | hr | 0.5 | 8 | 0 | 0 |
| MRT | hr | 2.5 | 12.9 | 0.5 | 9.9 |
| T½ alpha | hr | | 1.58 | | 0.74 |
| T½ beta | hr | 1.73 | 9 | 0.5 | 6.9 |

Data Statistical Analysis

Analysis of serum samples was performed in order to determine specific concentration levels for each sample. Concentration and time-point data were processed using WinNonLin noncompartmental analysis.

Figure 17:
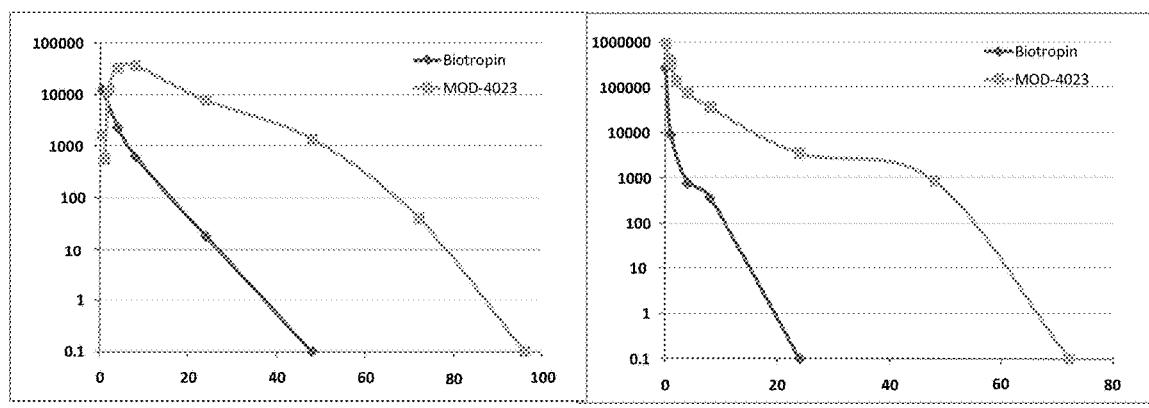
FIG. 17 are graphs showing the mean plasma MOD-4023 or GH concentrations (pg/ml) following a single i.v. or s.c. dose of MOD-4023 or GH in rats (n=3-6 per dose/route).

Parameters that were determined included: AUC, MRT, t½, Cmax, and Tmax. FIG. 17 demonstrates the superior pharmacokinetic profile of MOD-4023 plasma concentration compared to GH concentrations (pg/ml) following a single i.v. or s.c. dose of MOD-4023 or GH in rats (n=3-6 per dose/route).

Following a single S.C. injection of 50 µg/kg, clearance of MOD-4023 from SD rat's blood was significantly slower than that of MOD-4026 and of Biotropin®. The corresponding calculated half-life times and AUCs were:

| Biotropin ® | T½ 1.7 h, AUC 41 hr*ng/mL |
| MOD-4026 | T½ 8.5 h, AUC 424 hr*ng/mL |
| MOD-4023 | T½ 9.0 h, AUC 680 hr*ng/mL |

Conclusion:

MOD-4023 was chosen as the final candidate out of 6 other variants. MOD-4023 demonstrated superior performance in terms of biological activity and pharmacokinetics.

Single Dose and Repeated Dose Weight Gain Assay

Figure 18:
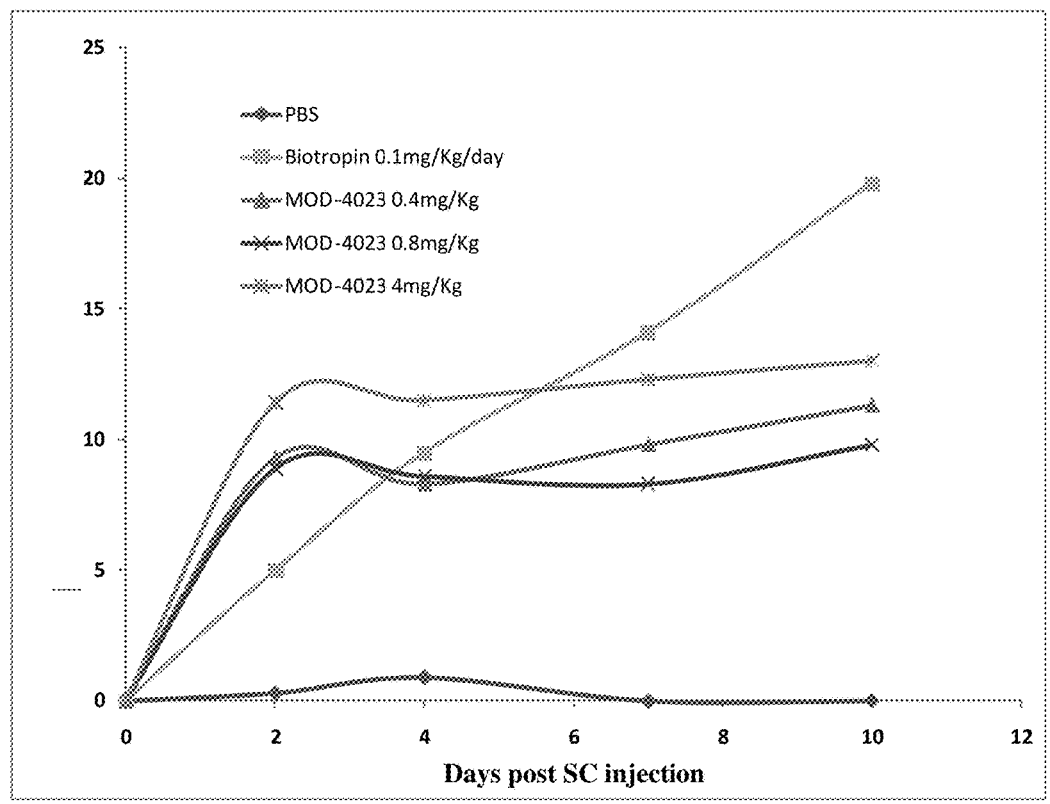
FIG. 18 are graphs showing the mean incremental weight gain following a single s.c. doses of MOD-4023 (0.4, 0.8 and 4 mg/Kg) in hypophysectomized rats in comparison to daily GH injections (0.1 mg/Kg/Day) (n=10 per dose).

The results comparing whole body growth response following different dosing patterns of MOD-4023 in hypophysectomized rats are demonstrated in FIG. 18. The results demonstrate that a single injection of 0.4 & 0.8 mg/Kg/day doses of hGH-CTP were equivalent to 4 daily injections of 0.1 mg/Kg/day of Biotropin®. The peak of the hGH-CTP effect was after 2 days.

Figure 19:
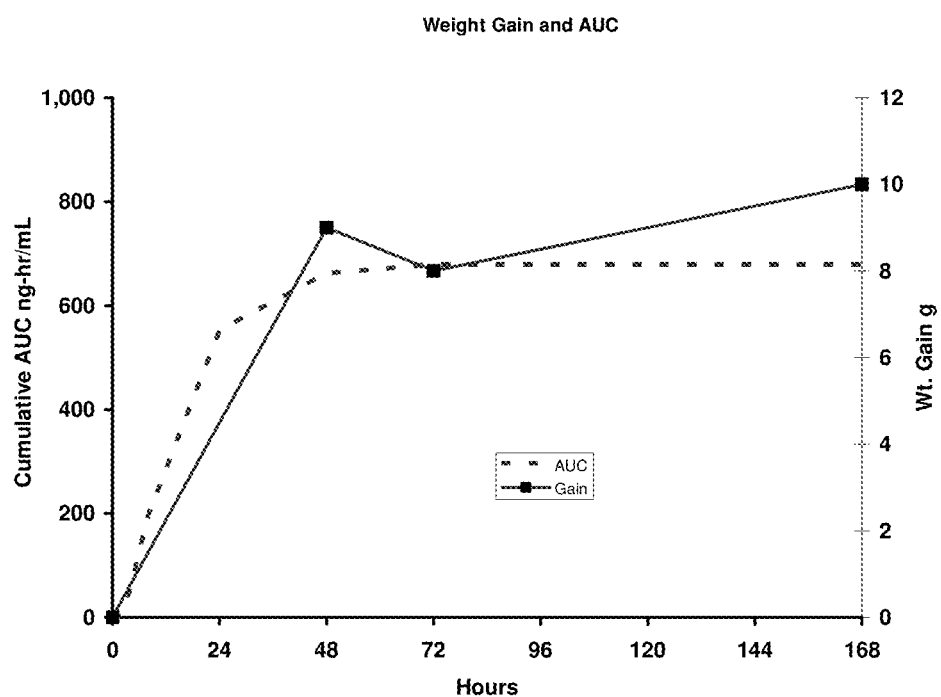
FIG. 19 is a graph showing the area Under the Curve following single injection of MOD-4023 correlates with Body Weight gain in Rats.
Figure 20:
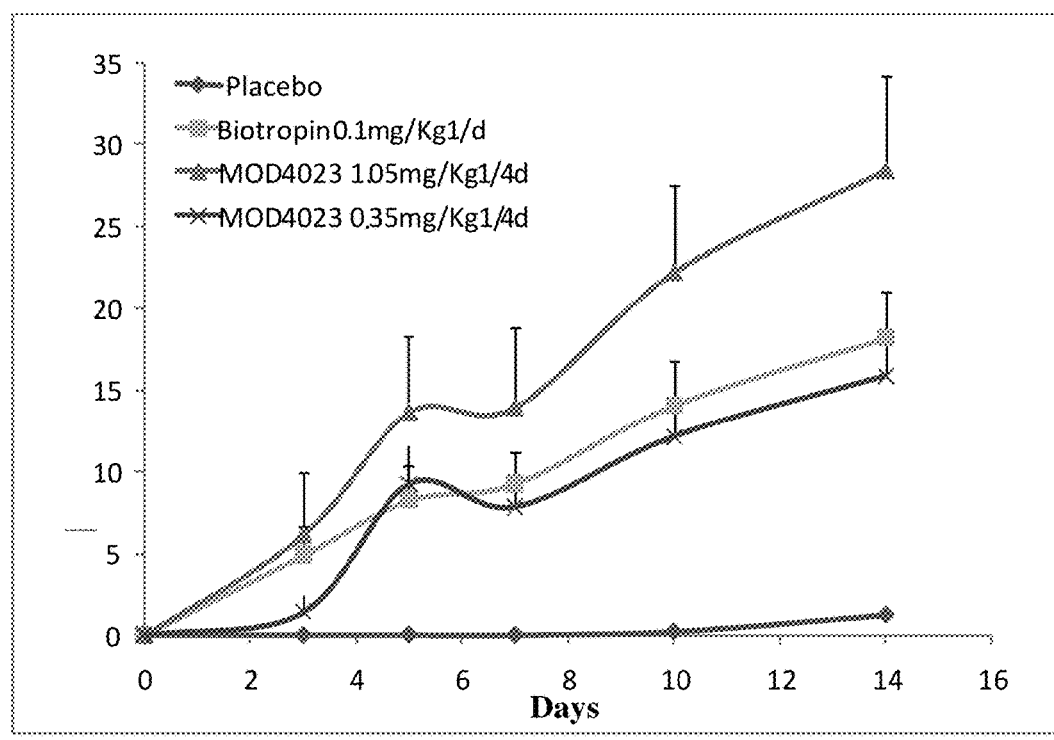
FIG. 20 is a graph showing the incremental weight gain following a s.c. doses of MOD-4023 (0.4, 0.8 and 4 mg/Kg) 4 days apart in hypophysectomized rats in comparison to daily GH injections (0.1 mg/Kg/Day) (n=10 per dose).

FIG. 19 further demonstrates that the area under the curve following single injection of MOD-4023 correlates with Body Weight gain in Rats. Thus, the collective data demonstrates that body weight gain is closely correlated with cumulative AUC.

hGH-CTP construct administered 4 days apart promotes the same weight gain as daily injections of Biotropin® as demonstrated in FIG. 20. Half-life of hGH in humans is expected to be 5× better than in rats—indicating potential peak effect in humans after 10 days for one single injection. These results support administration of hGH-CTP construct, MOD-4023, once weekly or bi-weekly in humans.

Glyco Analysis of MOD-4023

FIG. 23 shows glycan analysis, wherein structural assignments and percentage areas of peaks are based upon HPLC and enzyme array digests.

The monosaccharide profiles indicate that the MOD-4023 glycoprotein samples contain predominantly O-link type glycans. The major O-glycan peak is sialylated core 1 (Neu5Acα2-3Galβ1-3GalNAc). The major sialic acid is Neu5Ac and there are some minor peaks suggesting the presence of 3-4% of di-acetylated sialic acid N-acetyl-9-O-acetylneuraminic acid (NeuS, 9Ac2) and less than 1% N-glycolylneuraminic acid. There are also small amounts of Neu5Acα2-6(Galβ1-3)GalNAc.

Pharmacokinetics and Pharmacodynamics of MOD-4023 in Hypophysectomized Rats

Non-compartmental pharmacokinetic analysis was performed on the mean serum concentration versus time curves for each group. MOD-4023 Cmax was significantly higher than Biotroin Cmax. The terminal half-live of MOD-4023 was 6 times higher than Biotropin®.

TABLE 14

Pharmacokinetic Parameter Estimates of MOD-4023 and Biotropin ® Following a Single Subcutaneous Injection in hypophysectomized Rats

| Group | Dose mg/kg | Gender | Cmax ng/mL | Tmax hr | $AUC_{0-\infty}$ ng-hr/mL | $AUC_{0-t}$ ng-hr/mL | CL/F mL/hr/kg | $T_{1/2}$ hr |
|---|---|---|---|---|---|---|---|---|
| MOD-4023 | 1.8 | M | 2,150 | 8 | 37,713 | 37,695 | 0.928 | 6.86 |
|  | 0.6 | M | 681 | 8 | 11,505 | 11,489 | 3.042 | 6.8 |
| hGH | 1.05 | M | 1,078 | 0.5 | 3,541 | 3,540 | 9.884 | 1 |
|  | 0.35 | M | 439 | 0.5 | 1,279 | 1,279 | 27.36 | 1 |

Figure 21:
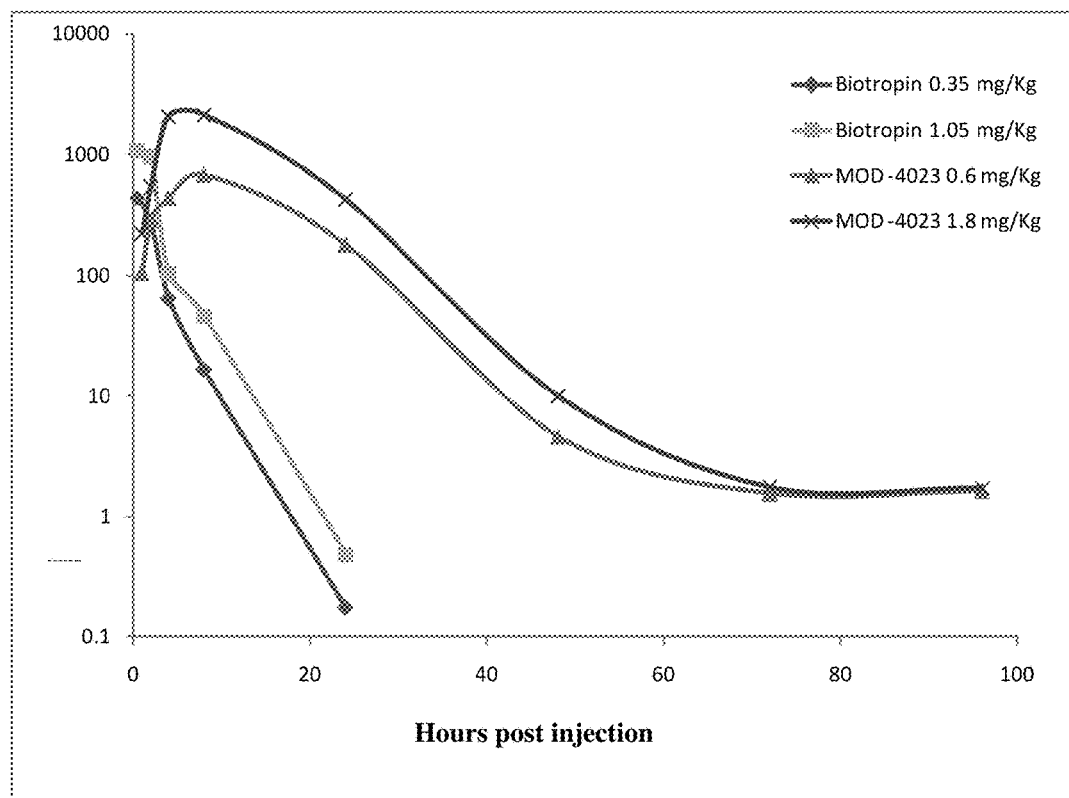
FIG. 21 is a graph showing hGH serum concentration in hypophysectomized rat following SC injection of MOD-4023 and commercial hGH. Single dose of MOD-4023 0.6 or 1.8 mg/Kg and Biotropin® 0.35 or 1.05 mg/Kg were injected subcutaneously to hypophysectomised rats for determination of PK/PD profile. Serum hGH post injection was measured using specific ELISA kits.

The $AUC_{0-t}$ and the $AUC_{0-\infty}$ were very similar suggesting the duration of sampling was adequate to characterize the pharmacokinetic profiles. AUC of MOD-4023 was 10 times higher than of Biotropin®. Moreover, Cmax was generally proportional to dose and for MOD-4023 and it was twice as high as Cmax of Biotropin®. However, as shown in FIG. 21, Tmax of MOD-4023 was 8 hr as compare to 0.5 hr of Biotropin® and the terminal half-lives did not appear to vary with dose level. T½ of MOD-4023 was 6.8 times longer than of Biotropin®.

Figure 22:
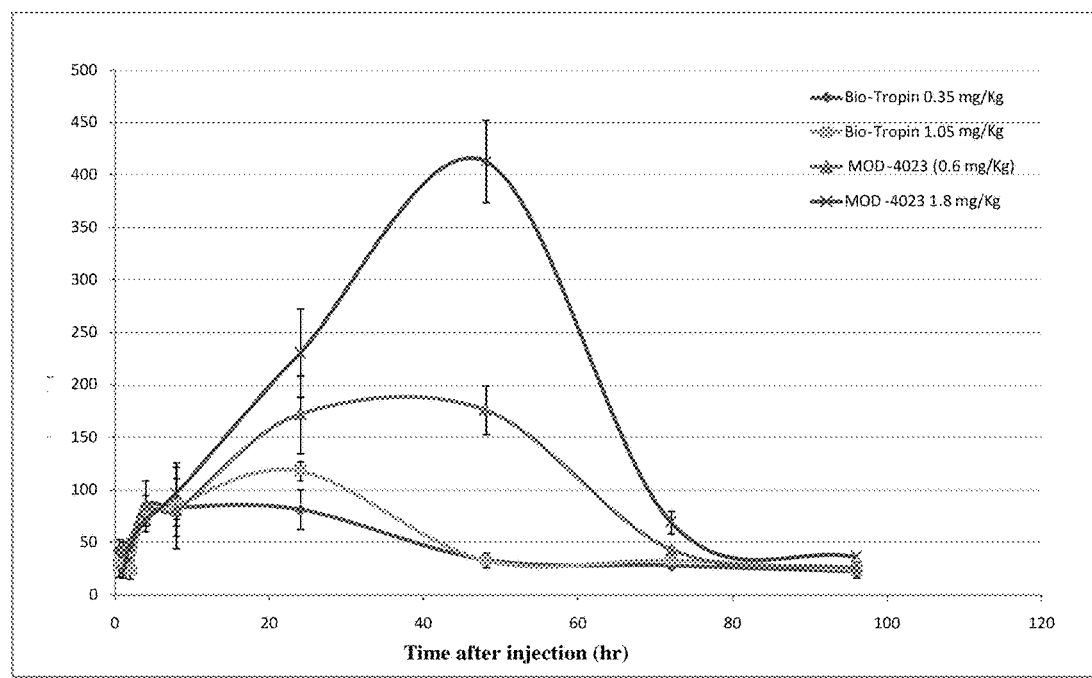
FIG. 22 is a graph showing IGF-1 serum levels in Hypophysectimized Rats Following SC injection of MOD-4023 and commercial hGH. Single dose of MOD-4023 0.6 or 1.8 mg/Kg and Biotropin® 0.35 or 1.05 mg/Kg were injected subcutaneously to hypophysectomised rats for determination of PK/PD profile. Serum IGF-I post injection was measured using specific ELISA kits (Roche Diagnostics).

Indirect effects of GH are mediated primarily by a insulin-like growth factor-I (IGF-I), a hormone that is secreted from the liver and other tissues in response to growth hormone. A majority of the growth promoting effects of growth hormone is actually due to IGF-I acting on its target cells. Accordingly, the effect of the CTP-hGH construct, MOD-4023, on IGF-1 serum levels in hypophysectimized rats was measured. FIG. 22 presents results of IGF-1 serum levels in hypophysectimized rats following SC injection of MOD-4023 and commercial hGH.

A single dose of MOD-4023 0.6 or 1.8 mg/Kg and Biotropin® 0.35 or 1.05 mg/Kg was injected subcutaneously to hypophysectomised rats for determination of PK/PD profile. Serum IGF-I post injection was measured using specific ELISA kits (Roche Diagnostics).

The cumulative serum levels of IGF-I following injection of MOD-4023 was significantly higher than following injection of Biotropin®. Cmax was generally proportional to dose and for MOD-4023 it was 3-4 times higher than Cmax of Biotropin®. Tmax of MOD-4023 was 36-48 hr as compare to 20-24 hr of Biotropin®. In conclusion, higher hGH levels and longer presence in serum result in significant increase in IGF-1 levels.

Pharmacokinetic/Toxicokinetic Analysis in Rhesus Monkeys

Serum concentrations versus time curves were generated for each animal. Non-compartmental analysis was performed with WinNonlin professional version 5.2.1 (Pharsight Corporation, Mt View Calif.). The estimated pharmacokinetic parameters are shown in the table 15 below:

TABLE 15

Estimates of MOD-4023 Pharmacokinetic Parameters (Mean ± SD) from Non-compartmental Analysis Following A Single Subcutaneous Injection in Rhesus Monkeys

| Parameter | 1.8 mg/kg | 90 mg/kg |
|---|---|---|
| Cmax (µg/mL) | 2.073 ± 0.417 | 108.7 ± 46.0 |
| Tmax (hr) | 4 ± 0 | 11 ± 7 |
| $AUC_{0-t}$ (µg-hr/mL) | 38.7 ± 7.4 | 2,444 ± 394 |
| $AUC_{0-\infty}$ (µg-hr/mL) | 39.0 ± 7.3 | 2,472 ± 388 |
| CL/F (mL/hr/kg) | 47.5 ± 9.0 | 37.04 ± 4.78 |

TABLE 15-continued

Estimates of MOD-4023 Pharmacokinetic Parameters (Mean ± SD) from Non-compartmental Analysis Following A Single Subcutaneous Injection in Rhesus Monkeys

| Parameter | 1.8 mg/kg | 90 mg/kg |
|---|---|---|
| $T_{1/2}$ (hr) | 10.00 ± 1.47 | 9.85 ± 1.07 |
| Vz/F (mL/kg) | 701 ± 236 | 529 ± 104 |

The $AUC_{0-t}$ and the $AUC_{0-\infty}$ were very similar suggesting the duration of sampling was adequate to characterize the pharmacokinetic profiles. Cmax was proportional to dose. Tmax was later at the higher dose. Tmax was at 4 hours for all animals in the low dose group and was at 8 or 24 hours in the high dose group. Terminal half-lives are similar for the two dose groups.

AUC was approximately proportional to dose with a slightly larger than proportional AUC at the higher dose producing a slightly lower estimate for CL/F and Vz/F compared to the lower dose. It is not possible to say if CL and Vz are lower at the higher dose or if F is lower at the lower dose. There was overlap between the groups so it is questionable that this represents a meaningful difference in CL/F and Vz/F.

Pharmacokinetic parameters estimated by the model were very similar to those from non-compartment analysis. Absorption and elimination half-lives are shown in table 16 below:

TABLE 16

Estimates of MOD-4023 Absorption and Elimination Half-lives (Mean ± SD) Following Subcutaneous Injection Derived From Pharmacokinetic Modeling in Rhesus Monkeys

| Dose | $T_{1/2\ abs}$ (hr) | $T_{1/2\ el}$ (hr) |
|---|---|---|
| 1.8 mg/kg | 1.17 ± 0.40 | 10.41 ± 2.36 |
| 90 mg/kg | 6.49 ± 1.87 | 7.26 ± 1.85 |

The data indicate that the elimination rates are fairly similar between the groups with a slightly longer T½ el in the lower dose group. The absorption, however, is more than 5-fold slower following subcutaneous administration of 90 mg/kg compared to that following 1.8 mg/kg. As in the case of the non-compartmental analysis, modeling indicated a later Tmax at the high dose.

Although GH supplementation is effective in the treatment of GH deficiency in children and adults, the disadvantages of daily injections over extended periods of time limit its use by physicians in certain patient populations as well as increase the risk of dosing error, the number of care givers, the cost of treatment and/noncompliance. Especially important in certain populations, such as children of short stature who may not understand the implications of not following the prescribed GH dosing regimen, is the necessity of compliance to achieve the optimal benefit from GH therapy. The issue of finding a more suitable alternative to daily GH injections and subsequent compliance gains further importance as GH-deficient children transition into adults with a continuing need for GH treatment. The requirement of daily therapy is largely due to recombinant GH's short plasma half-life and has led to the development of a sustained release form of G H (Reiter E O. Attire K M., Mashing T J. Silverman B L. Kemp S F. Neolith R B. Ford K M. and Sanger P. A multimember study of the efficacy and safety of sustained release GH in the treatment of naive pediatric patients with GH deficiency. J. Clin. Endocrinol. Metab. 86 (2001), pp. 4700-4706.).

MOD-4023, a recombinant human growth hormone-CTP fusion protein, as described herein, has a pharmacokinetic profile in the rat that is longer in duration than that of GH. This unique pharmacokinetic profile allows for intermittent administration of MOD-4023 to achieve pharmacodynamic effects in growth-hormone-deficient rat as evidenced by growth and elevations in plasma IGF-1 levels, respectively.

MOD-4023 offers a superior pharmacokinetic profile compared with that of GH when administered s.c. in the rat. There are substantial differences in plasma clearance of MOD-4023 compared to GH. Specifically, plasma is cleared of MOD-4023 at more than 6 times slower rate than of GH following s.c. dosing. The terminal half-life and mean residence time of MOD-4023 were approximately six times longer than that of GH in rats following s.c. administration. In addition, the Cl/F following s.c. dosing is 10 times lower for MOD-4023 than for GH.

In an effort to examine whether the pharmacokinetic advantages in the rat translated to a pharmacodynamic benefit, the possibility that MOD-4023 might stimulate growth in GH-deficient hypophysectomized rats with dosing regimens less frequent than daily was tested at equimolar MOD-4023 and GH dose levels. Single SC injection of MOD-4023 promoted incremental weight gain which was equal to 4 daily consecutive injections of GH. In addition, the every fourth day administration schedule for MOD-4023 shows enhanced body weight gain over GH.

Pharmacodynamically, the long circulation time of MOD-4023 relative to GH in the hypophysectomized rats resulted in a prolonged IGF-1 response measured in blood plasma following a single s.c. injection. Subcutaneous administration of a single dose of MOD-4023 increased circulating IGF-1 concentrations in a dose-dependent manner in the hypophysectomized rats. At the highest albutropin dose, IGF-1 concentrations were elevated above baseline for as long as 75 hours after a single administration. Thus, the enhanced circulation time of a single dose of MOD-4023 resulted in substantial pharmacodynamic improvement over a single dose of GH, raising the possibility that MOD-4023 could offer similar growth enhancement with reduced dosing frequency compared with standard GH treatment regimens.

Single CTPs modified hGH-dose of 90 mg/kg in Rhesus and 180 mg/kg in rats were well tolerated in both species. The allometric factor between rats and primates is approximately X2 which is based on the anticipated clearance of proteins in these animals. In-line with industry-accepted extrapolation models for therapeutic proteins' half-life increase between species (FDA Guidance). 90 mg/kg in Primates has a PK profile slightly better than 180 mg/kg of CTPs modified hGH in Rat. Thus, allometric extrapolation to humans supports weekly or once/2w injection.

The present concept utilizing a CTP-GH construct, reduced dosing frequency compared to the commercial GH recombinant product. Nutropin Depot® is a sustained release formulation of GH approved for use in pediatric populations; however, comparisons to historical controls have revealed that 1- and 2-year growth rates are significantly ($p<0.001$) lower in children given Nutropin Depot® (1-year growth rate 8.2±1.8 cm/year) than in children treated with GH (one-year growth rate 10.1±2.8 cm/year) (Silverman B L. Blethen S L. Reiter E O. Attie K M. Neuwirth R B. and Ford K M. A long-acting human growth hormone (Nutropin Depot®): efficacy and safety following two years of treatment in children with growth hormone deficiency. *J. Pediatr. Endocrinol. Metab.* 15 (2002), pp. 715-722.). The local effects of subcutaneously administered Nutropin Depot® include nodules, erythema, pain at the injection site, headache and vomiting. Preclinical toxicology studies in both rat and monkey have shown that s.c. administration of CTP-hGH-CTP-CTP produces no local reactions compared to vehicle. Given the medical need for a less frequently administered form of GH, the pharmacologic properties of MOD-4023 in this study in rats suggest that this product is favorable also in terms of toxicology and patients compliance. The sustained activity of MOD-4023 in the rat support its potential utility as an agent that requires only intermittent administration to attain a therapeutic benefit that is currently achieved with daily dosing.

Example 10

Construction of hIFN Beta-CTP Variants

Construction of hIFNβ-CTP variants: A cassette gene containing the C-Terminal peptide (CTP) of the beta subunit of hCG was fused to the coding sequence of human IFN beta 1a (SEQ ID NO: 49) at different locations. Seven IFNβ-CTP variants were constructed as illustrated in FIGS. 14A-14N. The proIFNβ signal peptide was used for the construction of the secreted IFNβ-CTP variants. XbaI-NotI fragments containing IFNβ sequences were ligated into the pCI-dhfr expression vector of the present invention.

Table 17 hereinbelow summarizes the primer sequences used for constructing the CTP-containing polypeptides of the present invention.

TABLE 17

| Primer number | SEQ ID NO | Sequence | Restriction site (underlined in sequence) |
|---|---|---|---|
| 40 | 20 | 5' GAAT<u>TCTAGA</u>GGACATGACCAAC 3' | XbaI |

TABLE 17 -continued

| Primer number | SEQ ID NO | Sequence | Restriction site (underlined in sequence) |
|---|---|---|---|
| 41$^R$ | 21 | 5' <u>GCGGCCGC</u>GGACTCATCAGTTC CTCAGGTAGCCG 3' | NotI |

IFNβ-1 901-1-p107-2 (IFNβ-1—SEQ ID NO: 53): The IFNβ-ctp clone was synthesized by GeneArt (Geneart No. 0609229).

Then the XbaI-NotI fragment containing IFNβ-ctp sequence was ligated into pCI-dhfr expression vector. The amino acid sequence of this clone is presented in SEQ ID NO: 52.

IFNβ-2 901-2-p113-3 (IFNβ-2—SEQ ID NO: 55): The XbaI/ApaI fragment (IFN-ctp) of pCI-dhfr-701-2-p24-2 (IFN-ctpx2) was replaced by the XbaI/ApaI fragment (IFNβctp) of 901-1-p107-2 to create a IFNβ☐ctpx2 clone. The amino acid sequence of this clone is presented in SEQ ID NO: 54.

IFNβ-4 901-4-p108-16 (IFNβ-4—SEQ ID NO: 59): The ctp-IFNβ-ctp-IFNβ☐clone was synthesized by GeneArt (Geneart No. 0609227).

Then the XbaI-NotI fragment containing sequence ctp-IFNβ-ctp-IFNβ was ligated into pCI-dhfr expression vector. The amino acid sequence of this clone is presented in SEQ ID NO: 11.

IFNβ-6 901-6-p109-3 (IFNβ-6 SEQ ID NO;16): The ctp-IFNβ-ctp clone was synthesized by GeneArt (Geneart No. 0609228).

Then the XbaI-NotI fragment containing sequence ctp-IFNβ-ctp was ligated into pCI-dhfr expression vector. The amino acid sequence of this clone is presented in SEQ ID NO: 62.

IFNβ-5-p103-10 (IFNβ-5 SEQ ID NO: 61—(ctp-IFNβ-): Primers were ordered from Sigma-Genosys. A PCR reaction was performed using primer 40 (SEQ ID NO: 65) and primer 41R (SEQ ID NO: 66) and plasmid DNA of the synthesized ctp-IFNβ-ctp (Geneart No. 0609228) as a template; as a result of the PCR amplification, a 677 bp product was formed. The PCR fragment was digested with XbaI-NotI and the fragment containing ctp-IFNβ sequence was ligated into our eukaryotic expression vector pCI-dhfr to yield the 901-5-p103-10 clone. The amino acid sequence of this clone is presented in SEQ ID NO: 60.

IFNβ-3 901-3-p114-5 (IFNβ-3 SEQ ID NO: 57-(ctp-IFN-CTP(×2)): The XbaI/ApaI fragment (IFN-ctp) of pCI-dhfr-701-2-p24-2 (IFN-ctpx2) was replaced by the XbaI/ApaI fragment (ctp-IFNβ-ctp) of 901-6-p109-3 to create a ctp-IFNβctpx2 clone. The amino acid sequence of this clone is presented in SEQ ID NO: 56.

IFNβ-901-0-p102-1 (IFNβ-0 SEQ ID NO: 51—(IFNβ): Primers were ordered from Sigma-Genosys. A PCR reaction was performed using primer 40 (SEQ ID NO: 65) and primer 41R (SEQ ID NO: 66) and plasmid DNA of the synthesized IFNβ-ctp (Geneart No. 0609229) as a template; as a result of the PCR amplification, a 599 bp product was formed. The PCR fragment was digested with XbaI-NotI and the fragment containing IFNβ sequence was ligated into our eukaryotic expression vector pCI-dhfr to yield the 901-0-p102-1 clone. The amino acid sequence of this clone is presented in SEQ ID NO: 50.

Example 11

Expression and Isolation of IFN-CTP Polypeptides

Materials and Methods

DNA Transfection and Clone Selection:

DG44 cells were transfected with pCI-DHFR expression vectors containing IFNβ-CTP variants using FuGENE6 Reagent (FuGENE Transfection Reagent—Roche Cat. 11 815 091 001). 48 hr following transfection, cells were diluted and seeded at 50-200 cells per well in a selective medium (CD DG44 Medium w/o HT (Gibco: Scotland part: #07990111A) Sku num.:ME060027 supplemented with 8 mM L-Glutamine Biological Industries: Cat: 03-020-1A) and 18 mL/L of 10% Pluronic F-68 solution (Gibco: Cat: 240040-032). Selected clones were screened for highest protein production using commercial ELISA. 3-5 producing clones per each variant were frozen for a backup cell bank. A selected clone for each variant was adapted to growth in larger scale cultures up to 1 L flasks on an orbital shaker platform. Supernatants were collected and analyzed by ELISA, SDS-PAGE and Western blot. Following the withdrawal of aliquots, the protein-containing supernatants were kept frozen until further use.

Cell Culture:

DG44 cells were maintained in DG44 medium with HT (cat#12610-010, Gibco) supplemented with 8 mM L-Glutamine (Biological Industries: Cat: 03-020-1A) and 18 mL/L of 10% Pluronic F-68 solution (Gibco: Cat: 240040-032), at 37° C. in humidified 8% CO2 incubator. Transfected clones were maintained in DG44 basal medium without HT supplement, hypoxanthine and thymidine, with pluronic acid and L-glutamine.

Sample Preparation:

Supernatants were collected, filtrated and analyzed by ELISA to determine protein concentration. SDS-PAGE and Western blot were used to determine purity and identity. Following ELISA, sample concentrations were defined and the solution was dialyzed against PBS. Following the withdrawal of aliquots, the protein-contained supernatants were kept frozen at −20° C. until further use.

Western Blotting:

Samples were electrophoresed on nondenaturing 15% SDS-polyacrylamide gels. Gels were allowed to equilibrate for 10 min in 25 mM Tris and 192 mM glycine in 20% (vol/vol) methanol). Proteins were transferred to a 0.2 μm pore size nitrocellulose membrane (Sigma, Saint Louis, Mo.) at 250 mA for 3 h, using a Mini Trans-Blot electrophoresis cell (Biorad Laboratories, Richmond, Calif.). The nitrocellulose membrane was incubated in 5% non-fat dry milk for 2 h at room temperature. The membrane was incubated with IFN anti-serum (1:1000 titer) overnight at 4° C. followed by three consecutive washes in PBS containing 0.1% Tween (10 min/wash). The membrane was incubated with secondary antibody conjugated to Horse Radish Peroxidase (HRP) (Zymed, San Francisco, Calif.) for 2 h at room temperature, followed by three washes. Finally, the nitrocellulose paper was reacted with enhanced chemiluminescent substrate (ECL) (Pierce, Rockford, Ill.) for 5 min, dried with a Whatman sheet, and exposed to X-ray film.

Figure 12:
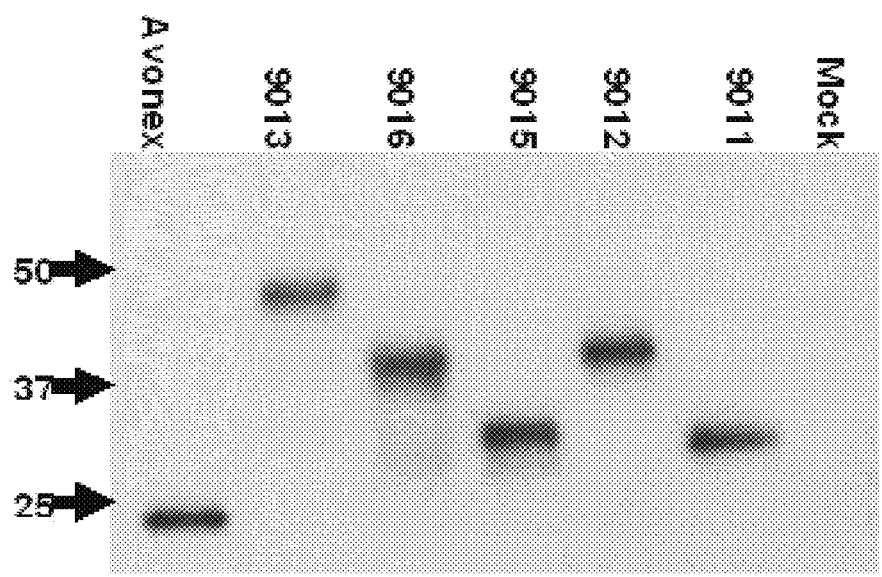
FIG. 12 is a Western blot illustrating the molecular weight & identity of Avonex®, MOD-9013 (SEQ ID NO: 56), MOD-9016 (SEQ ID NO: 62), MOD-9015 (SEQ ID NO: 60), MOD-9012 (SEQ ID NO: 54), MOD-9011 (SEQ ID NO: 52) and Mock. PAGE SDS gel was blotted and stained using monoclonal anti-IFN-β1A antibodies (B). The photograph indicates that like commercial Avonex®, MOD-901X variants are recognized by anti IFN-β1A antibodies.

FIG. 12 indicates that MOD-901X-variants are recognized by anti IFN-□1a antibodies. The SDS PAGE gel was stained using coomassie blue (A) or (B) blotted and stained using monoclonal anti-IFNβ1a antibodies Example 12

The IFN-CTP Polypeptides are Bioactive

To determine the bioactivity of MOD-901X variants through its recognition and binding to the IFN receptor. Daudi cell line (human Burkitt lymphoma) ATCC catalog No, CCL-213 TM (one of the most sensitive cell lines to the anti-proliferative effect of IFN-β1a) were used. Daudi cells, grown in suspension were treated with different concentrations of IFN-β1a (50-1000 µg/ml final concentration) and incubated for 72 hours. The number of viable cells was measured using CellTiter 96® AQueous One Solution Cell Proliferation Assay kit (Promega G3580) according to manufacturer procedures. The assay's standard curve was prepared using recombinant human IFN-β1a (PtoSpec-Tany TechnoGene).

IFN-β1a is a cytokine that exhibit antiviral activity against a variety of viruses. The potency of IFN-β1a as an antiviral agent can be determined by a viral cytophatic effect (CPE) bioassay that measures the ability of the protein to protect human lung carcinoma A549 cells (grown at 37° C., 5% CO2) challenged with encephalomyocarditis (ECM) virus. A549 cells were plated into 96 well microtiter plate. Serial dilutions of IFN-β1a standards and test samples were added and 24 h later the cells were challenged with ECP virus. Viable cells were quantified two days later.

The potency (titer) of an IFN-β 1a test sample is determined as the reciprocal of the dilution represented in the well in which 50% of the cell monolayer is protected from the CPE virus. The actual potency is calculated by comparing the sample's protective effect with the same effect of a reference standard calibrated in International Units, provided by the National Institute of Allergy and Infectious Diseases (NIH). The results are shown in Table 18.

TABLE 18

| | Specific Activity IU/mg × 10^8 | | |
|---|---|---|---|
| | Anti-viral | Anti-proliferation | IC50 pg/ml |
| Int. Standard | | 2.00 | 318 |
| INFb-0 | 3.90 | 2.53 | 251 |
| INFb-1 | 4.00 | 2.41 | 264 |
| INFb-2 | 4.00 | 1.90 | 334 |
| INFb-3 | 4.00 | 2.77 | 230 |
| INFb-5 | 4.00 | 6.24 | 102 |
| INFb-6 | 3.70 | 1.97 | 323 |

*concentration was determined by Elisa assay

Conclusion: The activity of MOD-901X variants as measured by its antiviral effects were at normal range of the Intl' standard and similar to rhIFN. Same effect was observed in anti-proliferation assay except for MOD-9015 which was 3 times more potent than the other variants. IFNβ-0 is (SEQ ID NO: 50). IFNβ-1 is (SEQ ID NO: 52, MOD-9011). IFNβ-2 is (SEQ ID NO: 54, MOD-9012). IFNβ-3 is (SEQ ID NO: 56, MOD-9013). IFNβ-4 is (SEQ ID NO: 58, MOD-9014). IFNβ-5 is (SEQ ID NO: 60, MOD-9015). IFNβ-6 is (SEQ ID NO: 62, MOD-9016).

Example 13

Comparative Pharmacokinetics (MOD-901X Variants, Avonex® and Rebif®)

In order to determine the pharmacokinetics of MOD-901x and compare it to that of commercial IFN-β1a (Rebif®, Avonex®) data statistical analysis was performed. The analysis included analysis of serum samples that was performed in order to determine specific concentration levels for each sample. Concentration and time-point data were processed using WinNonLin nocomparmental analysis. The following parameters were determined: AUC, CL, Ke, t½, Cmax, Tmax, and Vdz.

The experimental design is provided in table 19.

TABLE 19

| No. | Drug | N | Route | Species/Gender | Equimolar Dose (µgKg) | Dose Vol. (ml) | Time-Points* (hours post-dose) |
|---|---|---|---|---|---|---|---|
| 1 | Avomex | 3 | IV/SC | SD rat/Male | 38/66 | 0.3/0.5 | 0 (Pre-dose) 0.5, 4, 8, 24, 48, 96. |
| 2 | Rebif | 3 | IV/SC | SD rat/Male | 38/66 | 0.3/0.5 | 0.5, 4, 8, 24, 48, 96. |
| 3 | MOD-9011 | 3 | IV/SC | SD rat/Male | 38/66 | 0.3/0.5 | 0.5, 4, 8, 24, 48, 96. |
| 4 | MOD-9012 | 3 | IV/SC | SD rat/Male | 38/66 | 0.3/0.5 | 0.5, 4, 8, 24, 48, 96. |
| 5 | MOD-9013 | 3 | IV/SC | SD rat/Male | 38/66 | 0.3/0.5 | 0.5, 4, 8, 24, 48, 96. |
| 6 | MOD-9015 | 3 | IV/SC | SD rat/Male | 38/66 | 0.3/0.5 | 0.5, 4, 8, 24, 48, 96. |
| 7 | MOD-9016 | 3 | IV/SC | SD rat/Male | 38/66 | 0.3/0.5 | 0.5, 4, 8, 24, 48, 96. |

3 rats per time point.

3 rats per time point.

Figure 13:
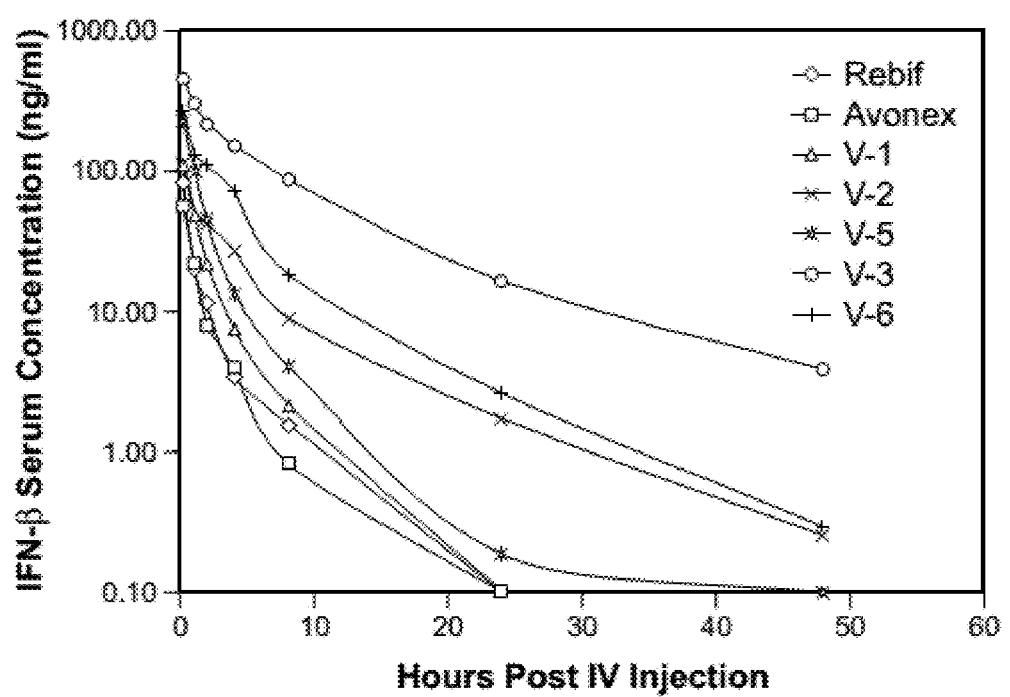
FIG. 13 presents the mean plasma IFN-β1a or MOD-901x varients concentrations (ng/ml) following single-dose IV administration of IFN-β1a or MOD-901x varients in SD rats (n=3 per dose/route/timepoint). IFN-β1a serum concentrations were determined using commercial ELISA kit.
Figure 15:
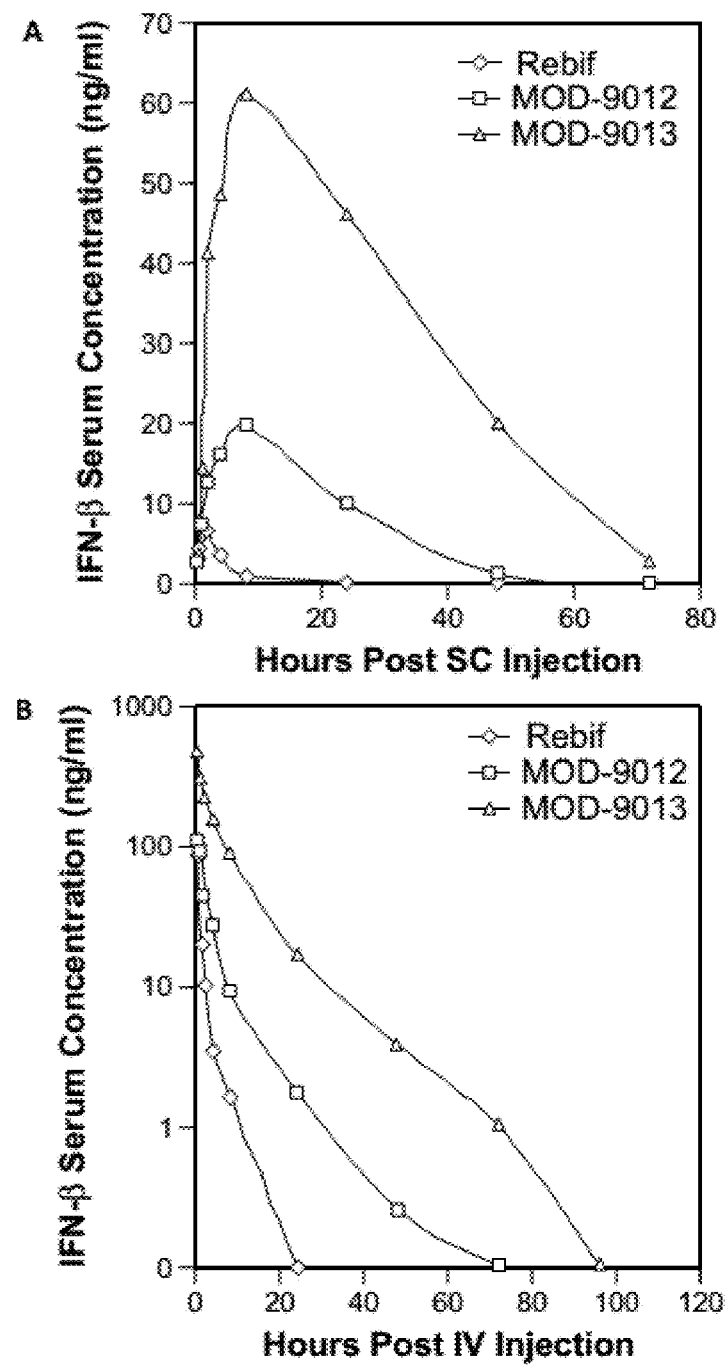
FIG. 15. are graphs showing the mean plasma concentrations (ng/ml) of Rebif®, MOD-9012, and MOD-9013 following single-dose s.c.
Figure 16:
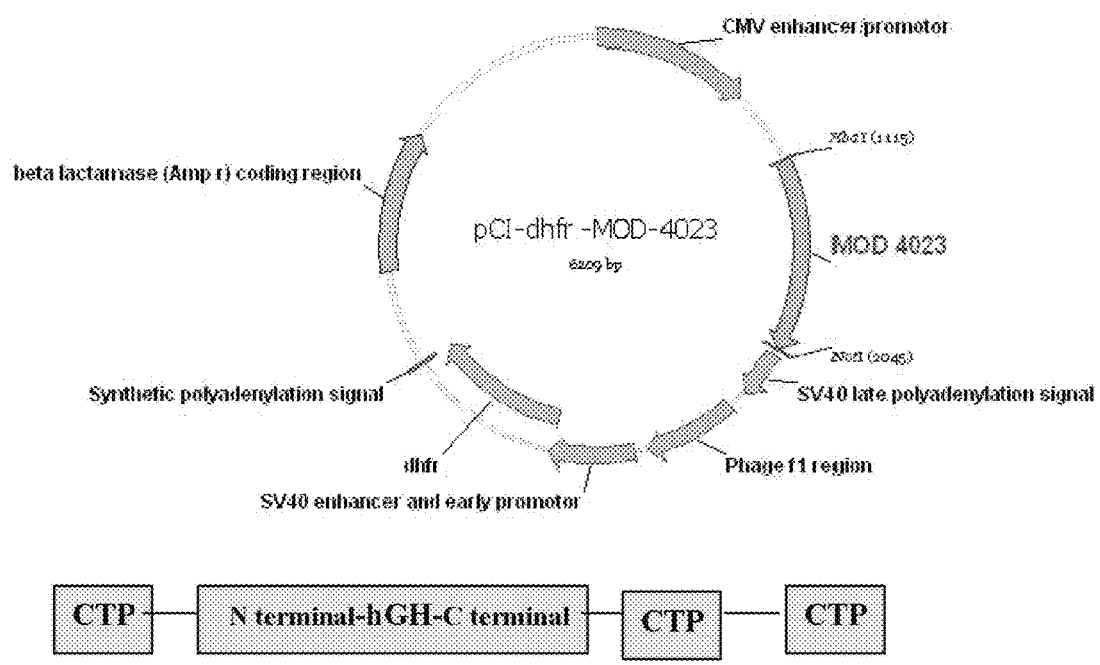
FIG. 16 includes two schemes (1) a map of MOD 4023 pCI-dhfr Plasmid and (2) structural protein formula of MOD-4023.

FIG. 13 show the change in serum concentration of IFN-β1a or MOD-901x concentrations (ng/ml) following single-dose IV administration of IFN-1a or MOD-901x in SD rats.

Table 20 show the mean pharmacokinetic parameters following single-dose IV or Sub-Cutaneous (SC) administration of IFN-β1a and MOD-901x in Spargue-Dawley rats.

TABLE 20

PK Statistics

| Parameters | Units | Avonex | Rebif | MOD-9011 | IV MOD-9012 | MOD-9015 | MOD-9013 | MOD-9016 |
|---|---|---|---|---|---|---|---|---|
| Dose | μα | 5 | 5 | 5 | 5 | 5 | 5 | 5 |
| AUClast | Hr*ng/mL | 83.9 | 106.4 | 185.3 | 417 | 369.4 | 2562.9 | 879.6 |
| Cmax | ng/ml | | | | | | | |
| Tmax | hr | | | | | | | |
| MRT | hr | 1.5 | 1.3 | 2.1 | 11.3 | 2 | 12.1 | 9.6 |
| T½ α | hr | 1.02 | 0.9 | 1.43 | 2.17 | 1.4 | 2.53 | 2.22 |
| T½ β | hr | | | | 7.82 | | 8.36 | 6.66 |

Parameters was generated for individual rats and mean data are presented here.

Parameters was generated for individual rats and the mean data are presented here.

In conclusion: IFN-β1a with 3 CTP units has 8 times longer half-life than that of Rebif® or Avonex® when injected IV.

FIG. 13 shows the mean plasma of Rebif®, MOD-9012, and MOD-9013 concentrations (ng/ml) following single-dose IV or SC administration of IFN-β1a, MOD-9012 or MOD-9013 in SD rats (n=3 per dose/route/timepoint). IFN-β1a serum concentrations were determined using commercial ELISA kit.

Table 21 displays the mean pharmacokinetic parameters following single-dose IV or SC administration of Rebif®, MOD-9012, and MOD-9013 in Spargue-Dawley rats.

MOD-9013 was compared in SD rats to Rebif® and Avonex®. Following a single IV/SC injection of 38/66 μg/kg, Clearance of MOD-9013 from SD rats blood was significantly slower than that for Rebif® and Avonex®. The corresponding calculated half life times and AUCs were: For IV administration:

| Rebif ® | T½ 1 h, AUC106 hr*ng/mL |
|---|---|
| MOD-9013 | T½ 8.4 h, AUC2563 hr*ng/mL |

For SC administration the corresponding calculated half-life times and AUCs were:

TABLE 21

PK Statistics

| Parameters | Units | Rebif | SC MOD-9012 | MOD-9013 | Parameters | Rebif | IV MOD-9012 | MOD-9013 |
|---|---|---|---|---|---|---|---|---|
| Dose | μα | 10 | 10 | 10 | Dose | 5 | 5 | 5 |
| AUClast | Hr*ng/mL | 34.8 | 498.5 | 2299.5 | AUClast | 106.4 | 417 | 2562.9 |
| Cmax | ng/ml | 6.6 | 19.7 | 61.1 | Cmax | | | |
| Tmax | hr | 2 | 8 | 8 | Tmax | | | |
| MRT | hr | 4.1 | 15.9 | 24.1 | MRT | 1.3 | 11.3 | 12.1 |
| T½ ab | hr | 0.6 | 2.75 | 3.1 | T½ α | 0.9 | 2.17 | 2.53 |
| T½ el | hr | 2.1 | 9.5 | 14.2 | T½ β | | 7.82 | 8.36 |

Parameters were generated for individual rats and the mean data are presented.

Parameters were generated for individual rats and the mean data are presented.

In conclusion, IFN-β1a with 3 CTP units (MOD-9013) has 9.2 times longer half-life than that of Rebif® when injected IV and 6.7 times longer half-life when injected SC. AUClast of MOD-9013 is 66 times better then Rebif® when injected SC and 24 times when injected IV. MRT of MOD-9013 is 5.8 times better when injected SC and 9.3 times when injected IV.

The MOD-9013 molecule which comprises one CTP attached to the N-terminus of IFN-β1a and two CTP attached to its C-terminus was tested in-vitro for its ability to bind to the human IFN receptor and in-vivo for its pharmacokinetic performance. The conclusions of these studies can be summarized as follows: (1) The in-vitro anti-proliferation activity of MOD-9013 as demonstrated in the daudi cells assay was similar to the international standard and to that of MOD-9010 (rIFN-β1a expressed by Modigene). (2) The anti-viral protective activity of MOD-9013 shown in Daudi cells was same as the international standard and as of that of MOD-9010 (rIFN-β1a expressed by Modigene). (3) In terms of its pharmacokinetic features

| Rebif ® | T½ 2.1 h, AUC34.8 hr*ng/mL |
|---|---|
| MOD-9013 | T½ 14.2 h, AUC2299.5 hr*ng/mL |

The superior performance of MOD-9013 to stimulate anti-viral and anti-proliferation activity and to retain long lasting stimulation results from three main reasons: i) Addition of up to 24 sialic acid residues; ii) Stabilizing effect on the IFN-β1a molecule by fusing the CTP cassettes to both N and C termini; and iii) Increase in molecular weight of the whole molecule from ~31,242-48,000 Daltons.

As shown hereinabove, different levels of potency were exerted by IFN-CTP polypeptides, indicating differences in receptor binding. IFN-CTP polypeptides differ by the number of CTP cassettes and the location to which they are fused. MOD-9011 and MOD-9012 contain 1 CTP sequence or 2 CTP sequences at the C-terminal of IFN protein, while MOD-9013 contains 1 CTP at N-terminal and 2 CTP sequences at C-terminals. MOD-9014 is a dimer of two IFN molecules linked by CTP sequence. MOD-9013 demonstrated unexpected potency level.

What is claimed is:

1. A polypeptide consisting of an interferon and optionally a signal peptide, wherein a first chorionic gonadotropin carboxy terminal peptide is attached to the amino terminus of said interferon, and a second and third chorionic gonadotropin carboxy terminal peptide are attached to the carboxy terminus of said interferon, wherein said third chorionic gonadotropin carboxy terminal peptide is attached in tandem to said second chorionic gonadotropin carboxy terminal peptide.

2. The polypeptide of claim 1, wherein the sequence of at least 1 of said chorionic gonadotropin carboxy terminal peptides is an amino acid sequence selected from sequences set forth in SEQ ID NO: 17 and SEQ ID NO: 18.

3. The polypeptide of claim 1, wherein at least 1 of said chorionic gonadotropin carboxy terminal peptides is truncated.

4. The polypeptide of claim 1, wherein said interferon is glycosylated.

5. The polypeptide of claim 1, wherein said interferon is non-glycosylated.

6. The polypeptide of claim 1, wherein at least 1 of said chorionic gonadotropin carboxy terminal peptides is glycosylated.

7. The polypeptide of claim 1, wherein at least 1 of said chorionic gonadotropin carboxy terminal peptides is attached to said interferon via a linker.

8. The polypeptide of claim 1, wherein when said optional signal peptide is present, the amino acid sequence of said signal peptide is set forth in SEQ ID NO: 64.

9. A pharmaceutical formulation comprising the polypeptide of claim 1, wherein said formulation further comprises a buffer, and a tonicity agent.

10. The formulation of claim 9, wherein said buffer is citrate or acetate.

11. The formulation of claim 9, wherein said tonicity agent is sodium chloride.

12. The formulation of claim 9, wherein said formulation is formulated for injection in a multidose container, with optionally, a preservative.

13. The formulation of claim 12, wherein said preservative is benzalkonium chloride or thimerosal.

14. A liquid formulation, comprising the formulation of claim 13.

15. The polypeptide of claim 1, wherein when said second and third chorionic gonadotropin carboxy terminal peptide are attached to said carboxy terminus, the amino acid sequence of said polypeptide is set forth in amino acids 22-271 of SEQ ID NO: 56.

16. A method of extending the biological half-life of an interferon, comprising attaching two or three chorionic gonadotropin carboxy terminal peptides to said interferon, wherein a first chorionic gonadotropin carboxy terminal peptide is attached to an amino terminus of said interferon, and either only a second chorionic gonadotropin carboxy terminal peptide is attached to the carboxy terminus of said interferon or two chorionic gonadotropin carboxy terminal peptides are attached to a carboxy terminus of said interferon, thereby extending the biological half-life of said interferon.

* * * * *